United States Patent
Bonifas et al.

(10) Patent No.: US 10,363,502 B2
(45) Date of Patent: Jul. 30, 2019

(54) ELECTROMAGNETIC SENSOR FOR ACTIVE MONITORING OF FILTER MEDIA WITHIN A FILTRATION SYSTEM

(71) Applicant: 3M INNOVATIVE PROPERTIES COMPANY, St. Paul, MN (US)

(72) Inventors: Andrew P. Bonifas, Alberta (CA); Brock A. Hable, Woodbury, MN (US); Nicholas G. Amell, Burnsville, MN (US); Jaewon Kim, Woodbury, MN (US); Ronald D. Jesme, Plymouth, MN (US); Jeffrey M. Maki, Inner Grove Heights, MN (US); Robert E. Astle, Middlefield, CT (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 15/749,647

(22) PCT Filed: Aug. 5, 2016

(86) PCT No.: PCT/US2016/045823
§ 371 (c)(1),
(2) Date: Feb. 1, 2018

(87) PCT Pub. No.: WO2017/030809
PCT Pub. Date: Feb. 23, 2017

(65) Prior Publication Data
US 2018/0221796 A1 Aug. 9, 2018

Related U.S. Application Data
(60) Provisional application No. 62/263,431, filed on Dec. 4, 2015, provisional application No. 62/205,481, filed on Aug. 14, 2015.

(51) Int. Cl.
*B01D 35/143* (2006.01)
*B01D 46/42* (2006.01)
(Continued)

(52) U.S. Cl.
CPC ....... *B01D 35/143* (2013.01); *B01D 46/0005* (2013.01); *B01D 46/429* (2013.01);
(Continued)

(58) Field of Classification Search
CPC ............... B01D 27/101; B01D 35/143; B01D 46/0086; B01D 2201/52; B01D 46/429;
(Continued)

(56) References Cited

U.S. PATENT DOCUMENTS

| | | | |
|---|---|---|---|
| 2,065,379 | A | 12/1936 | Knerr et al. |
| 3,422,346 | A | 1/1969 | Hammer |

(Continued)

FOREIGN PATENT DOCUMENTS

| | | |
|---|---|---|
| CN | 203048712 | 7/2013 |
| CN | 104364638 A | 2/2015 |

(Continued)

OTHER PUBLICATIONS

International Search Report for PCT International Application No. PCT/US2016/045823 dated Dec. 9, 2016, 6 pages.
(Continued)

*Primary Examiner* — Joseph W Drodge
(74) *Attorney, Agent, or Firm* — X. Christina Huang

(57) ABSTRACT

In general, techniques are described for filter media monitoring within a filtration system. The filter media monitoring techniques described herein include, for example, direct contact with the filter media, e.g., a sensor may be located inside a boundary defined by a surface of the filter media, or indirect contact with the filter media, e.g., a sensor may be located outside the boundary defined by the surface of the (Continued)

filter media such that the sensor does not make direct physical contact with the filter media being monitored.

11 Claims, 45 Drawing Sheets

(51) Int. Cl.
| | |
|---|---|
| *C02F 1/00* | (2006.01) |
| *C02F 1/48* | (2006.01) |
| *G01R 27/04* | (2006.01) |
| *G01N 27/90* | (2006.01) |
| *B01D 46/00* | (2006.01) |

(52) U.S. Cl.
CPC .............. *C02F 1/001* (2013.01); *C02F 1/485* (2013.01); *G01N 27/9046* (2013.01); *G01R 27/04* (2013.01); *B01D 2201/52* (2013.01)

(58) Field of Classification Search
CPC ................ B01D 46/0005; C02F 9/005; C02F 2009/445; C02F 1/001; C02F 1/485; G01R 19/00; G01R 19/0046; G01R 19/0092; G01R 19/12; G01R 29/22; G01R 27/04; G01N 27/9046
USPC ..... 210/85, 282, 739, 746; 96/417; 324/713, 324/715; 340/603, 606, 609, 620, 632
See application file for complete search history.

(56) References Cited

U.S. PATENT DOCUMENTS

| | | | |
|---|---|---|---|
| 5,865,991 A | 2/1999 | Hsu | |
| 6,139,739 A * | 10/2000 | Hamlin | B01D 61/18 210/315 |
| 6,558,444 B1 | 5/2003 | Hunter | |
| 7,811,365 B2 * | 10/2010 | Grzonka | B01D 35/06 174/17 CT |
| 8,384,396 B2 * | 2/2013 | Bromberg | B01D 46/0086 123/679 |
| 8,482,298 B2 | 7/2013 | Boudaoud et al. | |
| 8,501,119 B2 | 8/2013 | Burke et al. | |
| 8,814,996 B2 | 8/2014 | Giurgiutiu et al. | |
| 8,957,778 B2 * | 2/2015 | Adams | B01L 3/545 235/385 |
| 9,808,754 B2 * | 11/2017 | Stoner, Jr. | B01D 46/001 |
| 2003/0025598 A1 | 2/2003 | Wolf et al. | |
| 2003/0168389 A1 * | 9/2003 | Astle | B01D 27/101 210/85 |
| 2004/0256328 A1 * | 12/2004 | Jornitz | B01D 35/143 210/739 |
| 2006/0032379 A1 * | 2/2006 | Kates | F24F 3/1603 96/417 |
| 2006/0060512 A1 * | 3/2006 | Astle | B01D 27/101 210/85 |
| 2006/0065607 A1 * | 3/2006 | Bassett | B01D 29/114 210/767 |
| 2006/0191826 A1 | 8/2006 | Chajec | |
| 2009/0246090 A1 * | 10/2009 | Burke | H01Q 1/22 422/119 |
| 2010/0231196 A1 * | 9/2010 | Wright | B01D 53/0454 324/109 |
| 2011/0024337 A1 | 2/2011 | Kreibig et al. | |
| 2014/0208950 A1 * | 7/2014 | Giurgiutiu | B01D 53/02 96/153 |
| 2015/0097579 A1 * | 4/2015 | Sharma | G01N 22/00 324/637 |
| 2015/0355110 A1 * | 12/2015 | Sappok | G01N 1/44 324/639 |
| 2015/0358091 A1 * | 12/2015 | Sappok | H04B 17/00 455/67.11 |
| 2016/0029966 A1 * | 2/2016 | Salas-Boni | A61B 5/02055 600/347 |
| 2017/0182447 A1 * | 6/2017 | Sappok | F01N 11/00 |

FOREIGN PATENT DOCUMENTS

| | | |
|---|---|---|
| DE | 10151269 | 5/2003 |
| JP | H0731968 | 2/1995 |
| JP | 2015-040807 | 3/2015 |
| KR | 10-2002-0007525 | 1/2002 |
| WO | WO 2010-045936 | 4/2010 |
| WO | WO 2010-074812 | 7/2010 |
| WO | WO 2014-117000 | 7/2014 |

OTHER PUBLICATIONS

Hansen, Formulas for cavity resonators. Journal of Applied Physics, vol. 9, p. 654-663, Oct. 1938.

Mason, "HEPA Filter Material Load Detection Using a Microwave Cavity Sensor", International Journal on Smart Sensing and Intelligent Systems, vol. 3, No. 3, Sep. 2010, pp. 322-337.

Mason, "Determination of Activated Carbon Residual Life using a Microwave Cavity Resonator", Journal of Physics: Conference Series 307 (2011)012041, pp. 1-6.

Mason, "Electromagnetic (EM) Cavity Resonance Residual Life Indicator", IEEE Symposium on Computers & Informatics, 2011, pp. 796-799.

Smiechowski, "AC Impedance Monitoring of Activated Carbon Filter Contamination", ECS Transactions, 41 (28) 57-67, 2012.

* cited by examiner

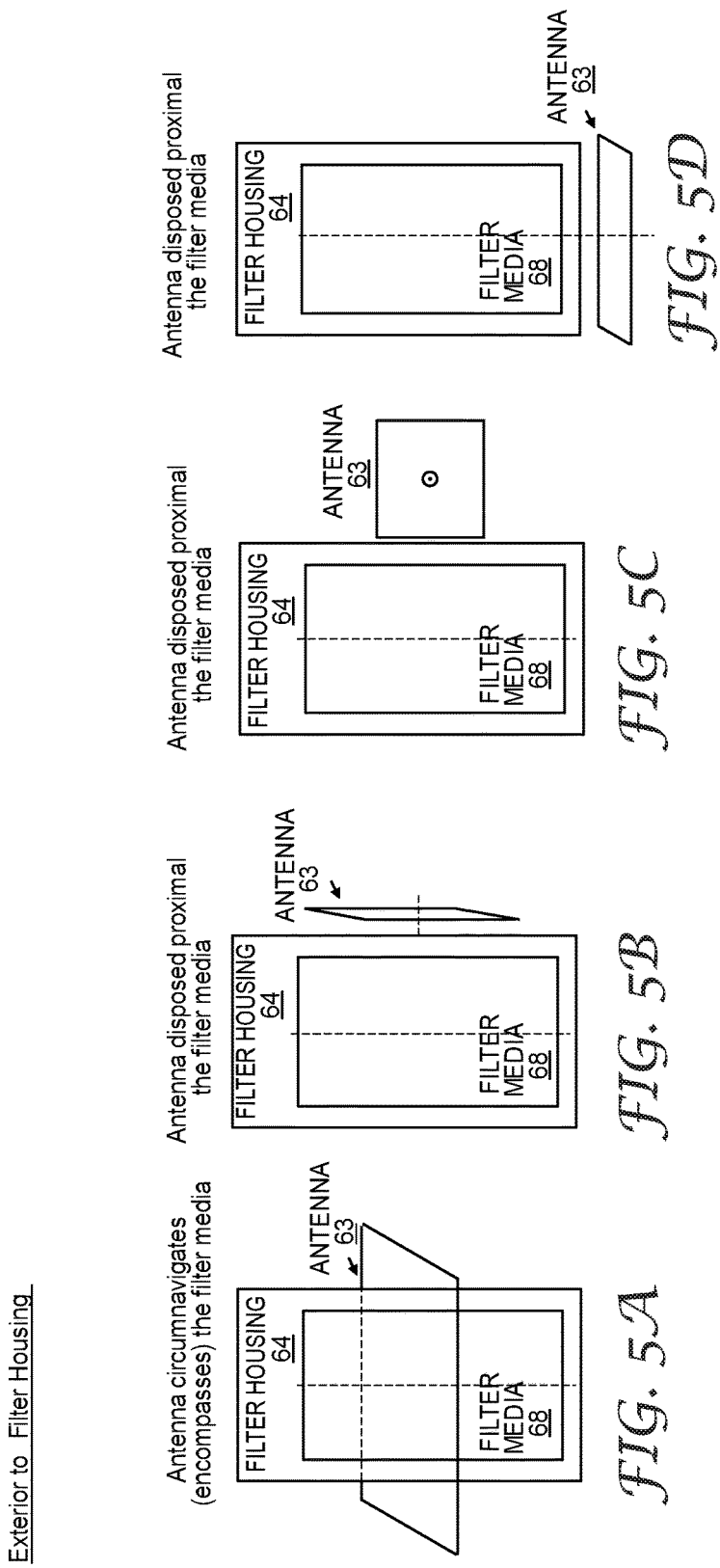

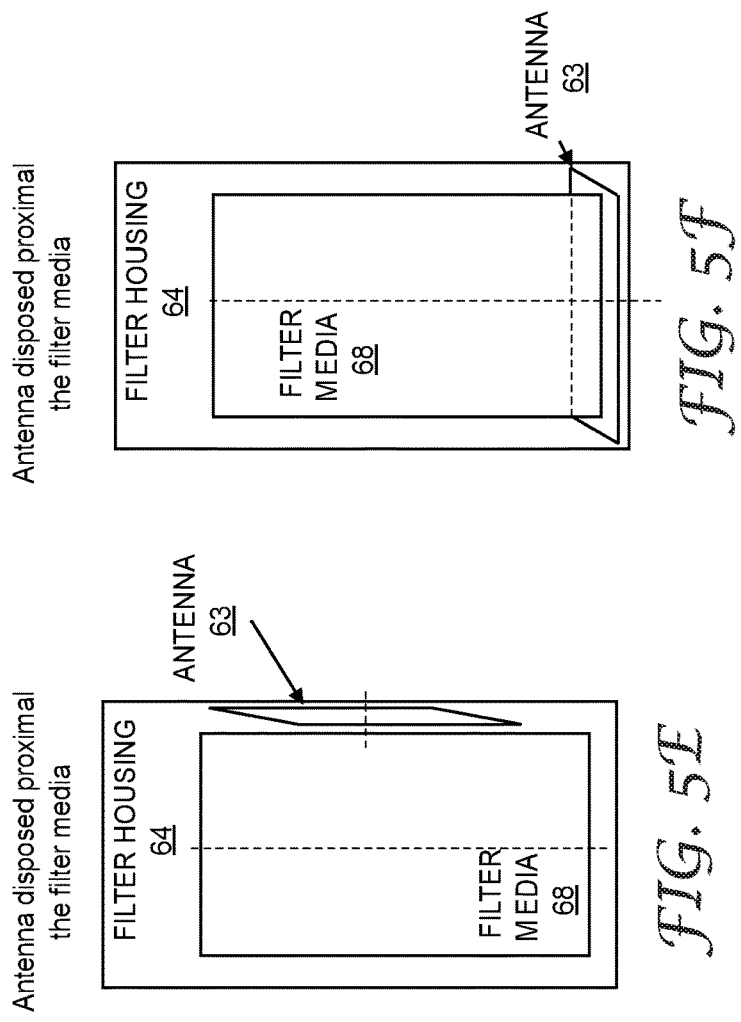

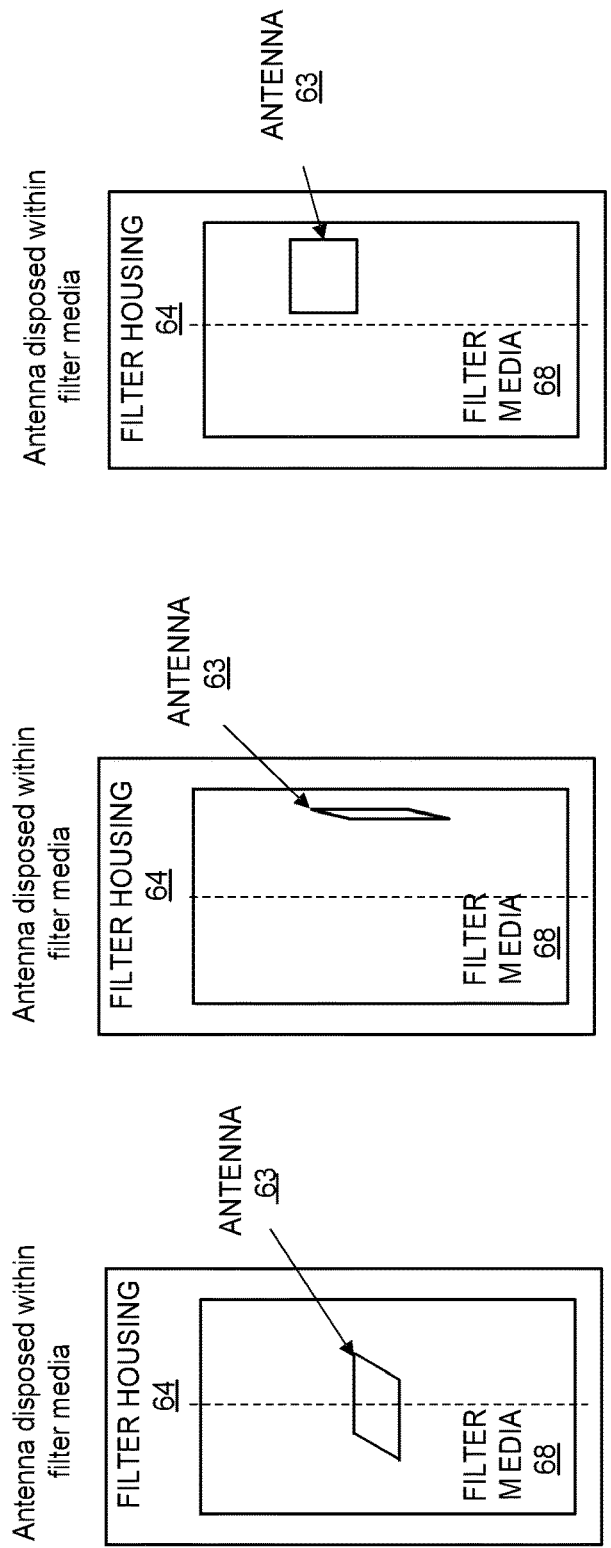

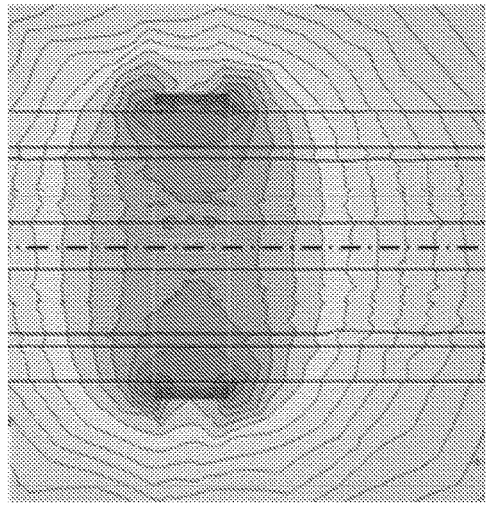
Antenna - No Band
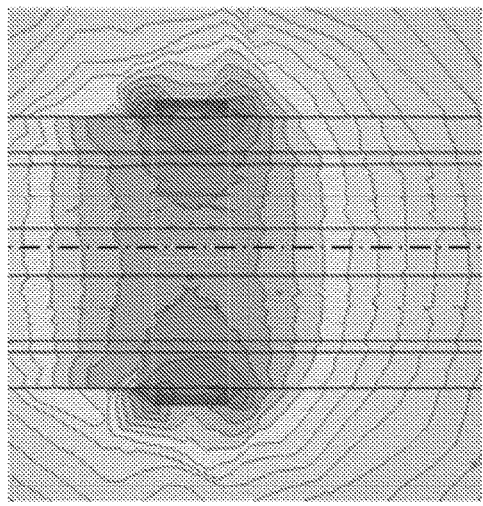
Antenna - 1/4" Cu Band
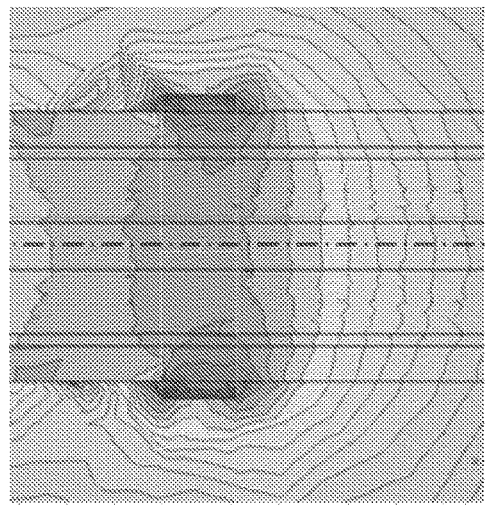
Antenna - 1" Cu Band
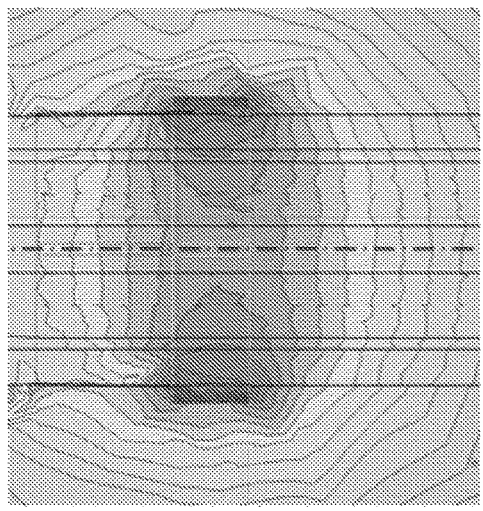
Antenna - 1" Mag. Band
FIG. 39

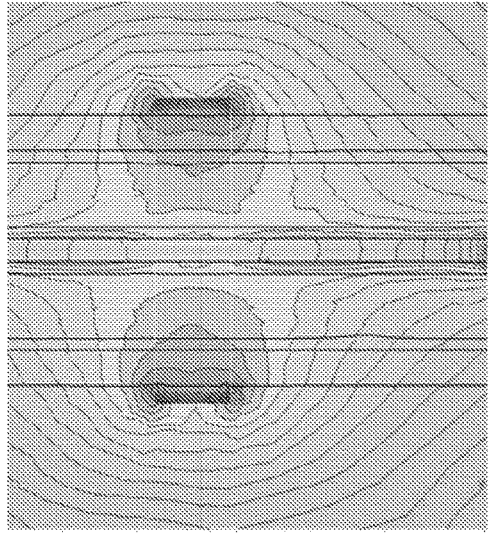
Long Core Magnetic Band
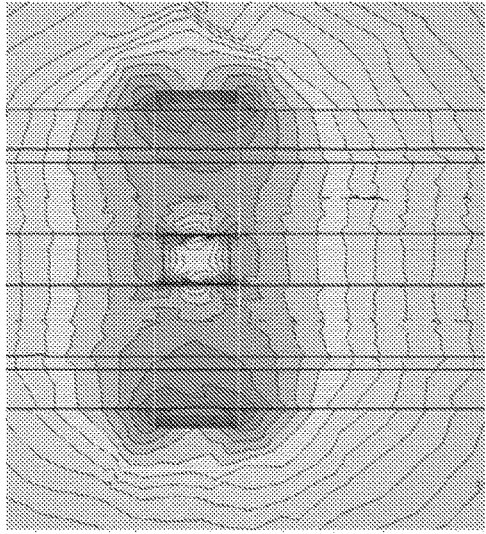
12mm Core Magnetic Band
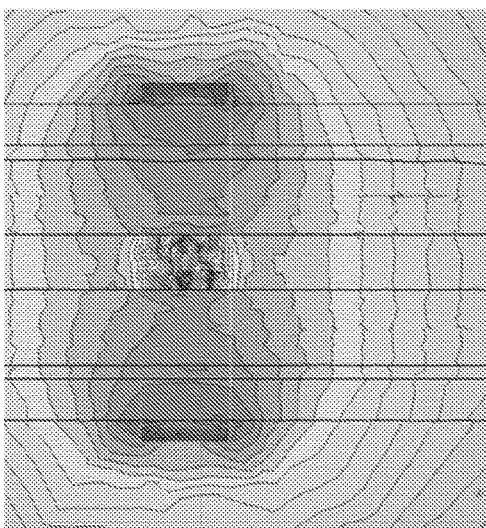
12mm Core Copper Band
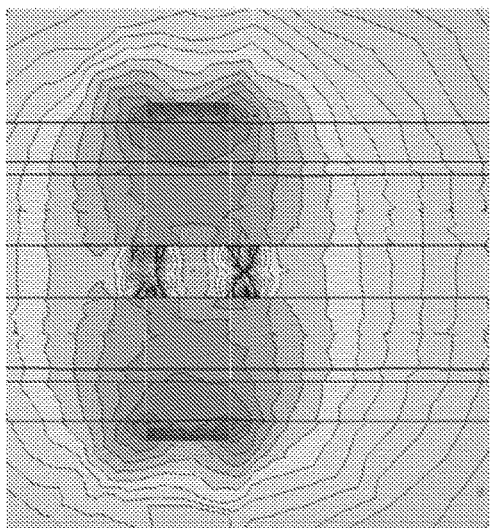
Two 5mm Core Copper Bands
FIG. 42

ELECTROMAGNETIC SENSOR FOR ACTIVE MONITORING OF FILTER MEDIA WITHIN A FILTRATION SYSTEM

CROSS REFERENCE TO RELATED APPLICATIONS

This is a national stage filing under 35 U.S.C. 371 of PCT/US2016/045823, filed Aug. 5, 2016, which claims priority to U.S. Provisional Application No. 62/205,481, filed Aug. 14, 2015, and U.S. Provisional Application No. 62/263,431, filed Dec. 4, 2015 the disclosure of which is incorporated by reference in its/their entirety herein.

TECHNICAL FIELD

The disclosure relates to filtration systems and filter media monitoring.

BACKGROUND

Filtration is the separation of one or more particles from a fluid, including gases and liquids. A wide range of filtration processes are used in various residential, commercial, and industrial applications. Depending on the particular application, a filtration process may use one or more filter media to capture or otherwise remove particulates, impurities, chemical compounds, or the like. For example, the provision of water with sufficient purity and quality is important for many residential, commercial, and industrial applications. Water filtration may, for example, use activated carbon as a filter media. Water filtration by activated carbon may involve passing a water stream through a bed of activated carbon filter media. The activated carbon may remove from the water various particulates, impurities, chemical compounds, or the like, which affect the purity or quality. In this way, activated carbon filtration may improve water safety, taste, odor, appearance, or the like.

SUMMARY

In general, techniques are described for filter media monitoring within a filtration system. The filter media monitoring techniques described herein include, for example, direct contact with the filter media, e.g., a sensor may be located inside a boundary defined by a surface of the filter media, or indirect contact with the filter media, e.g., a sensor may be located outside the boundary defined by the surface of the filter media such that the sensor does not make direct physical contact with the filter media being monitored.

As one example, sensors are described that generate and utilize an electromagnetic field for actively monitoring the capacity of a filter media. In other examples, sensors are described that utilize a housing containing the filter media as a resonant cavity and are operable to determine properties of the filter media based on sensed measurements from the resonant cavity. As such, various sensors are described that may be easily mounted on, located proximate to, or integrated within housings containing the filter media so to as non-invasively provide active monitoring of the current state of the filter media.

As another example, sensors are described that determine the remaining capacity of a filtration media by conductive contact probes so as to provide electrical contact with the filter media. The probes may, for example, be integrated within or otherwise extend through the housing to contact the filter media.

In additional examples, filtration systems are described in which an array of multiple sensors is positioned within a filtration system. The multiple sensors may be positioned serially along a flow path and/or in parallel along multiple flow paths to provide monitoring at various locations within the filtration system. Moreover, multiple sensors may be positioned along the flow path for a common filter media such that the sensors provide spatial monitoring for the filter media.

In other examples, sensing systems are described that provide automated identification for the filter media currently deployed within the filtration system. For example, in some implementations, non-contact identification bands may be incorporated within or otherwise affixed proximate to the housings containing the filter media. As described herein, the identification bands may be constructed so as to influence the magnetic sensing of the filter media by a sensor mounted on the housing. For example, the identification bands may be electrically conductive and/or magnetic so as to be sensed by the sensor. Moreover, the bands may be geometrically or spatially arranged so as to provide a unique identification of the filter media, such as when the filter media in inserted into the filtration system and passed through a sensing field of the sensor. In this way, the identification bands may be utilized to provide an affirmative identification of the filter media.

As described herein, a controller may communicate with the sensors to sense and actively monitor one or more parameters of the filter media in accordance with the techniques described herein including, for example, the filter media conductivity, dielectric strength, magnetic permeability, or the like. The filter media monitoring techniques described herein may be applied in various fluid filtration applications, for example, the filtration of gases or liquids.

Responsive to measurements from the sensors, the controller may output alerts or other signals indicative of a predicted filter media lifetime or determined current capacity of the filter media deployed throughout a filtration system.

The details of one or more examples of the techniques are set forth in the accompanying drawings and the description below. Other features, objects, and advantages of the techniques will be apparent from the description and drawings, and from the claims.

BRIEF DESCRIPTION OF DRAWINGS

FIGS. 5A-5K are block diagrams illustrating example arrangements of sensing systems described herein and, in particular, illustrate example relative positions and orientations between an antenna of the filter sensor and the filter media.

FIG. 39 shows a four contour plot of a magnetic field of the simulated filter identification system.

FIG. 42 shows contour plots of the simulated magnetic fields generated by the filter arrangements of FIG. 41 in which a resonant antenna is used with conductive or magnetic bands located on the inner surface of the filter.

DETAILED DESCRIPTION

Figure 1:
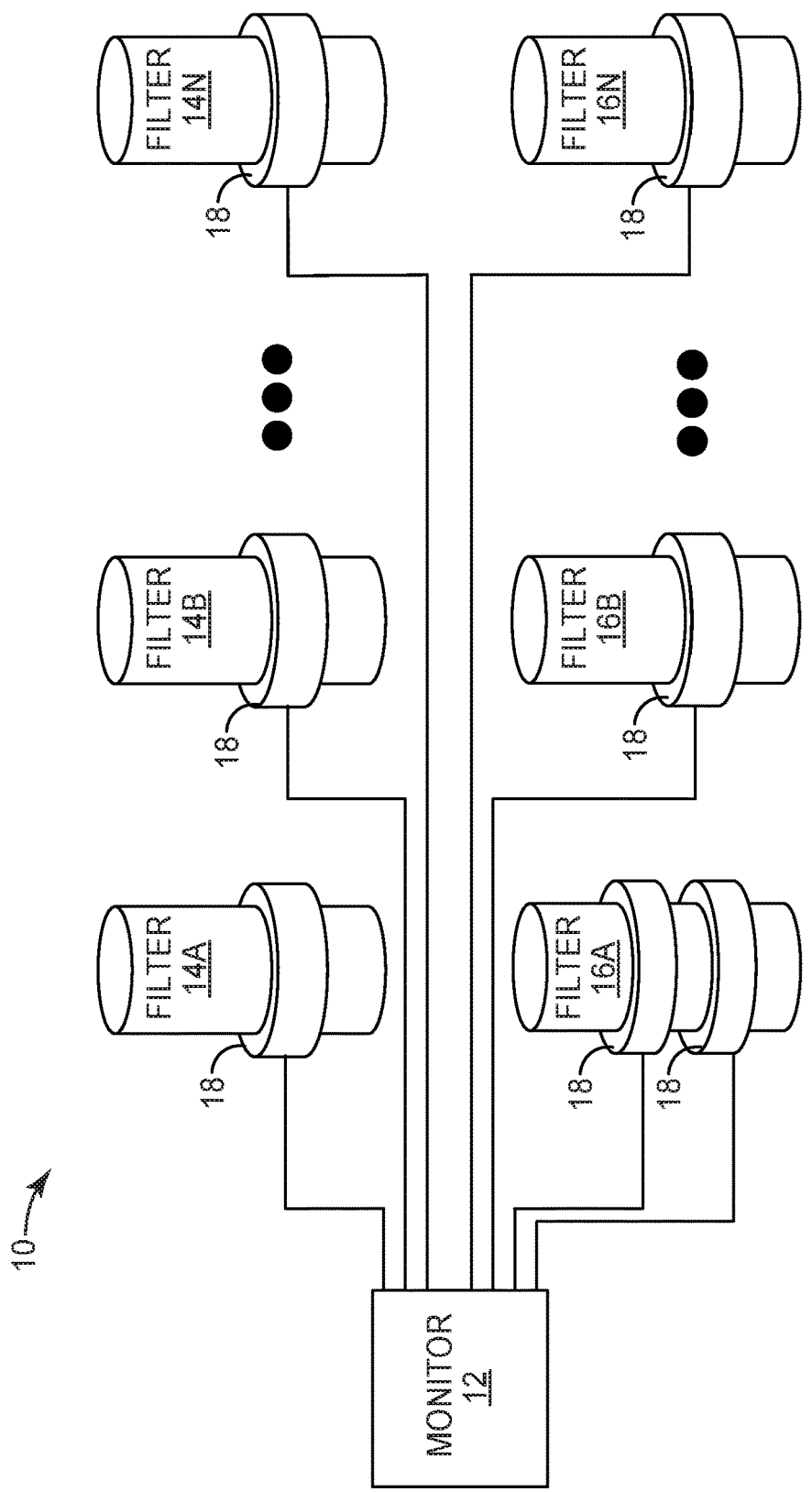
FIG. 1 is a block diagram illustrating an example filtration system in which a monitor is coupled to filter media sensors associated with a plurality of filter housings containing filter media.

FIG. 1 is a block diagram illustrating filtration monitoring system 10 in which a monitor 12 is communicatively coupled to sensors 18 associated with filter housings 14, 16. In the example of FIG. 1, filter monitoring system 10 includes, for example, monitor 12 interfaced sensors 18 mounted on respective filter housings 14A-14N (collectively, "filter housings 14") and filter housing 16A-16N (collectively, "filter housings 16"). In some examples, monitor 12 may be connected to fewer sensors, e.g. one sensor, or more sensors. Moreover, sensors 18 may be directly connected to the monitor 12 by, for example, a data bus, discrete electrical wires, or the like. In other examples, any of sensors 18 may be indirectly connected to monitor 12 by, for example, radio frequency communication, wireless local area network (WLAN) connection, or the like. In some examples, sensors 18 may be positioned adjacent and external to filter housings 14, 16. For example, sensors 18 may be configured to physically and securely mount on filter housings 14, 16. In other examples, sensors 18 may be integrated within filter housings 14, 16.

In the example of FIG. 1, filter housings 14 are in fluid communication such that fluid flows (e.g., gas or liquid) sequentially along a first flow path through the series of filter housings 14. Similarly, filter housings 16 are in fluid communication along a second flow path of filtration monitoring system 10. Moreover, as shown in FIG. 1 merely for purposes of example, the first flow path along which filter housings 14 are positioned and the second flow path along which filter housings 16 are positioned are parallel to each other. In this way, sensors 18 may be deployed so as to provide monitoring at various locations within the filtration system. Moreover, as shown with respect to filter housing 16A, multiple sensors may be positioned along the flow path for a common filter media (e.g., affixed to a common housing) such that the sensors 18 provide spatial monitoring for a common filter media. In other examples, multiple filter housings 14, 16 may define different sections for housing of a single continuous filter media. Further, filter housings 14, 16 need not be identical and may be configured to contain different types of filter media.

In some cases, filtration monitoring system 10 is implemented as a plurality of filtration systems coupled in fluid communication, where the filtration system includes a filter manifold, a filter housing, and a filter media. In general, the filter media is contained within the filter housing and the housing is a means to control the fluid flow, provide mechanical support for the filter media, and enable a connection method between the filter media and filter manifold. In various examples, each filter housing 14 may be a cartridge adapted and configured to interact with and otherwise detachably interconnect with a connector head that is in direct communication with a source of treatable fluid, such as, for example, a source of untreated drinking water. Further details of example filter systems, including filter cartridges detachably interconnected with a filtration system are described in U.S. Patent Publication US20030168389, the entire content of which is incorporated herein by reference.

In one example, for water filtration applications, the filter housing may be comprised of a plastic material, such as polyethylene, polypropylene, and polycarbonate. In other examples, the housing may comprised of a metal or ceramic. In a second example, for air filtration, the filter housing may comprise of a cardboard, plastic, or metallic frame. The filter housing may consist of a wide variety of shapes, including cylindrical, conical, and prismatic. The filter housing may be designed to be disposable or reusable and, in case of reusable, configured to enable the replacement of the filter media. The filter housing may be configured to attach, connect, or screw into a filter manifold and provide a fluid tight connection between the housing and manifold. The configured housing may contain mechanical and/or optical features to ensure the alignment and the correct filter housing style is utilized in a specific manifold type. In general, correct classification of filter housing and filter media helps ensure proper configuration of the filtration and improvement of the filtration process. Examples filter classifications may include the designed maximum volume to be filtered, flow rate, pressure drop, filter media type, and housing type.

A variety of sensors 18 are described in detail herein. For example, as described, sensors 18 may take the form of indirect contact sensors that need not rely on any direct, physical contact with the filter media contained within filter housing 14, 16. In an example implementation, any of sensors 18 may be located outside, integrated within or otherwise affixed to the filter housing and outside the boundary defined by the surface of the filter media. In some implementations, for example, where a given housing is non-conductive or otherwise non-shielded, a sensor may be utilized, that generates an electromagnetic field for actively monitoring the remaining filter capacity of a filter media contained within the housing. For example, the sensor may produce a magnetic field that propagates through the non-conductive filter housing into the filter media and is sensed by an antenna coupled to the sensor. That is, a controller within the sensor determines the remaining capacity of the filter media by periodically generating an incident magnetic field into the filter media and measuring any change in one or more properties of the magnetic field caused by the changes in one or more characteristics (e.g., conductivity, dielectric strength, magnetic permeability, or the like) of the filter media over time as fluid flows through the filter. In general, filter capacity or efficacy refers to the remaining capability of the filter media to remove filtrate from the unfiltered fluid. The term remaining filter capacity or current capacity may be used to express the filter capacity at a point in time or at the time of a measurement. Filter capacity may be expressed in volume, time, percent of initial, mass, or number of particles or other units.

In other implementations of sensors 18 described herein, where a given housing is at least partially conductive, a sensor 18 may produce a radio frequency (RF) signal that is directed into the conductive filter housing by, for example, a port, a conductive window, a waveguide, direct electrical or electromagnetic coupling, or the like. The RF signal may be selected and generated by the sensor at a specific frequency such that the signal resonates within the resonant cavity defined by the internal boundaries of the conductive filter housing to produce a standing wave such that the standing wave propagates through the filter media. By periodically generating the RF signal, the controller within the sensor determines the remaining capacity of the filter media based on any change in one or more properties of the resonant cavity caused by the changes in one or more characteristics (e.g., conductivity, dielectric strength, magnetic permeability, or the like) of the filter media over time as fluid flows through the filter.

In other examples, any of sensors 18 may be direct contact sensor having physical electrical probes or contacts that are located at or inside a boundary defined by a surface of the filter media so as to be in direct contact with a filter media. That is, example implementations for sensors 18 are described herein that determine the remaining capacity of a filtration media by conductive contacts (e.g., probes) that provide electrical contact with the filter media. The probe may, for example, be integrated within or otherwise extend through the housing to contact the filter media.

In additional examples, sensing systems are described that provide automated identification for the filter media currently deployed within the filtration system 10. For example, in some implementations, non-contact identification bands may be incorporated within or otherwise affixed proximate housings 14, 16 containing the filter media. As described herein, the identification bands may be constructed so as to influence the magnetic sensing of the filter media by sensors 18 mounted on housings 14, 16. For example, the identification bands may be electrically conductive and/or magnetic so as to influence the electromagnetic field or resonant cavity sensed by antennas within sensors 18. Moreover, the bands may be geometrically or spatially arranged on housing 14, 16 so as to provide a unique identification of the filter media, such as when the filter media and the associated housing are together or individually inserted into the filtration system so as to pass through a sensing field created by the sensor. In this way, the identification bands may be utilized to provide an affirmative identification of the filter media. In some examples, the identification strip material, position, geometry, number of strips, or the like, may identify a filter family, a filter family subcategory, or the like.

The sensor, methods and sensor system described here have applicability to a wide range of applications that utilize filtration techniques. In one example, the sensor, methods, and system may be used to monitor filter media for a commercial water filtration system. The filtration system may contain an inlet, and outlet, a filter manifold with one or more filters, valves and plumbing to control the water flow, a power supply, additional sensor elements, and an electronic controller element to monitor the filtration process and may have a user interface, wireless connectivity, or a combination therefore. In a second example, the sensor, methods, and system may be used in a personal respirator to monitor the remaining filter capacity of the filter cartridges. The filter cartridges may be replaceable, and the sensor enables the user to determine if replacement of the cartridges is required. In other examples, the sensor may be employed in applications for fluid treatment in an appliance, heating ventilating and air conditioning (HVAC) system, natural gas filtration system, and personal air filtration.

Moreover, in addition (or in the alternative) to directly measuring filter capacity by monitoring the conductivity, dielectric, or permeability change of the filter media, the filter capacity can also be determined by measuring the change in conductivity, dielectric, or permeability of a surrogate material connected to the same fluid flow. The filter capacity can then be calculated based on a known relationship by a measured conductivity, dielectric, or permeability change of the surrogate material and the conductivity, dielectric, or permeability change of the filter media. The surrogate material can comprise of the same filter media, different filter media, non-filter media material, or any combination and could have a different form factor. One or more surrogate materials can be connected in series or in parallel. The surrogate material could provide a filtration function or no filtration function. The advantages of utilizing a surrogate material could be that the surrogate material has a higher sensitivity, lower sensitivity, enables a simpler system, improved stability, and reusable.

Figure 2:
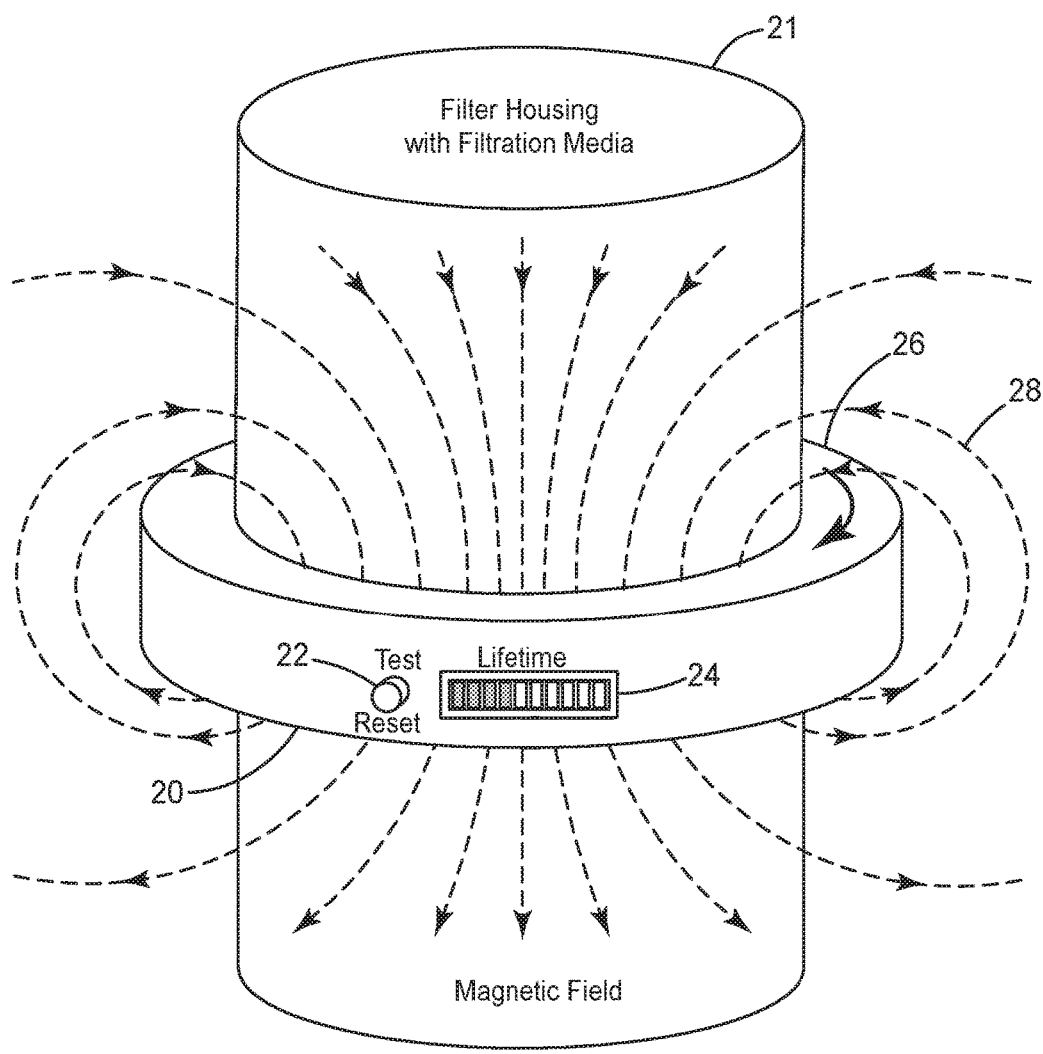
FIG. 2 is a schematic diagram illustrating an example indirect contact filter media sensor coupled to a filter housing.

FIG. 2 is a schematic diagram illustrating in further detail one example implementation of a sensor 20 coupled to an example filter housing 21. Sensor 20 may, for example, represent an example implementation of any of the sensors 18 of FIG. 1 coupled to any of housings 14, 16.

In this example implementation, filter housing 21 is a non-conductive housing containing filter media for the filtration of liquids or gases. In some examples, filter housing 14 may be a nonconductive material such as, for example, plastic, glass, porcelain, rubber, and the like. In the example of FIG. 2, filter housing 21 is cylindrical in shape. In other examples, filter housing 21 may be, for example, cuboidal, prismatic, conical, or the like. In some examples filter housing 21 may be configured to fit an existing water filtration system or subsystem. In other examples, nonconductive filter housing 21 may be configured to fit a new water filtration system or subsystem.

In the example of FIG. 2, a sensor 20 is positioned adjacent and external to filter housing 21. For example, sensor 20 may be configured to securely mount to the external surface of housing 21. In other examples, sensor 20 may be positioned external to the filter housing 21 and a gap may exist between an inner surface of the sensor 20 and an outer surface of the filter housing 21. In other examples, sensor 20 may be integrated within at least a portion of a surface of the filter housing 21 or even positioned at least partially inside the surface of the filter housing. Sensor 20 may be coupled to the filter housing 21 by bonding, for example, adhesive bonding, thermal bonding, laser bonding, or the like. In other examples, sensor 20 may be integrated into the material of the filter housing 21 to form a single, continuous filter system member. In other examples, the sensor 20 may be connected to the filter housing 21 by a mechanical connection by, for example, one or more fasteners, one or more clamps, one or more ridges or grooves in the surface of the filter housing 21 and sensor 20, or the like. In the example of FIG. 2, sensor 20 is positioned in a center of a longitudinal axis of the filter housing 21. In other examples, the sensor 20 may be positioned near an end of the filter housing 21. In other examples, the sensor 20 may be varyingly positioned between the end and the center of the filter housing 21.

In general, sensor 20 may incorporate user interface elements that provide visual and/or audible indications of the current capacity of filter 20. In the example of FIG. 2, a test/reset button 22 is located on an outer surface of the sensor 20. In other examples, the test/reset button 22 may be located on an outer surface of the filter housing 21. In other examples, the test/reset button 22 may not be located on either the sensor 20 or the filter housing 21. In some examples, the test/rest button 22 may be accompanied by text indicating, for example, "test" and/or "reset." In some examples, the test/reset button 22 may include an indicator light such as, for example, a light emitting diode, incandescent bulb, or the like. In some examples, the test/reset button 22 may be raised from the surface of the sensor 20. In other examples, the test/reset button 22 may be recessed from the surface of the sensor 20. In some examples, the test/reset button 22 may be configured to turn-on or turn-off a user interface 24. In some examples, the test/reset button 22 may be configured to reset the sensor 20 and user interface 24.

In the example of FIG. 2, a user interface element 24 includes, for example, a plurality of lights such as, for example, light emitting diodes, incandescent bulbs, or the like. In other examples, user interface 24 may include, for example, a graphical interface, a touch screen, or the like. In some examples, the indicator lights correspond to the filter media lifetime or capacity. For example, full filter media lifetime or capacity (e.g., a new filter) may be indicated by illumination of all indicator lights, whereas fewer lights may be illuminated as the filter media lifetime or capacity decreases. In some examples, the indicator lights may be one or more colors where designated colors and/or shading variations transition from full to empty capacity. In some examples, user interface 24 may be accompanied by text indicating, for example, "lifetime" or a series of percentages corresponding to the remaining filter media lifetime or capacity (e.g., 0%, 25%, 50%, 75%, and 100%).%). In some examples, the user interface 24 as a graphical interface may be represented as a pie chart (e.g., circular gauge), bar chart, or the like. In other examples, the measured remaining filter media lifetime or capacity may be displayed as a time interval (e.g., days) or a remaining volume of fluid that may be filtered to a predetermined purity or quality (e.g., gallons).

In some embodiments, sensor 20 includes an internal antenna (not shown) arranged to form conductive loops that encircle filter housing 21. An internal power source, such as a battery, and RF generator of sensor 20 drive an alternating electrical current 26 through the antenna so as to produce magnetic field 28. In general, magnetic field 28 propagates through at least a portion of the filter media contained within filter housing 21. As explained herein, the antenna (or plurality of antennas) of sensor 20 is an electronic component capable of generating near-field radiation that can be coupled with filtration media contained within housing 21. Examples include a single turn inductor, a multi-turn inductor, a two-dimensional conductive loop, a conductive loop with three dimensional features, and a capacitive element. The antenna may be non-resonant, resonant, or self-resonant.

In some embodiments, the filter media within housing 21 interacts with magnetic field 28 produced by sensor 20. For example, magnetic field 28 may interact with the filter media to induce eddy currents within the filter media. Creation of the field eddy currents in turn operate to reduce a strength of the magnetic field produced by the antenna of sensor 20. A controller within sensor 20 monitors characteristics of the antenna while producing magnetic field 28 and, based on those characteristics, determines qualities (strength, amplitude, phase, etc.) of the resultant magnetic field being produced. By monitoring changes in certain qualities of the magnetic field 28, the controller in turn detects changes in characteristics of the contained filter media, such as changes in filter media conductivity, dielectric constant, or magnetic permeability over time due to filtration of particulates.

The controller is electrically coupled to the antenna of the sensor and configured to drive an electric signal through the antenna to generate an electromagnetic signal configured to couple to at least a portion of the filter media via near-field coupling. The controller is configured to detect at least one characteristics of the antenna that is influenced by the filter media contained within the filter housing and, responsive to the detected characteristic, determine a current capacity of the filter media. Example characteristics of the antenna that may be influenced by the interaction between the filter media and the electromagnetic field so as to be detected by the controller include inductance, capacitance, reactance, impedance, equivalent series resistance, equivalent parallel resistance, quality factor, and resonant frequency of the antenna. In other words, the controller is configured to detect one or more characteristic of the antenna that is influenced by a material property of the filter media that changes over time during filtration of a fluid by the filter media. The material property of the filter media may be, for example, electrical conductivity, magnetic permeability, magnetic loss tangent, magnetic coercivity, magnetic saturation, dielectric constant, dielectric loss tangent, or dielectric strength of the filter media.

The design of the antenna, such as shape, size, and material selection, determines antenna properties, such as resonant frequency and radiation pattern. In one example, an ultrahigh frequency radio frequency identification (UHF RFID) antenna may be designed to efficiently radiate at 915 MHz to communicate with an UHF RFID reader operating at 915 MHz. Physical features of the antenna, such as internal loops and serpentine patterns, may be used to improve an antenna's radiation efficiency or directionality at a given frequency or modify the bandwidth of the antenna. In one example, one or more features of an UHF RFID antenna can be designed to be near-field coupled to filter media. The electromagnetic properties of the filter media, such as conductivity, dielectric constant, and permeability, may change the effect of the one or more properties of the antenna, such as resonant frequency, bandwidth, and efficiency. By monitoring this change in the antenna properties caused by this near-field interaction with the filtration media, the electromagnetic properties of a filter media can be monitored. Monitoring may be performed by an integrated circuit located on the antenna or by electronics located off the antenna, such in an external reader device.

In general, filtration media may be used in a broad range of applications involving filtration, separation, and purification of fluids (liquid and gas). Example media include, although not limited to, water filtration media, activated carbon, modified activated carbon, catalytic carbon, carbon, charcoal, titanium dioxide, non-wovens, electrets, air filtration media, water disinfectant removal media, particulate removal media, organic content removal, ion-exchange media, reverse osmosis media, iron removal media, semi-permeable membranes, molecular sieves, sand, magnets, screens, and barrier media. Example filtration techniques with which sensors described herein may be used include, as examples: absorption, chemisorption, physisorption, adsorption, precipitation, sublimation, ion-exchange, exclusion, extraction, electrophoresis, electrolysis, reverse osmosis, barrier membranes, sedimentation, distillation, and gas exchange. Table 1 illustrates example antenna characteristics that may be influenced by filter media properties such that changes to those antenna characteristics can be detected by the controller in accordance with sensors described herein:

TABLE 1

| | Change in Filter Media Property | | | | |
| --- | --- | --- | --- | --- | --- |
| Sensor Element | Electrical Conductivity | Magnetic Permeability | Magnetic-loss Tangent | Dielectric Constant | Dielectric-loss Tangent |
| Inductive Element (L, RL, Antenna) | Inductance, Reactance, Resistance, Q-Factor | Inductance, Reactance, Resistance, Q-Factor | Resistance, Q-Factor | | |

TABLE 1-continued

| | Change in Filter Media Property | | | | |
|---|---|---|---|---|---|
| Sensor Element | Electrical Conductivity | Magnetic Permeability | Magnetic-loss Tangent | Dielectric Constant | Dielectric-loss Tangent |
| Capacitance Element (C, RC, Antenna) | | | | Capacitance, Reactance, Resistance, Q-Factor | Resistance, Q-Factor |
| Resonant Circuit (LC, LCR, Antenna, Resonant Antenna) | Inductance, Reactance, Resistance, Q-Factor, Resonant Frequency | Inductance, Reactance, Resistance, Q-Factor, Resonant Frequency | Resistance, Q-Factor | Capacitance, Reactance, Resistance, Q-Factor, Resonant Frequency | Resistance, Q-Factor |

As one example, in activated carbon water filtration, sensor 20 may be configured to detect changes to the conductivity of a media filter over the lifetime of the filter. As an example, water filtration systems are often deployed for dechlorination to remove previously added chlorine. That is, water disinfection is typically accomplished by the addition of sodium hypochlorite solution (NaOCl), solid calcium hypochlorite (Ca(OCl)$_2$), chlorine gas (Cl$_2$), or monochloramine (NH$_2$Cl). Chlorine dissociates in the presence of water for form hypochlorite (OCl—) and hypochlorous acid (HOCl), as shown by the following reactions:

Cl$_2$(g)+H$_2$O(l)⇌HOCl+H$^+$+Cl$^-$

HOCl⇌H$^+$+OCl$^-$

Water filtration systems are often deployed for subsequent dechlorination to remove the chlorine because the presence of excess chlorine in water produces an undesirable taste, odor, membrane degradation in reverse osmosis and nano-filtration systems, and the like. Flowing water through a highly porous activated carbon filter aids in dechlorination by reducing chlorine to chloride through, for example, oxidation of the activated carbon filter media. Representative chemical equations are shown below:

C(s)+HOCl(aq.)⇌CO*(s)+H$^+$+Cl$^-$

C(s)+OCl$^-$(aq.)⇌CO*(s)+Cl$^-$ where CO* represent an oxidative carbon site on the activated carbon filter media. In this way, chlorine is reduced to chloride, which is safe for human consumption, reduces undesirable taste and order, and is safe for additional water conditioning methods.

As explained herein, responsive to the dechlorination process, the electrical conductivity of an activated carbon filter decreases over time. Further, surface oxidation over time results in a significant decrease in the electrical conductivity of the activated carbon filter. Moreover, any change in conductivity of the media filter in turn influences magnetic field 28 generated by sensor 20, which is detected by sensor 20. By periodically producing and sensing the resultant magnetic field 28, sensor 20 is able to measure the conductivity decrease of the activated carbon filter during dechlorination and, therefore, determine the percentage of the oxidized surface sites and the remaining lifetime or capacity of the filter. The measured remaining filter capacity is displayed on user interface 24, which may represent a percentage of the total capacity, a time interval such as days, or a volume (measurement) of water. Alternatively, sensor 20 may communicate the results to a central monitor, such as monitor 12 of FIG. 1, for centralized reporting and alerting.

In this example scenario, sensor 20 may predict and alert an upcoming chlorine breakthrough for an activated carbon filter media, which is characterized as when a filtrate chlorine concentration surpasses a threshold chlorine concentration. In this way, sensor 20 may facilitate active determination and early notification of the chlorine breakthrough.

Figure 3:
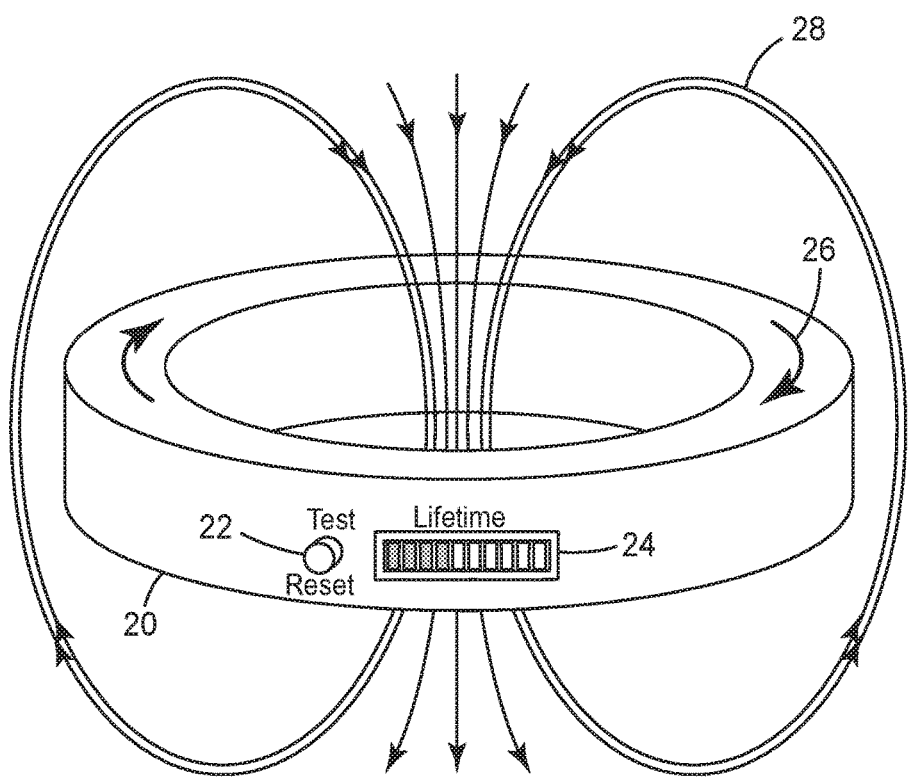
FIG. 3 is a schematic diagram illustrating in further detail an electromagnetic field created by an example indirect contact filter media sensor

FIG. 3 is a schematic diagram illustrating in further detail an example electromagnetic field created by the example indirect contact filter sensor 20 of FIG. 2. In the example of FIG. 3, the internal antenna (not shown) of sensor 20 forms a magnetic field 28 that travels through at least a portion of the interior space defined by the annular shape of the sensor 20. In some examples, a conductive material in the filter media generates an eddy currents (not shown) in the presence of a first magnetic field 28. The eddy currents in the filter media results in the creation of a second magnetic field (not shown) that opposes the first magnetic field 28. The second magnetic field in turn lowers the overall strength of the magnetic field 28. In some examples, the magnitude of the eddy currents and the second magnetic field depend on the electrical conductivity of the filter media. In this way, the finite electrical conductivity of the filter media represents an energy loss mechanism detected by sensor 20. In some examples, the energy loss mechanism may be used to determine the conductivity or conductivity change of the filter media by monitoring the electronic characteristics of the antenna such as, for example, inductance, capacitance, resonant frequency, quality factor, equivalent series resistance, or equivalent parallel resistance. In other examples, the antenna may be configured to be a resonant circuit. In this way, the conductivity or conductivity change of the filter media is determined by monitoring, for example, inductance, capacitance, resonant frequency, quality factor, equivalent series resistance, equivalent parallel resistance, or the like. For example, the resonant frequency (f$_0$) of the non-contact sensor can be determined from the inductance (L) and the capacitance (C):

$$f_o = \frac{1}{2\pi\sqrt{LC}}.$$

The quality factor (Q) of the resonant circuit is determined by the series reactance (X$_s$) and the series resistance (R$_s$) at resonance:

$$Q = \frac{X_s}{R_s}.$$

At resonance, the series capacitance reactance ($X_{C,S}$) and the series inductive reactance ($X_{L,S}$) are equal:

$$X_{c,s} = \frac{1}{2\pi f_o C}$$

$$X_{L,s} = 2\pi f_o L.$$

A change in inductance or capacitance will change the $f_0$ of the sensor and change the parallel resistance ($R_p$) of the sensor. In the case where the resonant frequency change is caused by a change in capacitance, the corrected parallel resistance of the sensor is given in the equation:

$$R_p = R_{p,o} \left( \left( \frac{\Delta f + f_o}{f_o} \right)^2 \right).$$

In the case where the resonant frequency change is caused by a change in inductance, the corrected parallel resistance of the sensor is given in the equation:

$$R_p = R_{p,o} \left( \left( \frac{f_o}{\Delta f + f_o} \right)^2 \right).$$

In some examples, an impedance evaluation module (not shown) may be used to monitor a characteristic of an antenna, for example, inductance, capacitance, resonant frequency, quality factor, equivalent series resistance, equivalent parallel resistance, or the like to determine one or more parameters of the filter media such as, for example, conductivity, dielectric strength, magnetic permeability, and the like. In this way, for example, monitoring the inductance, capacitance, resonant frequency, quality factor, equivalent series resistance, equivalent parallel resistance, or the like, may provide real-time indication of filter media lifetime or capacity, which is advantageous over methods that estimate filter lifetime or capacity based on duration of operation or total fluid volume filtered.

Sensor 20 includes one or more sensor elements such as, for example, an antenna, an inductor-capacitor (LC) circuit, an inductor-capacitor-resistor circuit (LCR), an inductor-resistor (LR) circuit, a capacitor-resistor (CR) circuit near-field coupled to filtration media. In some example implementations, sensor 20 may include additional sensor elements designed to measure additional system parameters that are used to compensate for sensor drift and environmental conditions that affect the sensor properties. Example additional parameters that may be measured and used to adjust sensor measurements include flow rate, inlet pressure, outlet pressure, pressure drop, fluid temperature, ambient temperature, sensor temperature, electronics temperature, contaminate type sensor, and time. For example, compensation of the temperature dependence of the parallel resistance of the antenna element is caused by the temperature dependence of resistivity of the conductor that comprises the antenna, as such the parallel resistance ($R_{p,T}$) of the can be calculated by:

$$R_{p,T} = \frac{R_{p,o}}{(1 + \alpha(T_a - T_{a,o}))} = \frac{R_{p,o}}{(1 + \alpha(\Delta T_a))}$$

where $R_{p,o}$ is the parallel resistance of the antenna at $T=T_o$, $\alpha$ is the temperature coefficient of resistivity of the antenna, $T_a$ is the temperature of the antenna, $T_{a,o}$ is the reference temperature of the antenna, and $\Delta T_a$ is the change in temperature of the antenna. Whereas the filtration media, for example, has a temperature dependence resistivity ($R_{f,T}$) that can be calculated by:

$$R_{f,T} = \frac{R_{f,o}}{(1 + \beta(T_w - T_{w,o}))} = \frac{R_{f,o}}{(1 + \beta(\Delta T_w))}$$

where $R_{f,o}$ is the resistance of the filtration media at $T=T_o$, $\beta$ is the temperature coefficient of resistivity of the filtration media, $T_w$ is the temperature of the water, $T_{w,o}$ is the reference temperature of the water, $\Delta T_w$ is the change in temperature of the water.

Examples—Filter Capacity & Conductivity Change

As such, in various examples, filter capacity can be determined through measuring conductivity of the filter media during filtration. To determine filter capacity, the filter media is disposed in the near-field of a resonant antenna. The equivalent parallel resistance of the resonant antenna at resonance is measured during the filtration process. By measuring the equivalent parallel resistance of the resonant antenna at resonance, the coupled equivalent resistance of the filter media can be monitored. Filter capacity can be determined based on a predetermined correlation between coupled equivalent resistance of the filter media and filter capacity.

In another example, filter media is disposed in the near-field of a non-resonant loop antenna. The equivalent series resistance of the non-resonant loop antenna is measured during the filtration process. By measuring the equivalent series resistance of the non-resonant antenna, the coupled equivalent resistance of the filter media can be measured. The measured coupled equivalent resistance is used to determine the filter capacity based on a predetermined correlation with the filter capacity.

In another example, filter media is disposed in the near-field of a capacitance element. The equivalent parallel resistance of the capacitance element is measured during the filtration process. By measuring the change in equivalent parallel resistance of capacitance element, the coupled equivalent resistance of the filter media can be measured. The measured equivalent resistance is used to determine the filter capacity based on a predetermined correlation between the coupled equivalent resistance of the filter media and filter capacity.

The sensitivity of the sensor may be defined as the sensor change caused by a unit change in the object to be sensed. For the examples described above, sensor sensitivity can be improved by increasing the parallel resistance of the antenna or capacitance element in the absence of the filter media. Construction of a sensor element with a high parallel resistance in the absence of the filter media may require high cost materials, high cost component design/construction, and increased sensor size. Additionally, electronics suitable to read a sensor with a high parallel resistance may require high cost electronic components and advanced algorithms. In a practical system design, the system designer may have to consider the interdependency between sensor sensitivity and sensor cost. In one embodiment, the parallel resistance of the sensor is between 100Ω and 10 kΩ. In a second embodiment, parallel resistance of the sensor greater than the coupled resistance of the filter. In a third embodiment, the parallel resistance of the sensor is greater than 0.001 times the coupled resistance of the filter.

Sensitivity may be improved by achieving a higher quality factor. For the same reasons described above, design of a sensor with a high quality factor may be impractical. In one embodiment, the quality-factor of the sensor is higher than 10 and lower than 1000. In a second embodiment, the quality factor of the sensor is between 50 and 200.

In addition, increasing the operational frequency of an antenna element may lead to higher sensor sensitivity. As the operational frequency for a given antenna increases, the reactance typically has a larger increase compared to the resistance, which leads to a higher quality factor and parallel resistance of the antenna. In some applications, increasing the operational frequencies may be impractical as the required electronics may be of a higher cost, consume additional power, and exceed governmental emission limitations. In one embodiment, the operational frequency is between 1-30 MHz. In a second embodiment, the operational frequency resides within one or more industrial, scientific and medical (ISM) radio bands.

Sensor sensitivity can be improved by increasing the magnitude of the near-field coupling between the antenna and the filter media. The magnitude of the near-field coupling coefficient can range from 1 (perfect coupling) to 0 (no coupling). In practical sensor design, realizing high coupling is limited by system geometrical constraints, such as the separation of the antenna and filter media caused by the presence of the filter housing or the presence of a fluid. In one embodiment, the coupling coefficient is higher than 0.1.

In some applications, the sensor may be required to only detect when the filter media capacity falls below a threshold. In this application, a sensor system with low sensitivity may be acceptable. In some applications, the sensor may be required to have a high resolution of the filter media capacity during the entire lifetime of the filter. In this application, a sensor system with high sensitivity may be required.

Examples—Filter Capacity & Magnetic Change

In one example, filter capacity is determined by measuring the magnetic permeability of the filter media during filtration. To determine filter capacity, the filter media is disposed in the near-field of a resonant antenna. The resonant frequency of the resonant antenna is measured during the filtration process. By measuring the resonant frequency of the antenna, the magnetic permeability of the filter media can be monitored. The measured magnetic permeability is used to determine the filter capacity based on a predetermined correlation between magnetic permeability and filter capacity.

In a second example, filter media is disposed in the near-field of a non-resonant loop antenna. The inductance of the non-resonant loop antenna is measured during the filtration process. By measuring the inductance of the non-resonant antenna, the magnetic permeability of the filter media can be measured. The measured permeability is used to determine the filter capacity based on a predetermined correlation between filter media permeability and filter capacity.

In a third example, the filter media is disposed in the near-field of a non-resonant loop antenna. The equivalent parallel resistance of the non-resonant loop antenna is measured during the filtration process. By measuring the change in equivalent parallel resistance of the non-resonant antenna, the magnetic loss tangent of the filter media can be measured. The measured loss is used to determine the filter capacity based on a predetermined correlation between magnetic loss tangent and filter capacity.

Examples—Filter Capacity & Dielectric Change

In one example, filter capacity is determined by measuring the dielectric constant of the filter media during filtration. To determine filter capacity, the filter media is disposed in the near-field of a capacitor element. The capacitance of the capacitor element is measured during the filtration process. By measuring the capacitance of the capacitor element, the dielectric constant of the filter media can be measured. The measured dielectric constant is used to determine the filter capacity based on a predetermined correlation between dielectric constant and filter capacity.

In a second example, filter media is disposed in the near-field of a capacitor element. The equivalent parallel resistance of the capacitor element is measured during the filtration process. By measuring the change in equivalent parallel resistance of the capacitor element, the dielectric loss tangent of the filter media can be measured. The measured loss is used to determine the filter capacity based on a predetermined correlation between dielectric loss tangent and filter capacity.

Examples—Conductivity, Dielectric, and Permeability Changes During Filtration

In one example, chlorine from a municipal water source is filtered by a catalytic reduction process of an activated carbon filter block. During filtration, surface oxidation reduces the number of catalytic sites on the carbon block and decreases the capability of the carbon block to filter chlorine. Oxidation of the activated carbon block results in a decreased electrical conductivity of the filter block. Based on this mechanism, filter capacity may be correlated to the conductivity of the filter block.

In second, a non-conductive filter membrane is designed to filter electrically conductive particles dispersed in a liquid. During filtration, conductive particles captured by the filtration media causes the effective resistance of the filter to decrease. As more conductive particles are captured by the filter, the capacity of the filter to capture additional particles decreases. Based on this mechanism, filter capacity may be correlated to the conductivity of the filter membrane.

In a third example, iron contained within water derived from a residential well water source is filtered with a non-magnetic filter block. During filtration, iron particles captured by the filtration media cause the effective permeability of filter to increase. As more iron particles are captured by the filter, the capability of the filter decreases. Based on this mechanism, filter capacity may be correlated to magnetic permeability of the filter.

In a fourth example, volatile organic content in filtered by granular carbon attached to a personal respirator device. During filtration, adsorption of the organic content of the carbon surface causes the dielectric constant of the carbon to increase. The dielectric constant increases because the organic content has a higher dielectric constant compared to the displaced air. As organic content adsorbs to the surface and prevents additional organic contact adsorption, the filter capability decreases. Based on this mechanism, the filter capacity may be correlated to the dielectric constant of the filter.

In fifth example, air particles are filtered by a non-woven electret filter in a residential furnace. During filtration, particle loading of the filter causes the dielectric constant of the filter to increase. As more particles are captured by the filter, the filter capability to capture additional particles decreases. Based on this mechanism, filter capacity may be correlated to the dielectric constant of the filter.

Figure 4:
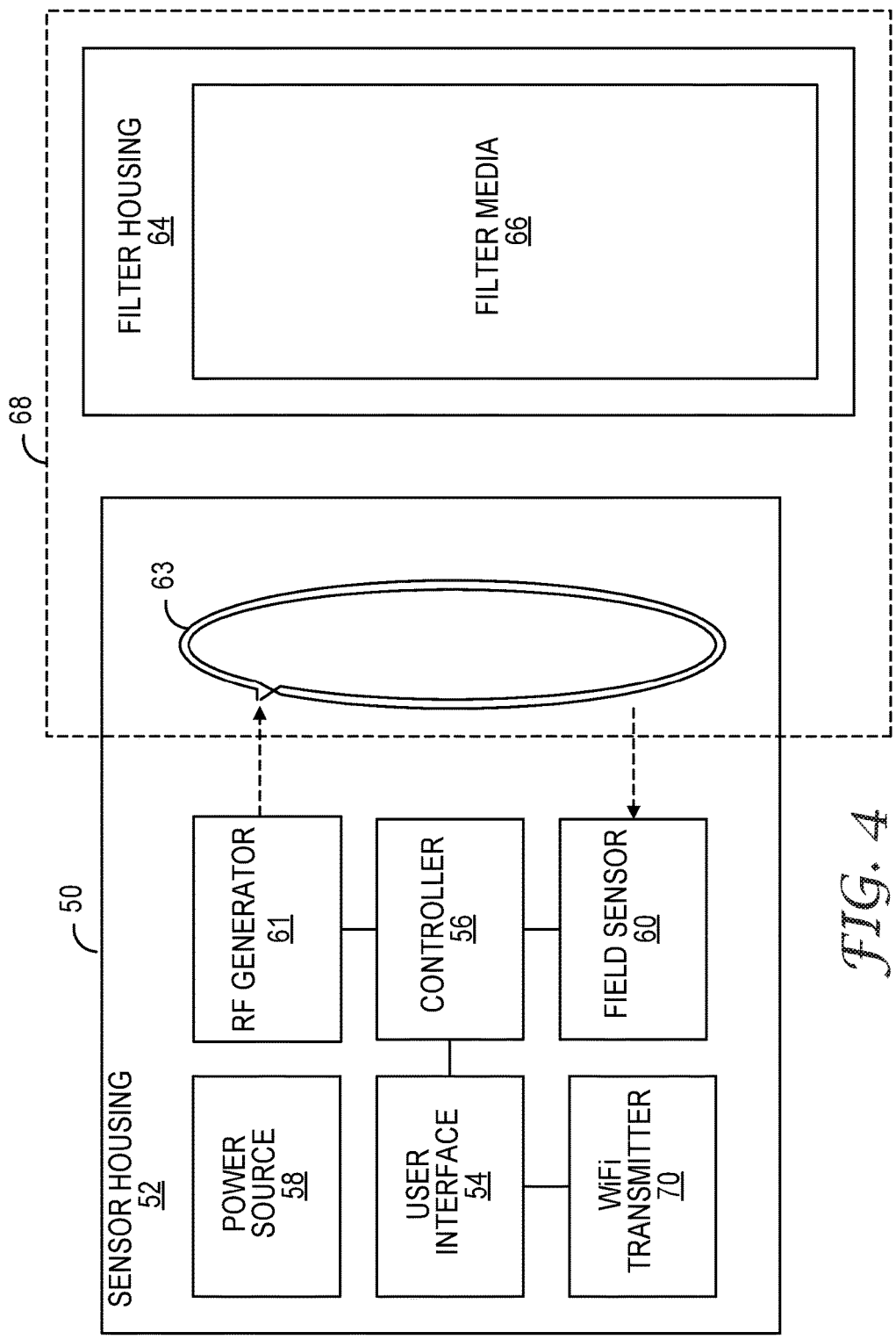
FIG. 4 is a block diagram illustrating in further detail an example indirect contact filter media sensor configured to sense remaining capacity of a filter media contained within a filter housing.
Figure 5K:
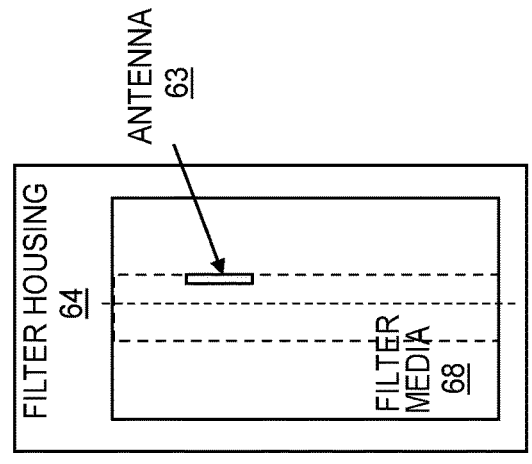
Figure 5J:
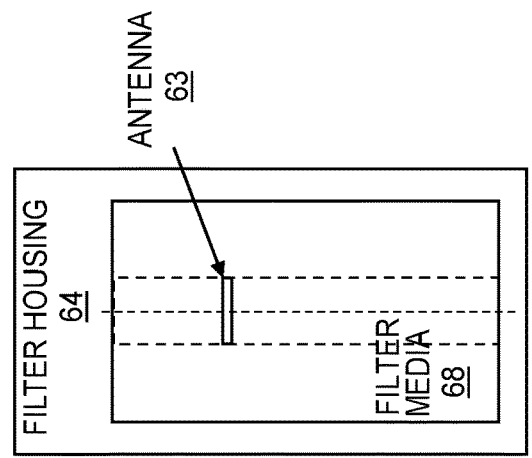

FIG. 4 is a block diagram illustrating an example sensor system in which a sensor 50 is configured to sense one or more properties of a filter media contained within filter housing 64. Sensor 50 may, for example, represent an example implementation of any of the sensors described herein, such as sensors 18 of FIG. 1 and sensors 18 of FIGS. 2-3.

In the example of FIG. 4, sensor 50 includes sensor housing 52, user interface 54, controller 56, power source 58, field sensor 60, RF generator 61, and antenna 63. In other examples, sensor 50 may include additional modules or hardware units, or may include fewer modules or hardware units. In the example of FIG. 4, sensor 50 is positioned proximate filter housing 64 and filter media 66, such that sensor 50 is in electromagnetic communication 68 with filter housing 64 and filter media 66.

In the example of FIG. 4, sensor housing 52 houses user interface 54, controller 56, power source 58, field sensor 60, RF generator 61 and antenna 63 and is annular shaped to encompass (e.g., partially or fully encircle) a filter housing. For example, sensor housing 52 may be annular shaped to fully encircle a filter housing as shown in FIGS. 1-3 in which sensors 18, 20 fully encircle housing filter housings 14, 16, 21. In this way, antenna 63 internal to sensor housing 52 may include one or more electrically conductive loops that wind within the annular sensor housing so as to encircle filter media once sensor 50 is affixed to a sensor housing.

In the example of FIG. 4, antenna 63 transmits and receives electromagnetic signals 68 into and from filter media 66 located inside nonconductive filter housing 64. Antenna 63 of FIG. 4 interfaces with controller 56, which receives electrical power from power source 58. In some examples, power source 58 may include a battery source or another internal power source. In other examples, a power source 58 may be an external power supply such as, for example, local power supplies, alternative current to direct current converters, or the like. In some examples, the power source 58 may harvest power from an external source such as light or an RF energy.

Responsive to configuration from controller 56, RF generator 61 generates an RF signal that, in one example, drives antenna 63 to create the electromagnetic field. Responsive to commands from controller 56, RF generator 61 may, for example, generate an RF signal as one or more sinusoidal waves, a square wave, a discontinuous signal or the like. RF generator 61 may, as described herein, control a shape, phase, e.g., phase shift, and/or an amplitude of the RF signal.

For example, in some example implementations controller 56 is configured to direct RF generator 61 to sweep the excitation frequency of antenna 63 to measure the frequency response of the antenna. The frequency sweep of the sensor may be executed as controllable discrete linear steps, log steps, or other. The size of the steps is one factor in determining sensor frequency resolution and measurement refresh rate. For a 1 MHz sweep range with 1 KHz linear steps and each step consuming 100 us, the total sweep time would be 1000*100 us=100 ms. For the same system with 10 kHz steps, the total sweep time would be 100*100 us=10 ms. The decreased sweep time with 10 kHz steps will decrease the frequency resolution of the measurement. In some examples, signal processing methods such as interpolation and regression may be used to increase the frequency resolution of the measurement.

In some applications, the measured signal detected by sensor 50 may be small resulting in a noisy measurement. One method to increase the signal strength is to control the amplitude of the generated signal. In one example, the amplitude of signal is increased to fully utilize the dynamic range of the detection circuit.

In one example, the quality-factor of a resonant antenna can be monitored by a ring-down method. This method includes exciting the resonant antenna, removing the excitation source, and measuring the signal of the resonant antenna as the signal decays. The decay rate is inversely proportional to the quality factor. In this example, controlling or having knowledge of the phase, may allow the excitation source to be terminated at zero-current and minimize switching spikes caused by the excitation source.

As an example, the waveform of the output frequency produced by RF generator 61 could include square wave, sine wave, triangle wave, saw tooth wave, sum of sinusoids, or the like. A square wave, sine wave, triangle wave and saw tooth wave are commonly generated waveforms.

In some example implementations, sensor 50 directs the RF signal into filter housing 64 itself by, for example, a port, a radio frequency transparent window, a waveguide, direct electrical or electromagnetic coupling, or the like. Controller 56 may configure RF generator 61 to generate the RF signal at a specific frequency such that the signal resonates within the resonant cavity defined by the internal boundaries of the filter housing 64 to produce a standing wave such that the standing wave propagates through the filter media 66. Examples of controller 56 include an embedded microcontroller, an Application Specific Integrated Circuit (ASIC), a field programmable gate array (FPGA), a digital signal processor (DSP), a general purposes embedded microprocessor, a logic gate, or the like, or combinations thereof.

In the example of FIG. 4, controller 56 interfaces with field sensor 60 to measure properties of the electromagnetic field generated by antenna 63. In one example, field sensor 60 is an inductance-to-digital converter that operates in closed-loop fashion with RF generator 61 to monitor the energy dissipated by antenna 63 and output a digital value indicative of a magnitude of the electromagnetic field currently being produced by the antenna. As examples, field sensor 60 may output one or more signals indicative of a variety of properties of antenna 63 when being driven to create the electromagnetic field, such as inductance, capacitance, resonant frequency, quality factor, equivalent series resistance, or equivalent parallel resistance. In some examples, field sensor 60 and RF generator 61 may be implemented in a common integrated circuit or component, such as an LDC 1000 available from Texas Instruments™ of Dallas, Tex. Based on the output of field sensor 60, as described herein, controller 56 computes parameters indicative of characteristics of the conductivity, dielectric strength, magnetic permeability, or the like of filter media 66.

Controller 56 operates user interface 54 to display or transmit indicators representative of filter media 66 conductivity, dielectric strength, magnetic permeability, or the like. In some examples, user interface 54 may include, for example, a plurality of lights such as, for example, light emitting diodes, incandescent bulbs, or the like. In other examples, user interface may include, for example, a graphical interface, a touch screen, or the like. In some examples, the indicator lights correspond to the lifetime or capacity of the filter media based upon the filter media 66 conductivity, dielectric strength, magnetic permeability, or the like. In some examples, user interface 54 may be configured to transmit signals via a WiFi or other radio transmitter 70. In some examples, WiFi transmitter 70 may transmit the determined characteristics of media filter 66, such as remaining capacity, by radio frequency communication, wireless local area network (WLAN) connection, or the like. In other examples, WiFi transmitter 70 may transmit raw filter media 66 data, such as conductivity, dielectric strength, magnetic permeability, or the like for remote analysis. In one example, the controller comprises of at least one of the following components: read-only memory (ROM), random-access memory (RAM), processor, analog peripheral, and digital peripheral. In some instances, the controller may be an integrated circuit (IC), such as an application specific integrated circuit (ASIC), field programmable logic array (FPGA), embedded microcontroller, embedded microprocessor, or logic gate. In other instances, the controller can be an amalgamation of several circuits or several integrated circuits interacting together with inputs and outputs. This controller utilizes its components to form decisions and measurements of the present filter capacity. These decisions can be made via signal processing techniques, algorithms, and/or data management. Measurements can be either analog measurements from at least one analog to digital converter (ADC), digital measurements from at least one digital interface, or wireless measurement from at least one wireless interface.

In some instances, the controller will need to provide feedback to the user regarding the state of the sensor. One feedback mechanism is digital communication. This form of communication could be but is not limited to unidirectional or bidirectional data flow between the sensor controller and an external entity that is capable of the digital communication. An example of unidirectional digital communication is universal asynchronous receiver/transmitter (UART), where only one data line connects the controller of the sensor to external entity capable of receiving UART communication. A few examples of bidirectional digital communication from the controller of the sensor could be serial peripheral interface (SPI), inter-integrated circuit (I2C), or UART communication. The digital communication can pass data from the sensor controller by sending raw measurement data or processed information. There are advantages to both data exchanges, as refined information can be sent more quickly, whereas raw measurement data can be sent to another entity for processing.

In some instances, the controller 56 provides feedback to an entity that does not accept digital or wireless communication. One of such other feedback mechanisms is through analog communication. This form of communication may be but is not limited to at least one digital to analog converter (DAC) output. In some instances, using an analog output can be easier and simpler to transfer data or information from the sensor controller. When a DAC output is synchronized by a time base for periodic sampling intervals, one can transfer data as an analog signal. Analog signals may be but are not limited to sinusoids, square waves, triangle waves, saw tooth waves, and direct current (DC) level signals.

In some examples, a wired connection is not desired or possible for communication. In such instances, a wireless communication network can be implemented. A wireless communication network may include at least one sensor controller, and can be interfaced to a user interface (UI) entity, other processing entity, or other sensor controller. This form of communication may be but is not limited to at least one Wi-Fi network, Bluetooth connection, or ZigBee network. Communication can be unidirectional or bidirectional. The hardware of the communication may modulate the data transfer in a particular scheme such as frequency shift keying (FSK). When the controller needs to release data or information, it can send it over a wireless channel to another entity for read out or processing.

In many instances, the sensor system will alert or alarm the user. Such events, such as the present filter capacity reaching a certain threshold, may be communicated to the user through visible, audible, or physical methods. Such examples of an alert system include but are not limited to a DAC output, a function generator, a display, a speaker, a buzzer, or a haptic feedback mechanism. These user interfaces can be in communication with the sensor controller via analog, digital, or wireless communication.

In general, the forms of communication described above (digital, analog, and wireless), typically utilize a time based protocol generated by at least one timer circuit in the controller to maintain proper timing between data transfer sampling or signal clocking. A timer circuit could be a software timer inside of the controller, an analog circuit with time constants from charging/discharging, a software- or hardware-defined counter, or a clock signal from a communication channel. The time based protocol may also allow for the periodic sampling of the sensor to obtain measurements regarding the filter media.

FIGS. 5A-5K are block diagrams illustrating example arrangements of sensing systems described herein and, in particular, illustrate example relative positions and orientations between antenna 63 and filter media 68. In general, sensor systems as described herein can consist of any orientation between antenna 63 and filter media 68 capable of causing at least a portion of a generated magnetic field of antenna 63 to interact with the filter media 68. When at least a portion of the magnetic field of antenna 63 is incident on the filtration media 68, the filter media 68 and antenna 63 are in near-field electromagnetic interaction, also referred to herein as near-field coupled, inductively coupled, magnetically coupled, and electromagnetically coupled. Several example embodiments are shown in FIGS. 5A-5K. In these embodiments, antenna 63 is depicted as the plane where an antenna resides and the antenna is positioned in a variety of orientations relative to the filter media. Moreover, as shown in the examples, antenna 63 may be exterior to filter housing 64, exterior and proximal to the filter media, or disposed within portions of the filter media. Antenna 63 can be a conductive loop with different parameters such as number of turns, diameter, and conductor thickness. Although not shown, antenna 63 may not be limited to a planar antenna but can have a third dimension such as a coil inductor or antenna turns with different normal directions.

Figure 6A:
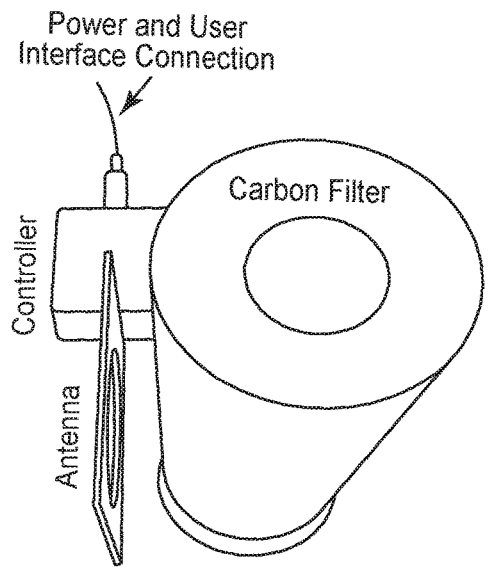
FIGS. 6A-6D illustrate configurations of additional experiments that were performed in a sensor system in which the antenna was positioned and oriented exterior to a filter housing.
Figure 6B:
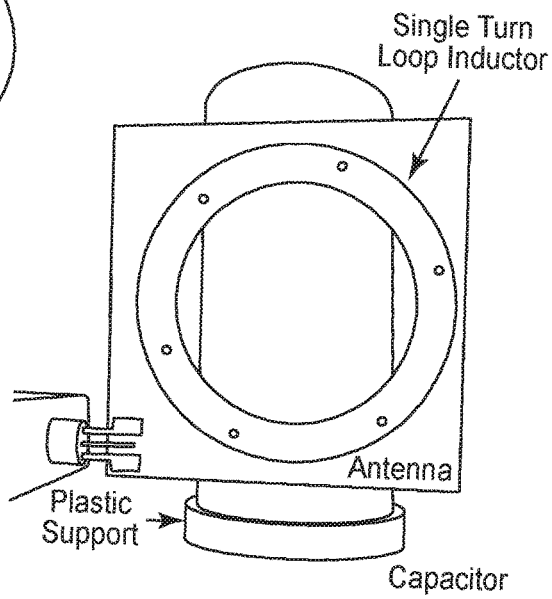
Figure 6C:
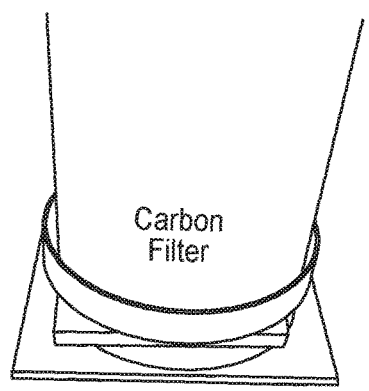
Figure 6D:
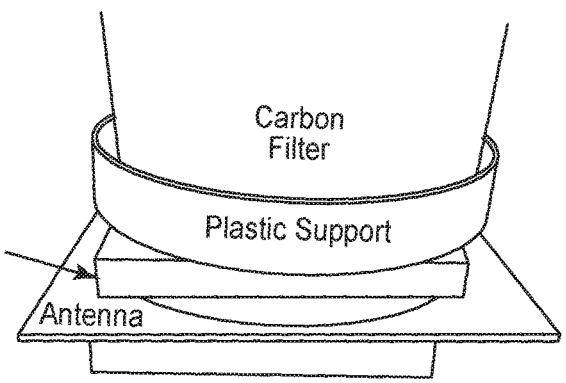

Experiments were performed in a sensor system in which the antenna was positioned and oriented exterior to a filter housing and relative to a filter media as shown in FIGS. 5B and 5D. Configurations of the experiment are shown in FIGS. 6A-6B (antenna positioned along a long axis of the filter media and proximate to the filter media) and FIGS. 6C-6D (antenna positioned below the filter media). In the experiments, an activated carbon filter block filtered water having 2 ppm of chlorine at a constant flow rate of 2 gallons per minute. The following antenna design was used:

Material: Cu on 0.062" FR 4
Copper (Cu) Thickness: 35 micrometers
Turns: 1
Inner Diameter: 4.83 cm (1.90")
Outer Diameter: 6.10 cm (2.40")
Resonant Frequency: 23.1 MHz Quality Factor: 140

The following filter block was used in the experiment:
Material: Activated Carbon (Coconut)
Inner Diameter: 5.72 cm (2.25")
Outer Diameter: 2.54 cm (1.00")

The following table shows the results of the experiment. As shown below, in both antenna orientations a controller coupled to the antenna was able to detect influences on the equivalent resistance of the resonant antenna due to changes in conductivity of the media filter in response to filtration of chlorine.

| Chlorine Breakthrough 2.0 ppm Chlorine Challenge (% passed) | Coupled Equivalent Resistance Resonant Antenna - Proximal 0.5" Separation (kΩ) | Coupled Equivalent Resistance Resonant Antenna - Below 0.25" Separation (kΩ) |
|---|---|---|
| 0 | 5.11 | 1.96 |
| 25% | 121.8 | 45.93 |

Figure 7A:
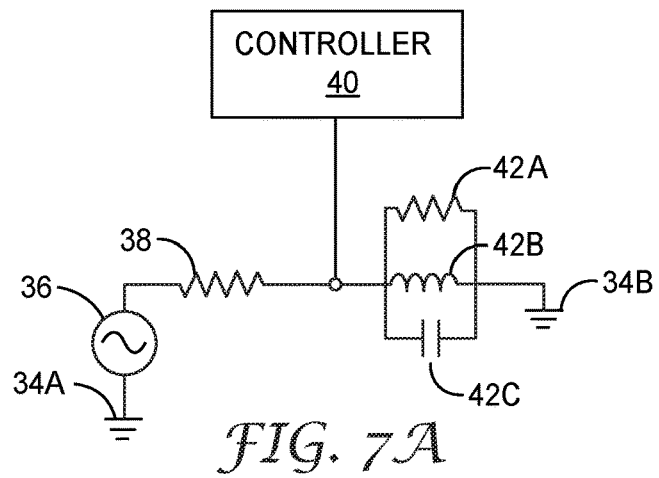
FIGS. 7A, 7B and 7C are circuit diagrams that logically illustrate the electrical characteristics of an antenna of sensor 20 from FIGS. 2 and 3 during operation.
Figure 7B:
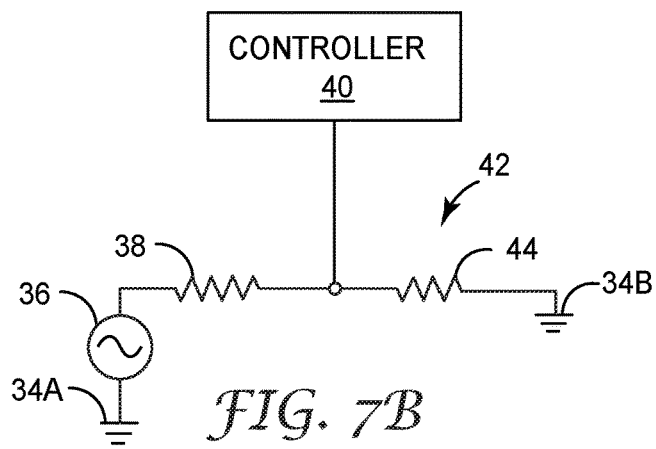
Figure 7C:
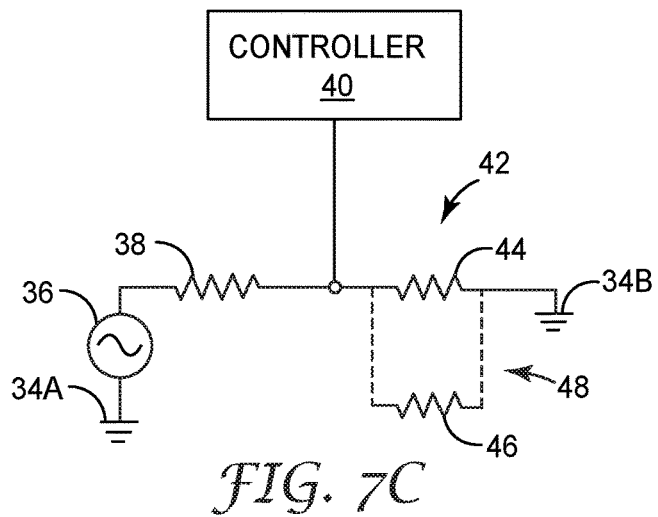

FIGS. 7A, 7B and 7C are circuit diagrams that logically illustrate the electrical characteristics of an antenna of sensor 20 from FIGS. 2 and 3 during operation. In particular, FIG. 7A illustrates a logical diagram of sensor 20 including ground 34A and 34B, alternating current generator 36, resistor 38, controller 40, resistor 42A, inductor 42B, and capacitor 42C. In the example of FIG. 7A, resistor 42A, inductor 42B, and capacitor 42C collectively represent "antenna 42."

FIG. 7B provides a logical representation of the electrical characteristics of the antenna when the alternating current generator 36 generates an RF signal at a resonant frequency of antenna 42. In this mode of operation, the effects on inductor 42B and capacitor 42C, as illustrated in FIG. 5A, negate one another during operation at the resonant frequency of antenna 42 so as to logically illustrate antenna 42 as resistor 44.

FIG. 7C provides a logical representation of the electrical characteristics of the antennae when antennae 42 operating at a resonant frequency couples to a proximate conductive filter media so as to change the effective resistance of antenna 42. In some examples, filter media resistor 46 is associated with a resistance of the filter media. In other examples, filter media resistor 46 is associated with a resistance of a non-filtering media. For example, a nonconductive filter housing containing a conductive filter media may couple to antenna 42. In the example of FIG. 7C, the antenna resistor 44 and filter media resistor 46 are coupled by an electromagnetic communication 48. In such an example, the effective resistance is given by $$R_F = \frac{R_A R_{AF}}{R_A - R_{AF}}$$

where $R_A$ is the resistance of the antenna operating at the resonant frequency (e.g. antenna resistor 44), $R_F$ is the couple resistance of the filter media (e.g. filter media resistor 46), and $R_{AF}$ is the resistance of the antenna when coupled to the filter media. Controller 40 of the sensor computes the filter resistance ($R_F$). In this way, characteristics of an antenna may be used to determine the resistance of a filter media.

In the example of water filtration, the conductivity of an activated carbon filter media in dechlorination decreases as the surface of the activated carbon is oxidized, as explained above. The rate of conversion of chlorine to chloride at oxidized sites on the carbon filter media may be slower than the rate of conversion of chlorine to chloride at non-oxidized sites on the activated carbon filter media. In this way, monitoring the change in conductivity of an activated carbon filter media provides an indication of the oxidation state of the activated carbon filter media, which controller 40 in turn uses to determine an estimated lifetime or remaining capacity of the activated carbon filter media.

Figure 8A:
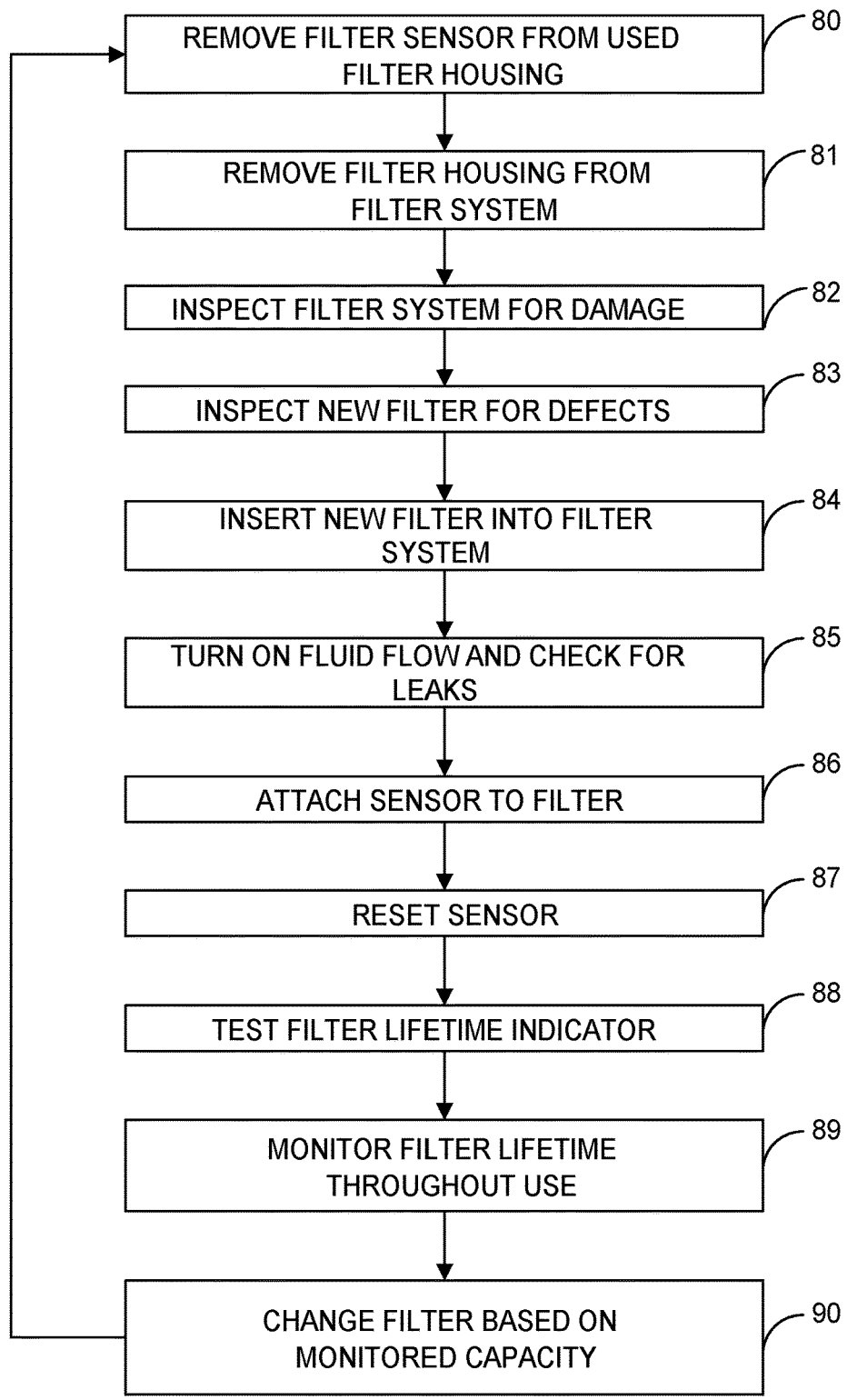
FIG. 8A is a flow diagram illustrating example user operation with respect to exemplary filter sensing systems described herein.

FIG. 8A is a flow diagram illustrating an example user operation with respect to exemplary filter sensing systems described herein. Various filtration systems and filter configurations may be used with various techniques described in this disclosure. The technique of FIG. 8A are described with respect to filter and sensor 20 of FIG. 2 and sensor 20 of FIG. 3 for purposes of illustration. However, it will be understood that the technique of FIG. 8A may be performed for a different sensor system or filter and sensor configuration, and that utilizing a sensor system may include other techniques.

In general, an operator typically removes and/or inspects filter media having diminished filter capacity and in need of replacement (80, 81, 82). At this time, an operator typically selects a new filter, inspects the filter for defects (83) and inserts the filter in the filtration system (84).

Once filters have been installed, fluid flow in the filter system may be turned on to check the new filter and the filter system for leaks (85). At this time, the user may install or otherwise fit one or more sensor 20 to the new filter (86). The user may reset sensor by, for example, activating the sensor reset/test button 22 (87). In addition, at any time, the user may direct the sensor to test the media filter by, for example, activating the sensor reset/test button 22 (88). In some examples, the lifetime or capacity of the filter media may be monitored periodically or asynchronously during use of the filter (89). In response to the monitoring, the operator may change the filter, such as when lifetime is less than a threshold percent (e.g., about 10 percent to twenty percent) of the original lifetime of the new filter (90).

Figure 8B:
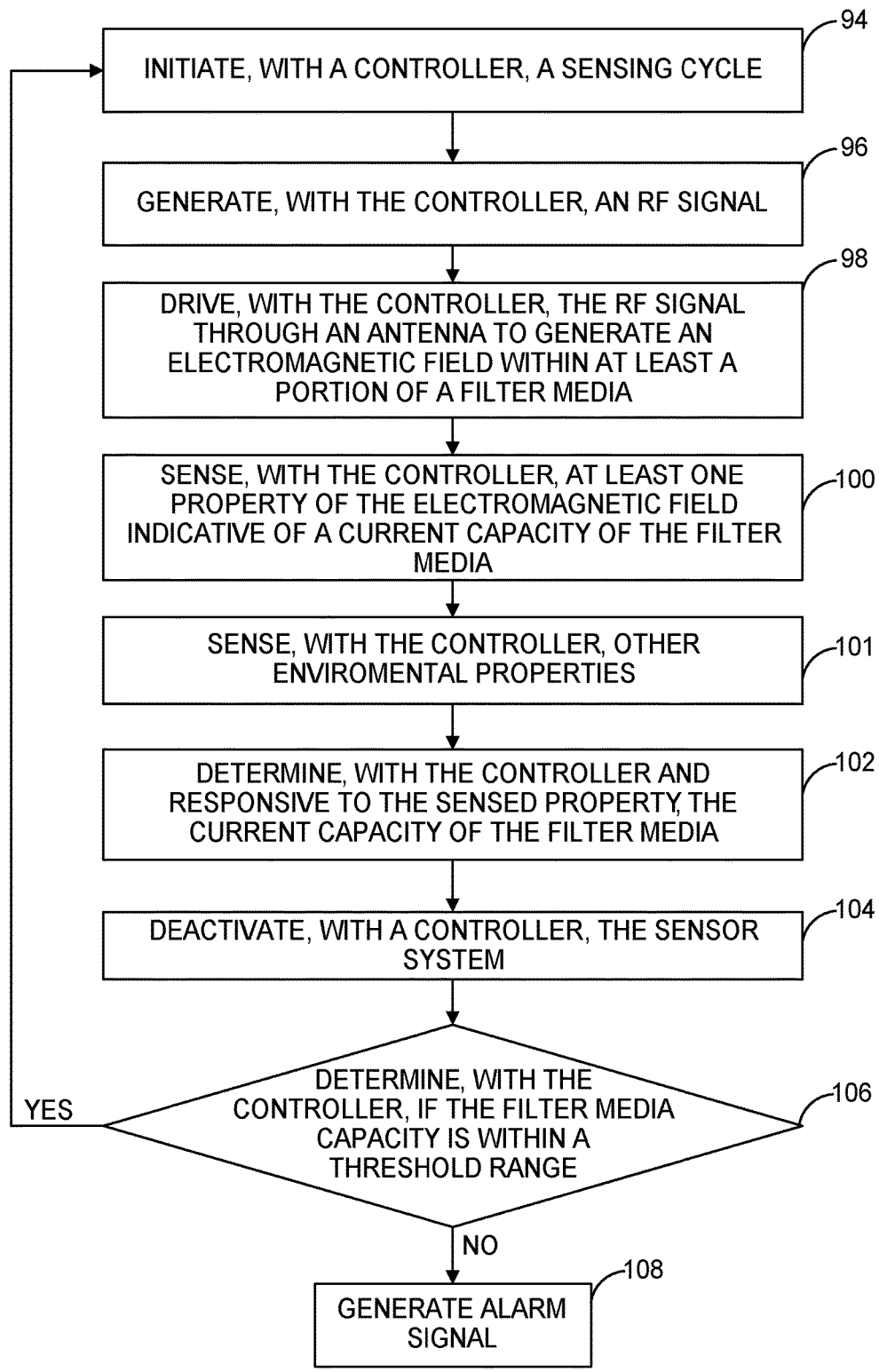
FIG. 8B is a flow diagram illustrating example operation performed by filter media sensing systems described herein.

FIG. 8B is a flow diagram illustrating example operation performed by a sensing system when monitoring a filter media as described herein. Various filtration systems and filter configurations may be used with the techniques of FIG. 8B, which are described, for purposes of illustration, with respect to sensor 50 of FIG. 4. However, it will be understood that the techniques of FIG. 8B may be performed for a different sensor system or filter and sensor configuration, and that utilizing a sensor system may include other techniques.

In the example of FIG. 8B, controller 56 of sensor 50 activates the sensor and initiates a sensing cycle (94). In some examples, controller 56 may initiate the sensing cycle at a predetermined time interval, such as once a day. In some examples, controller 56 may initiate the sensing cycle in response to user input, automated input from an external device such as, for example, a signal from a separate controller or monitoring system (monitor 12 of FIG. 1), or the like.

Upon initiating measurement of the filter media, controller 56 configures RF generator 61 to generate an RF signal (96). In some examples, controller 56 may configure RF generator 61 to generate the RF signal at a resonant frequency of antenna 63. In other examples, the RF signal may be generated at a resonant frequency of antenna 63 located proximate to a filter housing 64. In other examples, the RF signal may be generated at a resonant frequency of the antenna located proximate to a filter housing 64 and filter media 66, as well as other non-filtering media, or the like. In the example of FIG. 8B, controller 56 drives the RF signal through antenna 63 to generate an electromagnetic field within at least a portion of the filter media 66 (98).

Controller 56 receives one or more signals from field sensor 60 that are indicative of at least one property of the electromagnetic field such as, for example, inductance, capacitance, resonant frequency, quality factor, equivalent series resistance, equivalent parallel resistance, or the like (100). In addition, controller 56 may monitor other properties of the environment or water filtration system (e.g., temperature, fluid flow rate) and utilizes the measured properties to compensate or adjust the computed estimate for the remaining capacity of filter media 66 (101). Based on the sensed properties of the magnetic field and any sensed properties for the environment of the water filtration system, controller 56 computes the current capacity of the filter media 66 and updates user interface 54 (102).

Controller 56 may, optionally, deactivate the sensor 50 by terminating generation of the magnetic field and powering down one or more components of sensor 50 such as, for example, user interface 54, field sensor 60, antenna 63, or the like (104).

Based on the computed capacity of the filter media, controller 56 may in some examples determine whether the filter media 66 capacity is within a threshold range (106). In some examples, the threshold range is pre-computed based on sensed properties of the magnetic field when filter media 66 is originally inserted or, in some case, when filter media is not present within the housing. If the filter media 66 capacity is within the threshold range, controller 56 repeats the sensing cycle at a future time or asynchronously in response to input from a user or external monitoring component (YES branch of 106, 94). In the event the filter media 66 capacity is determined to not be within the threshold range, such as below 10% capacity remaining, controller 56 generates an alarm signal or other output, e.g., electronic communication (NO branch of 106, 108). In some examples, the alarm signal may be presented by user interface 54 as, for example, a visual alarm, an audible alarm, or the like. In other examples, the alarm signal may be transmitted by WiFi transmitter 70.

As one example of a sensing process in accordance with the techniques described herein, with respect to dechlorination with an activated carbon filter block, sensor 50 may determine efficacy of the filtration media based on the change in effective resistance over time. For example, sensor 50 may initially sense properties of the resonant circuit (antenna 63 and any resonant cavities coupled thereto) in absence of the carbon filtration block (filter media 66) such as resonant frequency, equivalent parallel resistance, and temperature of the inductive element. In example implementations, the measured parallel resistance ($R_A$) may be, for example, 2000 ohms at a resonant frequency of 13.6 megaHertz. During a subsequent sensing cycle after filter media 66 is installed, sensor 50 again senses the properties of resonant circuit with the inductive element near-field coupled to the carbon filtration block during the initial point of the filtration process. For example, the measured coupled resistance ($R_{AF}$) may at this time be 1000 ohms at a resonant frequency of 13.6 mega-Hertz. Further, sensor 50 may sense additional environmental parameters for the water filtration system including, for example, the temperature of the influent water, temperature of the surrounding environment, water flow through carbon block, and pressure drop across the carbon block may be measured. Controller 56 determines an effective resistance of the filtration media from measured values in each of these measurement cycles. For example, controller 56 may determine, responsive to a current measurement cycle, that the active carbon block filter may have a coupled resistance ($R_F$) of 8000 ohms after filtering 400 gallons of water. Based on the initial parallel resistance ($R_A$) as 2000 ohms in the absence of the filter media, controller 56 may determine that the ($R_F$) 8000 ohms correspond to a 40 percent remaining filter media capacity. Sensor 50 may periodically repeat the process to determine effective resistance of the filtration media during the filtration process.

Figure 9:
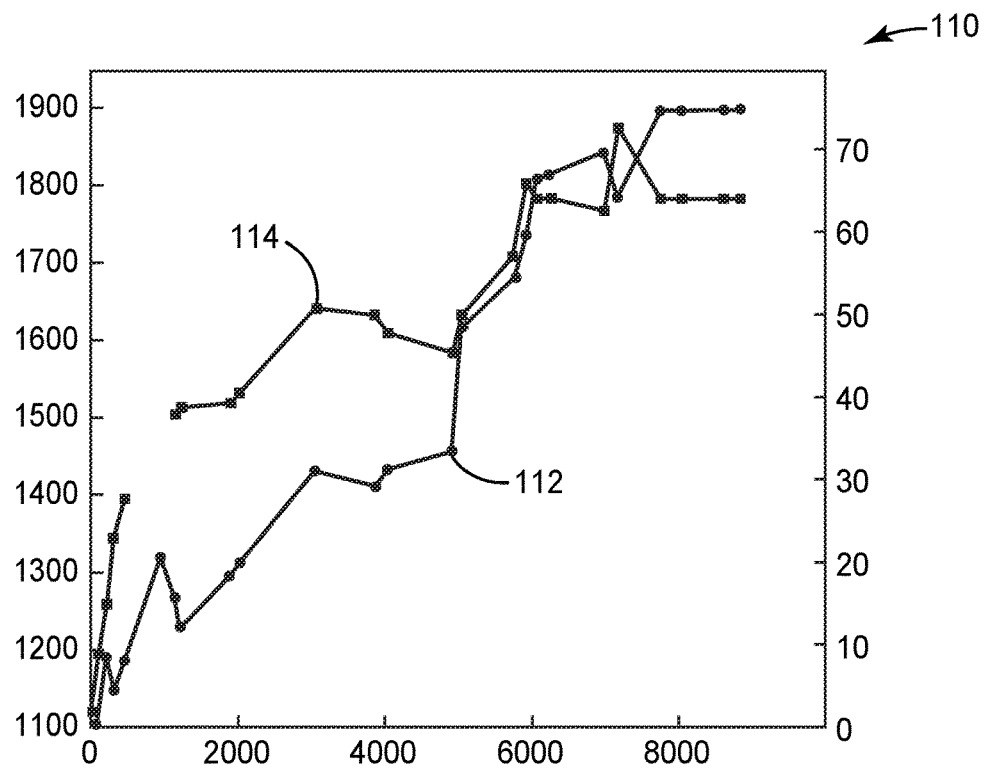
FIG. 9 is a graph illustrating example experimental results for both a filter media resistance and a percent pass of an impurity versus total fluid throughput during an operation of a filter.

FIG. 9 is a graph illustrating example experimental results for both a filter media resistance and a percent pass of an impurity versus total fluid throughput during an operation of a test filter. The influent flow concentration of chlorine was 2 ppm with a constant flow rate of 0.65 gallons per minute. As illustrated in FIG. 9, plot 110 includes a horizontal axis representing gallons of water filtered, a first left-hand vertical axis representing activated carbon filter media resistance ($R_F$) in ohms (plotted as solid diamonds 112), and a second right-hand vertical axis representing percent pass of chlorine (plotted as solid squares 114). In some examples, the filter resistance and percent pass are correlated to the volume of filtered fluid.

In the example of dechlorination, as discussed above, the reduction in the number of available activated carbon sites relates to a reduction in the filter media capacity. Also, as discussed above, the increase in the number of activated carbon oxidized sites corresponds to a reduction in the filter media conductivity, which increases the resultant magnetic field generated by a sensor system. In this way, the filter media resistance may be determined based on the resultant magnetic field generated by the sensor. Furthermore, as discussed above, the reduction in the number of available activated carbon sites corresponds to an increase in percent pass measured as the concentration of chlorine in the filter effluent. As indicated by the experimental results of FIG. 9, filter media resistance and percent pass of an impurity can be correlated and utilized to program controller 56 to determine the filter lifetime or capacity during operation of a filter based on the filter media resistance.

The following table presents the experimental results illustrated in FIG. 9:

| Volume (gal) | 112 (Ω) | 114 (%) |
|---|---|---|
| 7 | 1136.2 | 1.8 |
| 72 | 1106.8 | 8.7 |
| 138 | 1190.0 | 14.8 |
| 180 | 1149.5 | 22.8 |
| 252 | 1186.9 | 27.4 |
| 300 | 1319.9 | |
| 352 | 1267.6 | 37.8 |
| 412 | 1229.3 | 38.5 |
| 472 | 1297.3 | 38.9 |
| 502 | 1313.1 | 40.2 |
| 555 | 1429.4 | 50.4 |
| 618 | 1410.8 | 49.5 |
| 707 | 1430.8 | 47.5 |
| 753 | 1456.1 | 44.9 |
| 813 | 1615.8 | 49.5 |
| 1014 | 1682.7 | 56.8 |
| 1053 | 1737.3 | 65.4 |
| 1125 | 1809.4 | 63.8 |
| 1180 | 1813.8 | 63.8 |
| 1311 | 1843.2 | 62.2 |
| 1373 | 1784.9 | 72.0 |
| 1421 | 1899.0 | 63.6 |

Figure 10:
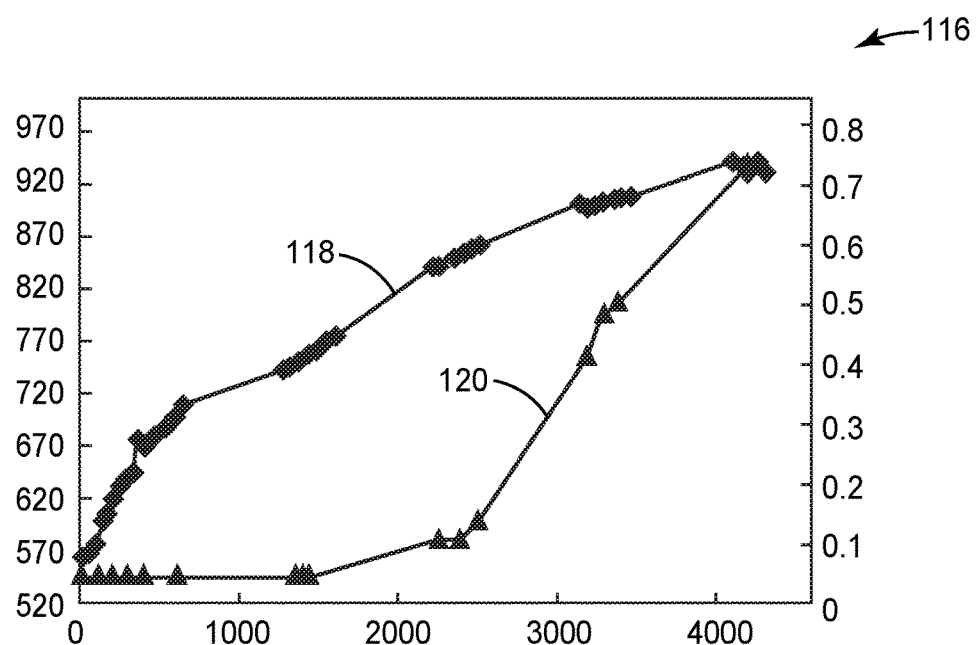
FIG. 10 is a graph illustrating example experimental results for both a filter media resistance and an effluent impurity concentration versus total fluid throughput during an operation of a filter.

FIG. 10 is a graph illustrating example experimental results for both a filter media resistance and an effluent impurity concentration versus total fluid throughput during an operation of a test filter. The influent flow concentration of chlorine was 2 ppm with a constant flow rate of 0.65 gallons per minute. As illustrated in FIG. 10, plot 116 includes a horizontal axis representing gallons of water filtered, a first left-hand vertical axis representing sensor coupled resistance ($R_{AF}$) in ohms (curve 118), and a second right-hand vertical axis representing filter effluent chlorine concentration in parts per million (curve 120). As discussed above, for the example of dechlorination, a reduction in the number of available activated carbon sites relates to both a reduction in the filter media conductivity, as measured by the electromagnetic properties of the filter media, and an increase in chlorine passed, as measured by the concentration of chlorine in the filter effluent. As indicated by the experimental results of FIG. 10, filter media resistance and filter effluent impurity concentration may be correlated and utilized to program controller 56 to determine the filter lifetime or capacity based on filter media resistance.

The following table presents the experimental results illustrated in FIG. 10:

| Volume (gal) | 118 (Ω) | Volume (gal) | 120 (ppm) |
|---|---|---|---|
| 4 | 565.6 | 4 | 0.05 |
| 8 | 565.2 | 99 | 0.05 |
| 12 | 564.5 | 200 | 0.05 |
| 15 | 563.4 | 299 | 0.05 |
| 17 | 561.6 | 395 | 0.05 |
| 20 | 563.3 | 597 | 0.05 |
| 24 | 564.7 | 1349 | 0.05 |
| 28 | 564.5 | 1401 | 0.05 |
| 31 | 564.5 | 1429 | 0.05 |
| 39 | 565.5 | 2251 | 0.11 |
| 59 | 568.1 | 2375 | 0.11 |
| 79 | 575.6 | 2493 | 0.14 |
| 99 | 576.7 | 3182 | 0.42 |
| 139 | 600.4 | 3302 | 0.49 |
| 159 | 605.8 | 3381 | 0.51 |
| 180 | 609.0 | 4205 | 0.74 |
| 200 | 619.7 | | |
| 239 | 631.2 | | |
| 260 | 636.1 | | |
| 279 | 637.5 | | |
| 299 | 642.4 | | |
| 320 | 643.9 | | |
| 357 | 675.2 | | |
| 375 | 674.0 | | |
| 395 | 669.3 | | |
| 446 | 676.7 | | |
| 460 | 680.0 | | |
| 473 | 681.4 | | |
| 514 | 686.9 | | |
| 535 | 688.2 | | |
| 561 | 690.8 | | |
| 574 | 694.6 | | |
| 597 | 696.3 | | |
| 614 | 701.4 | | |
| 640 | 708.0 | | |
| 1272 | 742.5 | | |
| 1309 | 746.6 | | |
| 1349 | 749.6 | | |
| 1401 | 753.2 | | |
| 1429 | 757.5 | | |
| 1468 | 761.5 | | |
| 1519 | 765.8 | | |
| 1546 | 769.2 | | |
| 1591 | 773.5 | | |
| 2221 | 840.6 | | |
| 2251 | 842.4 | | |
| 2342 | 849.2 | | |
| 2375 | 849.7 | | |
| 2413 | 855.0 | | |
| 2451 | 856.9 | | |
| 2493 | 860.5 | | |
| 3144 | 901.5 | | |
| 3182 | 897.9 | | |
| 3223 | 900.1 | | |
| 3263 | 902.0 | | |
| 3302 | 903.0 | | |
| 3343 | 906.4 | | |
| 3381 | 908.5 | | |
| 3424 | 907.0 | | |
| 3460 | 909.4 | | |
| 4108 | 939.8 | | |
| 4148 | 938.1 | | |
| 4205 | 933.0 | | |
| 4239 | 938.6 | | |
| 4290 | 933.5 | | |

Figure 11:
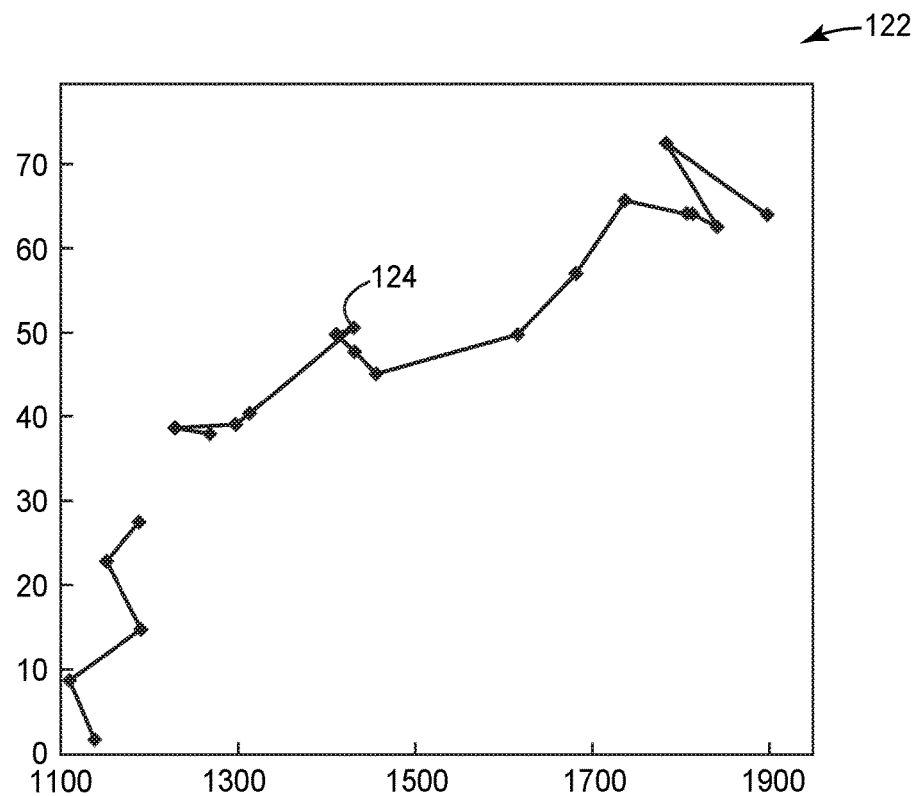
FIG. 11 is a graph illustrating example experimental results for a percent pass of an impurity versus a filter media resistance during an operation of a filter.

FIG. 11 is a graph illustrating example experimental results for a percent pass of chlorine versus an activated carbon filter resistance ($R_F$) during an operation of a filter. The influent flow concentration of chlorine was 2 ppm with a constant flow rate of 0.65 gallons per minute. As illustrated in FIG. 11, plot 122 includes a horizontal axis representing filter resistance ($R_F$) in ohms, and a vertical axis representing percent pass of chlorine. As discussed above, for example, a reduction in the number of available activated carbon sites relates to both a reduction in the filter media conductivity, as measured by the electromagnetic properties of the filter media, and an increase in percent pass of chlorine, as measured by the concentration of chlorine in the filter effluent. As indicated by the experimental results of FIG. 11, the correlation between the filter resistance ($R_F$) and percent pass of an impurity demonstrates that filter resistance may be used to determine the filter lifetime or capacity during the operation of a filter.

The following table presents the experimental results illustrated in FIG. 11:

| Resistance (Ω) | 124 (%) |
|---|---|
| 1136.2 | 1.8 |
| 1106.8 | 8.7 |
| 1190.0 | 14.8 |
| 1149.5 | 22.8 |
| 1186.9 | 27.4 |
| 1319.9 | |
| 1267.6 | 37.8 |
| 1229.3 | 38.5 |
| 1297.3 | 38.9 |
| 1313.1 | 40.2 |
| 1429.4 | 50.4 |
| 1410.8 | 49.5 |
| 1430.8 | 47.5 |
| 1456.1 | 44.9 |
| 1615.8 | 49.5 |
| 1682.7 | 56.8 |
| 1737.3 | 65.4 |
| 1809.4 | 63.8 |
| 1813.8 | 63.8 |
| 1843.2 | 62.2 |
| 1784.9 | 72.0 |
| 1899.0 | 63.6 |

Figure 12:
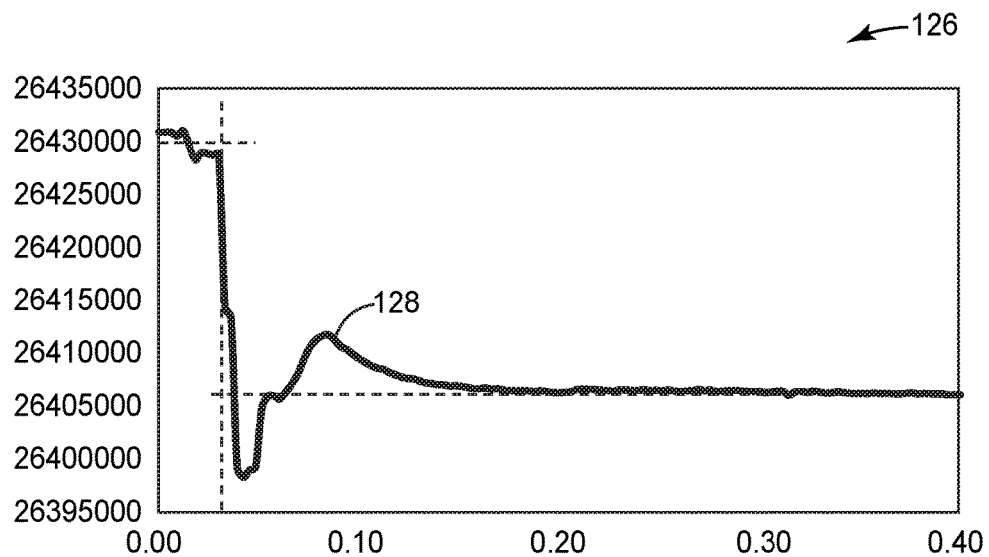
FIG. 12 is a graph illustrating example experimental results for an antenna resonant frequency versus time in hours of a sensor system over a time period during which water was introduced to a dry filter media.

FIG. 12 is a graph illustrating example experimental results for a measured antenna resonant frequency versus time of a sensor system over a period during which water was introduced to a dry activated carbon filter media. As illustrated in FIG. 12, plot 126 includes a horizontal axis representing time in hours, and a vertical axis representing measured resonant frequency of a sensor system antenna in Hertz. In the example of dechlorination, as discussed above, submersion of an activated carbon filter media in water changes the dielectric constant of the volume contained within the filter housing media. The change in dielectric constant is caused by the displacement of air within the housing by water. The change in dielectric constant causes a shift in the resonant frequency of sensor system antenna transmitting and receiving electromagnetic signals through the filter media, in accordance with one or more techniques of this disclosure. As such, a shift in resonance frequency may be used by controller 56 to detect dielectric or capacitive changes within the filter housing. Moreover, in some examples, a controller may sense an initial shift of significant magnitude (as shown in FIG. 12) in the measured resonant frequency of the antenna to detect initial exposure of the filter media to fluid, in response, control one or more components of the sensor system. For instance, in the example of FIG. 4, controller 56 may capture initial sensed parameters of the surrounding environment, reset user interface 54, send a signal by a radio transmitter 70, control sensor 50 to activate at one or more predetermined time intervals, or the like. In this way, a shift in a resonant frequency of sensor system antennae may indicate the introduction of fluid in the system.

The following table presents the experimental results illustrated in FIG. 12:

| Time (hr) | Resonant Frequency (Hz) |
|---|---|
| 0.00 | 26430848 |
| 0.02 | 26428886 |
| 0.04 | 26398144 |
| 0.06 | 26406176 |
| 0.08 | 26411628 |
| 0.11 | 26408720 |
| 0.13 | 26407436 |
| 0.15 | 26406792 |
| 0.17 | 26406522 |
| 0.19 | 26406336 |
| 0.21 | 26406472 |
| 0.23 | 26406376 |
| 0.25 | 26406384 |
| 0.28 | 26406388 |
| 0.30 | 26406240 |
| 0.32 | 26406212 |
| 0.34 | 26406220 |
| 0.36 | 26406070 |
| 0.38 | 26406064 |

Figure 13:
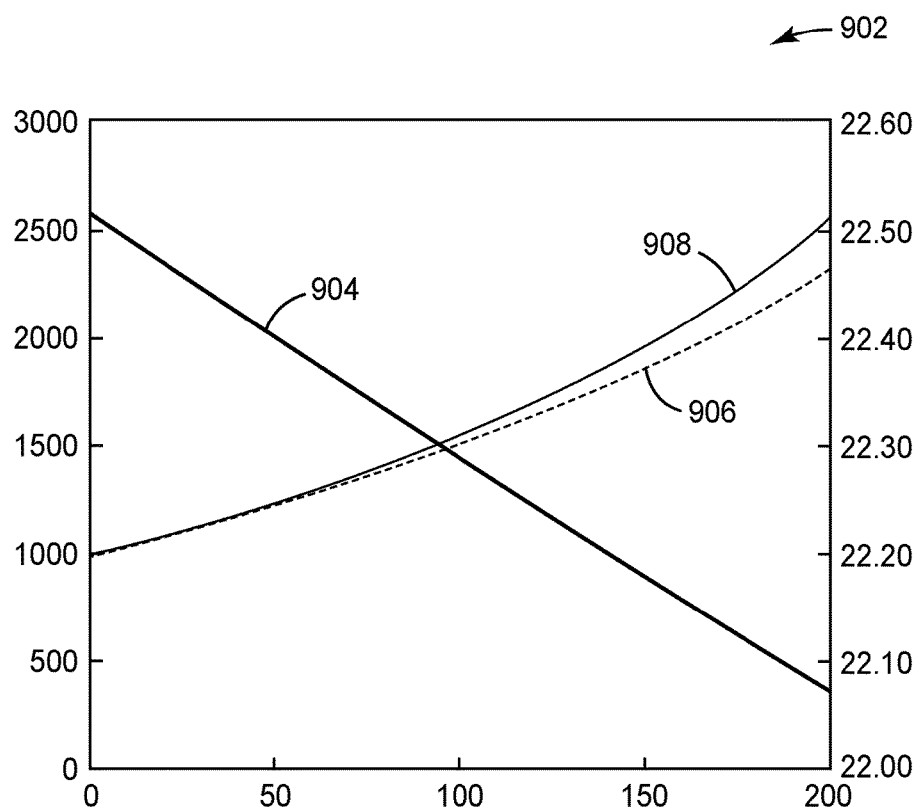
FIG. 13 is a graph illustrating additional example experimental results for an antenna resonant frequency of a sensor system and filter resistance versus volume of fluid filtered during operation of a filter.

FIG. 13 is a graph illustrating additional example for an antenna resonant frequency of a sensor system and filter resistance versus volume of fluid filtered during operation of a filter. As illustrated in FIG. 13, plot 902 includes a horizontal axis representing filtered volume of fluid in gallons, and a left-hand vertical axis representing filter resistance ($R_F$) in ohms and a right-hand vertical axis representing resonant frequency of an antenna in megaHertz. In the example, the sensor inductance was fixed, the parallel resistance ($R_{AF}$) was increased with filtered volume, and the sensor capacitance was increased to represent an increase of dielectric constant of the volume contained within the filter housing. Curve 904 illustrates the decrease in resonant frequency observed from example. Curve 906 represents an uncorrected resistance of a sensor ($R_{AF}$), where the resonant frequency was assumed constant. Curve 908 illustrates a corrected filter media resistance based on the compensation for the resonant frequency change. As illustrated in FIG. 13, the correction to the filter media resistance was determined to be greater as the total filtered volume increased.

The following table presents the example illustrated in FIG. 13:

| Volume (gal) | 904 (MHz) | 906 (Ω) | 908 (Ω) |
|---|---|---|---|
| 0 | 22.508 | 999.8 | 999.8 |
| 10 | 22.485 | 1040.6 | 1042.8 |
| 20 | 22.463 | 1083.1 | 1087.8 |
| 30 | 22.441 | 1127.4 | 1135.1 |
| 40 | 22.418 | 1173.6 | 1184.8 |
| 50 | 22.396 | 1221.9 | 1237.0 |
| 60 | 22.374 | 1272.4 | 1292.1 |
| 70 | 22.352 | 1325.2 | 1350.3 |
| 80 | 22.330 | 1380.6 | 1411.7 |
| 90 | 22.308 | 1438.6 | 1476.8 |
| 100 | 22.286 | 1499.6 | 1545.9 |
| 110 | 22.264 | 1563.6 | 1619.3 |
| 120 | 22.243 | 1631.0 | 1697.5 |
| 130 | 22.221 | 1702.1 | 1780.9 |
| 140 | 22.199 | 1777.1 | 1870.2 |
| 150 | 22.178 | 1856.5 | 1965.9 |
| 160 | 22.156 | 1940.4 | 2068.8 |
| 170 | 22.135 | 2029.5 | 2179.8 |
| 180 | 22.113 | 2124.1 | 2299.9 |
| 190 | 22.092 | 2224.8 | 2430.2 |
| 200 | 22.071 | 2332.2 | 2572.1 |

Figure 14:
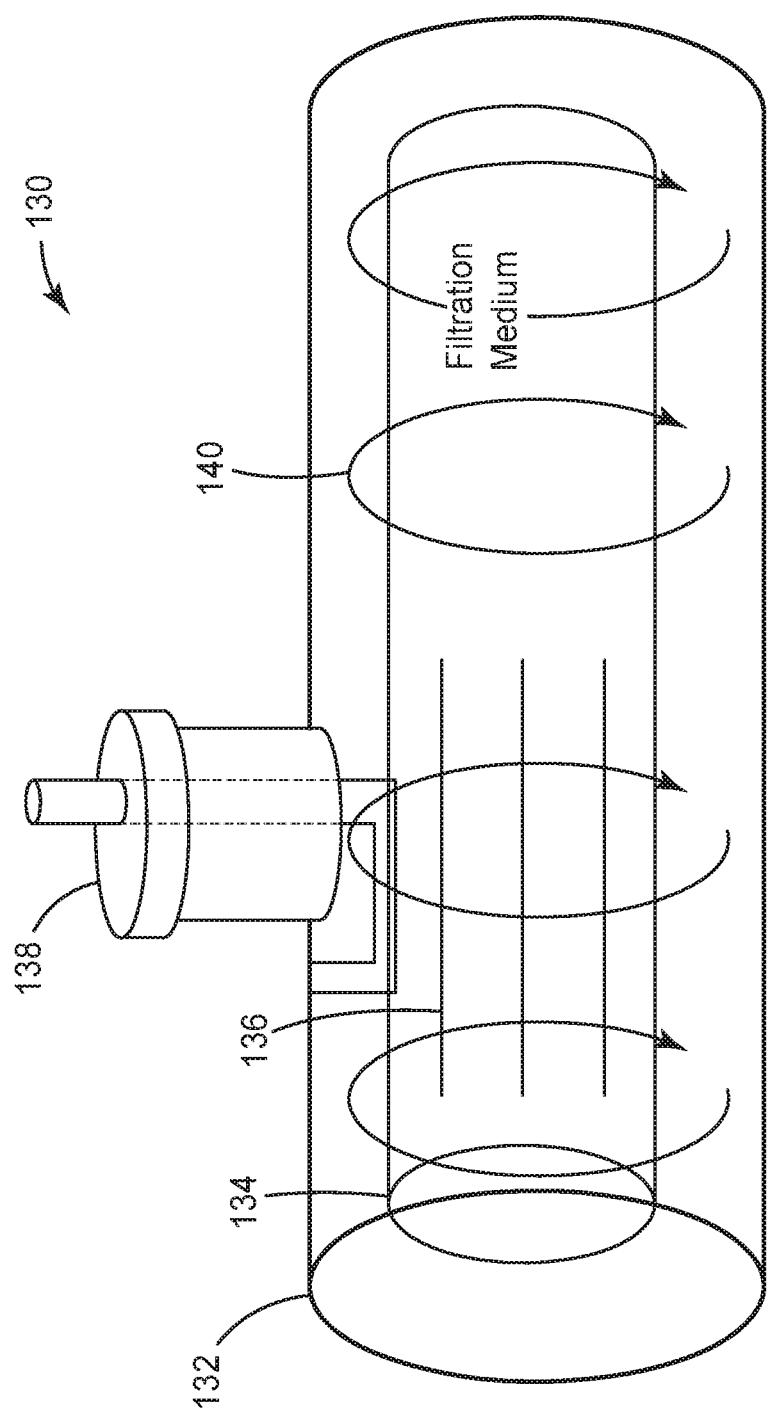
FIG. 14 is a schematic diagram illustrating an example embodiment in which a sensor affixed to a conductive housing utilizes the conductive housing as resonant cavity to aid sensing properties of the filter media contained therein.

FIG. 14 is a schematic diagram illustrating another example embodiment in which sensor 130 containing filter media 134 such that the sensor utilizes the conductive housing 132 as resonant cavity to aid sensing properties of the filter media. In various examples, sensor 130 may be utilized to sense the filter capacity during the filtration of liquids or gases.

In the example of FIG. 14, the conductive filter housing 132 is a conductive material such as, for example, a metal, a conductive polymer, or the like. Moreover, in the example of FIG. 14, the conductive filter housing 132 is cylindrical in shape. In other examples, the conductive filter housing 132 may be, for example, cuboidal, prismatic, conical, or the like. In some examples, conductive filter housing 132 may be configured to fit an existing water filtration system or subsystem. In other examples, conductive filter housing 132 may be configured to fit a new water filtration system or subsystem.

In the example of FIG. 14, a sensor 138 is positioned adjacent and external to conductive filter housing 132. In other examples, the sensor 138 may be positioned external to the conductive filter housing 132 and defining a gap between a surface of the sensor 138 and conductive filter housing 132. In other examples, the sensor 138 may be at least a portion of the surface of the conductive filter housing 132. In other examples, the sensor 138 may be positioned internal to the filter housing. In some examples, the sensor 138 may be connected to the conductive filter housing 132 by bonding, for example, adhesive bonding, thermal bonding, laser bonding, welding, or the like. In other examples, the sensor 138 may be integrated into the material of the conductive filter housing 132 to form a single continuous component. In other examples, the sensor 138 may be connected to the conductive filter housing 132 by a mechanical connection by, for example, one or more fasteners, one or more clamps, one or more ridges or grooves in the surface of the filter housing 132 and sensor 138, or the like. In some examples, the sensor 138 may be positioned in a center of a longitudinal axis of the conductive filter housing 132. In other examples, the sensor may be positioned near an end of the conductive filter housing 132. In other examples, the sensor 138 may be varyingly positioned between the end and the center of the filter housing 132.

In some examples, sensor 138 may include an electrical interface for coupling to a waveguide (not shown) integrated within housing 132, where the waveguide is configured to direct the RF wave produced by sensor 138 into the cavity defined by the conductive filter housing 132. In some examples, the waveguide may be configured to propagate a radio frequency emitted by an antenna (not shown) with minimal loss of energy and to transmit the radio frequency into the cavity defined by the conductive filter housing 132. In some examples, the waveguide may be substantially straight. In other examples, the waveguide may be curved or twisted along a longitudinal axis of the waveguide. In some examples, the waveguide may include a nonconductive plate or barrier, through which a radio frequency signal, but not a fluid, may pass.

As an example, sensor 138 may be implemented as sensors 18, 50 described above. As such, although not shown, sensor 138 may include user interface elements, such as a test/reset button, indicator lights and the various components described in FIG. 4. In the example of FIG. 14, sensor 138 generates a radio frequency selected to resonant in the cavity defined by the conductive filter housing 132. For example, one or more field equations may be used to determine the radio frequency that forms a standing wave inside the cavity defined by the conductive filter housing 132. The cavity defined by the conductive filter housing 132 may define a resonant cavity that supports an electromagnetic oscillation. The properties of the resonant cavity can be determined by the dimensions of the cavity and the conductivity, permittivity, and permeability of the material contained in the cavity. In the case of water filtration, for example, the properties of the cavity defined by the conductive filter housing 132 may be altered by material properties of the filtration media 134. Example details for calculating properties of cavity resonators are described in *Formulas for cavity resonators*. Journal of Applied Physics, Hansen, 9, pg. 654 (1938), the contents of which are incorporated herein by reference.

In the example of FIG. 14, a resonant frequency generates a standing wave having magnetic field 140 and electric field 136 that propagates through at least a portion of the filter media 134, which in turn may generate eddy currents in the filter media 134. These eddy currents may reduce the resultant magnetic field 140. The reduced overall magnetic field 140. The reduced overall electromagnetic field 140 may indicate a property of the filter media 134 such as, for example, conductivity, dielectric strength, magnetic permeability, or the like. As such, field sensor 60 of sensor 50 may monitor the strength of the magnetic field and output properties indicative of antenna 63 and the magnetic field, as described above.

In the example of FIG. 14, sensor 138 includes one or more controllers (e.g., controller 56) that determine a property of the radio frequency or magnetic field 140. In some examples, the controller may determine, for example, filter media 134 conductivity, dielectric strength, magnetic permeability, or the like. For example, the controller may associate a change in filter media 134 conductivity with a change in the quality-factor (q-factor) of the resonant cavity. In this way, the controller may monitor filter media 134 lifetime or capacity based on a change in the filter media 134 conductivity. As another example, the controller may associate a change in filter media permittivity with a change in the resonant frequency of the resonant cavity. In this way, the controller may monitor filter media 134 lifetime or capacity based on a change in the resonant frequency of the resonant cavity. In yet another example, the controller may monitor both a change in electrical conductivity and a change in permittivity of the filter media 134, as described above, to monitor filter media 134 lifetime or capacity.

Figure 15:
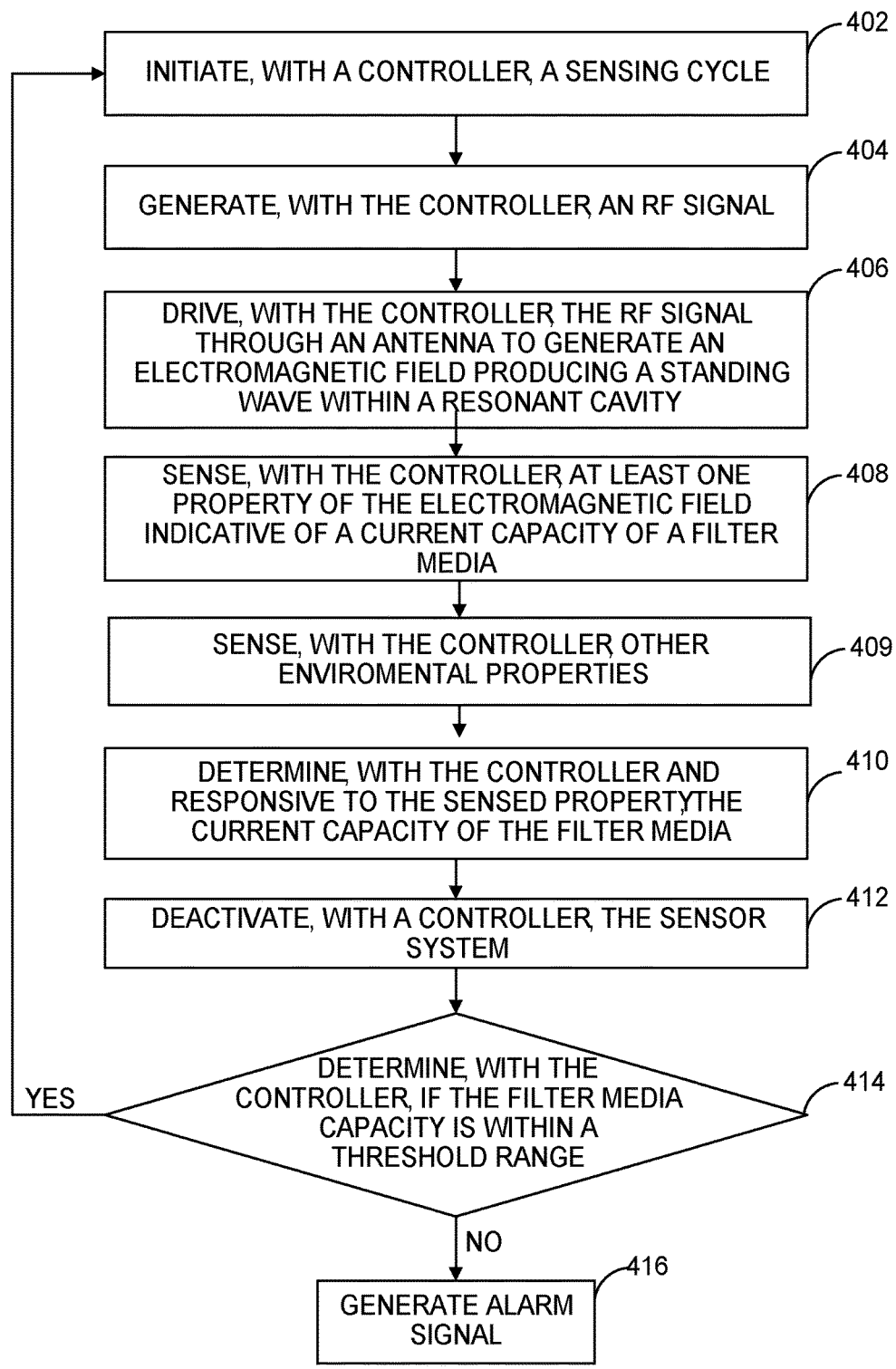
FIG. 15 is a flow diagram illustrating example operation for monitoring a filter media using a sensor system that utilizes the filter housing as a resonant cavity to aid filter monitoring.

FIG. 15 is a flow diagram illustrating example operation for monitoring a filter media using a sensor system that utilizes the filter housing as a resonant cavity to aid filter monitoring. For purposes of example, FIG. 15 is described with respect to the components of sensor 50 shown in FIG. 4. Various filtration systems and filter configurations may be used with the techniques of FIG. 15, which are described, for purposes of illustration, with respect to sensor system 130 of FIG. 12. However, it will be understood that the techniques of FIG. 15 may be performed for a different sensor system or filter and sensor configuration, and that utilizing a sensor system may include other techniques.

In the example of FIG. 15, controller 56 within sensor 138 initiates a sensing cycle (402). In some examples, controller 56 may initiate the sensing cycle at a predetermined time interval, such as once a day. In some examples, controller 56 may initiate the sensing cycle in response to user input, automated input from an external device such as, for example, a signal from a separate controller or monitoring system (monitor 12 of FIG. 1), or the like.

Upon initiating measurement of the filter media, controller 56 configures RF generator 61 to generate an RF signal (404). In some examples, the RF signal may be a resonant frequency of the resonant cavity defined by the internal boundaries of the internal boundaries of the conductive filter housing 132 to produce a standing wave such that the standing wave propagates through the filter media 134. In the example of FIG. 15, RF generator 61 drives the RF signal into the resonant cavity to generate an electromagnetic field producing a standing wave inside the resonant cavity (406).

In some examples, RF generator 61 may drive the RF signal through antenna 63 that is arranged to extend through a port into the resonant cavity, i.e., the filter housing. In other examples, the controller may drive the RF signal through a nonconductive window in a wall of the resonant cavity. In other examples, the controller may drive the RF signal through a waveguide integrated within the filter housing so as to propagate the RF signal into the resonant cavity.

Controller 56 receives one or more signals from field sensor 61 that are indicative of at least one property of the resonant cavity, for example, resonant frequency and quality factor, or the like (408). In addition, controller 56 may monitor other properties of the environment or water filtration system (e.g., temperature, fluid flow rate) and utilizes the measured properties to compensate or adjust the computed estimate for the remaining capacity of filter media 134 (409). Based on the sensed properties of the resonant cavity and any sensed properties for the environment of the water filtration system, controller 56 computes the current capacity of the filter media 134 and updates user interface 54 (410).

Controller optionally deactivates sensor 138 by powering down one or more components of sensor system 130 such as, for example, a user interface, rf generator, antenna, or the like (412). In other examples, controller may deactivate sensor system 130 by powering down one or more components of sensor system 130 such as, for example, a user interface, RF generator, antenna, or the like (412).

Based on the computed capacity of the filter media, controller 56 may in some examples determine whether the capacity of filter media 134 is within a threshold range. If the estimated capacity of filter media 134 is determined to be within the threshold range, the controller 56 repeats the sensing cycle at a future time or asynchronously in response to input from a user or external monitoring component (YES branch of 414, go to 402). In the event the capacity of filter media 134 is determined to not be within the threshold range, such as below 10% capacity remaining, controller 56 generates an alarm signal or other output, e.g., electronic communication (NO branch of 414, go to 416). In some examples, the alarm signal may be presented by a user interface as, for example, a visual alarm, an audible alarm, or the like. In other examples, the alarm signal may be transmitted by a radio frequency transmitter.

Figure 16:
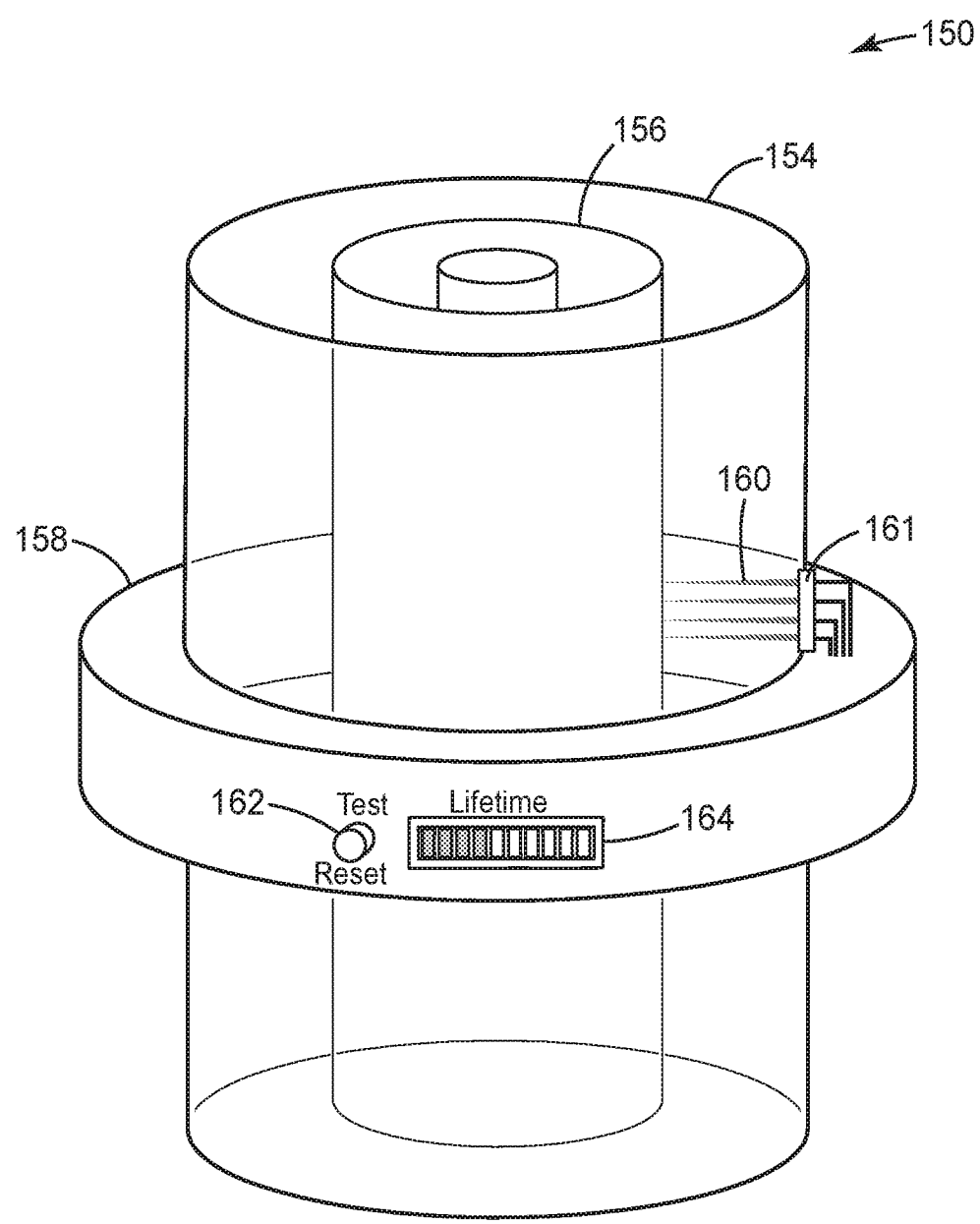
FIG. 16 is a schematic diagram illustrating an example filter housing and a direct electrical contact sensor system.

FIG. 16 is a schematic diagram illustrating an example filter housing and a direct electrical contact sensor system affixed thereto. As in the other examples described herein, filter housing and sensor system 150 may be utilized in the filtration of liquids or gases. In some examples filter housing 154 may be a nonconductive filter housing constructed of material such as, for example, plastic, glass, porcelain, rubber, and the like. In other examples filter housing 154 may be a conductive material such as, for example, metals, conductive polymers, and the like. In the example of FIG. 16, filter housing 154 is cylindrical in shape. In other examples, filter housing 154 may be, for example, cuboidal, prismatic, conical, or the like. In some examples filter housing 154 may be configured to fit an existing filtration system or subsystem. In other examples, nonconductive filter housing 154 may be configured to fit a new water filtration system or subsystem.

In the example of FIG. 16, a sensor 158 is positioned adjacent and external to filter housing 154 and has a set of (e.g., four) electrical probes protruding through filter housing 154 and into at least a portion of filter media 156. As with the other example implementations described herein, sensor 158 may be flush mounted to filter housing 154 or may be mounted proximate the filter housing 154. Sensor 158 may be connected to the filter housing 154 by bonding, for example, adhesive bonding, thermal bonding, laser bonding, welding, or the like. In other examples, the sensor 158 may be integrated into the material of the filter housing 154 to form a single continuous component. In other examples, the sensor 158 may be connected to the filter housing 154 by a mechanical connection by, for example, one or more fasteners, one or more clamps, one or more ridges or grooves in the surface of the filter housing 154 and sensor 158, or the like. In some examples, the sensor 158 may be positioned in a center of a longitudinal axis of the filter housing 154. In other examples, the sensor may be positioned near an end of the filter housing 154.

In the example of FIG. 16, sensor 158 is electrically configured with four probes 160 to protrude through filter housing 154 in a sealed manner so as to extend into at least a portion of the filter media 156. In other examples, sensor 158, coupled to probes 160, may be positioned on the exterior of the filter housing 154 and interface inductively with associated probes positioned on the interior of the filter housing 154 that protrude into filter media 156 such that probes 160 need not physically protrude through the filter housing. In some examples, probes 160 may include a nonconductive sheath and protrude through holes in filter housing 154 so as to form a fluid tight seal between the probes 160 and filter housing 154.

Probes 160 measure one or more properties of filter media 156 such as, for example, acoustic properties, electrical properties, mechanical properties, optical properties, or the like. In some examples, the measured one or more properties of the filter media 156 are indicative of the filter media remaining lifetime or capacity.

In some examples, an internal power source (not shown) such as, for example, a battery, may power a controller that, in turn, controls supply electrical current to the probes 160. In other examples, an external power supply such as, for example, local power supplies, alternative current to direct current converters, or the like, may supply electrical current to the probes 160. The applied electrical current configured to pass through the filter media can take the form of direct, alternating, or a pulsed waveform current.

As an example, sensor 158 may be implemented similar to the implementation and operation of sensors 18, 50 described above. As such, sensor 158 may include user interface elements 162, 164, such as a test/reset button, indicator lights and the various components described in FIG. 4.

In the example of FIG. 16, four metal probe 160 are in direct electrical contact with a portion of filter media 156. In some examples, probes 160 may include two or more metal probes 160 in direct contact with at least a portion of the filter media 156. The metal probes 160 may interface with the filter media 156 through an electrical current. In general, filter media 154 provides an electrical resistance to the electrical signal applied by sensor 158, and sensor 158 measures voltage across and/or current through the filter media to determine the resistivity of the filter media 154. In some examples, the controller within sensor 158 may be programmed with one or more predetermined lifetime resistivity curves for media filters and, using the data, compute a remaining capacity of the media filter based on the measured resistivity. In the example of FIG. 16, the controller interfaces with the user interface 164 to display the remaining filter media lifetime or capacity. In the case of dechlorination of water using activated carbon filter media, for example, four metal probes may protrude through a nonconductive filter housing to contact at least a portion of the filter media.

For electrical measurements, surface oxidation (corrosion) of the electrical probes may lead to an error in the measurements. To prevent oxidation, the electrical probes may consist of or be coated by a noble metal, a corrosion resistant alloy, or treated with a corrosion inhibitor. In addition to surface oxidation, maintaining a robust and consistent contact force between the electrical probes and filter may be achieved by using spring-loaded pins or through mechanical design (e.g., probes behave as springs). In some applications, the contact electrodes may directly contact the filter block. For examples, the electrodes can be in electrical contact with the inner and outer surfaces or the top and both ring plane faces of a hollow cylindrical block filter. Based on the fluid flow profile through the block, placement of electrodes on various surfaces of a block filter may be advantageous to control or maximize sensitivity.

In some applications, the contact electrodes may not directly contact the filter media but use the presence of an electrically conductive fluid between the electrodes and filter media to facilitate the electrical connection. The conductivity ratio between the filter block and the fluid may affect the sensor sensitivity. A higher sensor sensitivity may be achieved when the ratio of filter conductivity to fluid conductivity is low. For examples, the ratio can be between 0.001 and 1000. In one embodiment the ratio is less. In one embodiment the ratio is greater than 1.

In applications where more than two electrodes are used, the electrodes may be individually addressed, source both current and voltage, sense both current and voltage, and arranged in a collinear array. On both the inner and outer surface of the filter housing, the electrodes can be fabricated to be flush, protrude, or countersunk relative to the surface.

Connector feature 161 electrically couples to probes 160 and provides a means to allow communication between the electrical contacts and the controller of the sensor. In one embodiment, connector 161 can be electrical pins or contacts that pass through the filter housing. The connector can be designed to provide a fluid tight seal to eliminate fluid leak during the filtering process. In some embodiments, the connector and the electrical contacts can be combined into a single entity. In other embodiments, the connector could be configured to enable wireless communication between the controller and the electrical contacts. In this embodiment, the connector includes two near-field coupled antennas positioned on the inner and outer surfaces of the filter housing. The antenna positioned on the inner surface of the housing is directly coupled to the contact electrodes and the antenna on the outer surface of the housing is directly coupled to the controller. In the described example, the controller can electrically communicate with the electrical contacts in a wireless manner. The addition of magnetic materials disposed or contained within the housing can be used to improve the magnetic coupling.

In still other examples, the connector features or the electrical contacts can pass through an inlet or outlet port on the filter housing. In this example, using the inlet and outlet ports to pass the connector or electrodes is advantageous because additional pass-through (holes) on the filter housing are not required that may provide points of mechanical failure or fluid leaks.

Various types of media filter may be used with the sensors described herein. In some filter types, especially for activated carbon filters, both granulated and block filter technologies may be utilized. Granulated filtration media contain individual filter media particles packed in a bed and through which the fluid flows. Common examples of granulated filters are granulated carbon filters and calcium sulfate filters. In contrast, block filters contain pulverized filtration media that is shaped into a single block under high pressures and may undergo a sintering process. A common example of a block filter is a carbon block filter for water filtration. The block filter type may provide several advantages over a granulated filter when used in combination with the described sensing modality.

The first of which is a use of single monitoring location in order to determine remaining filter capacity of the entire filter block. The design of the filter block can results in a substantially uniformly distributed flux of fluid passing through the block. A uniform flux causes a substantially uniform decrease in the filter capability throughout the filter block. Therefore, monitoring at any position within the block would result in measurement of remaining filter capacity of the entire block. In applications where the flux is non-uniform and known (or can be modeled or measured), a correction factor can be applied to account for local flux and generalize the results to other positions of the block. In some applications, the non-uniform flux may lead to an increase in sensor sensitivity. The capability to use a single set of electrodes at any position along the block is envisioned to result in a lower system cost and reduced measurement error.

The second advantage is mechanical rigidity of a block type filter. In a block filter, the filter media is generally in a fixed position within the filter housing during filtration or mechanical vibration. In contrast, for granulated filters, the position and orientation of the individual granules within a filter can move relative to each other during fluid flow, vibration, and non-destructive impact. Movement of the individual granules may cause a significant change in the contact impedance between electrical contacts and the filter media. In addition, the electrical path through the filter may change, involve different filter granules, and have a different granule-granule impedance. In the envisioned application where filter capacity is based on an electrical change of the filter media, movement of filter granules relative to the electrical contacts may lead to significant measurement artifacts.

A third advantage is a block filter may have a higher, more stable, and more consistent conductivity since the filter media is compressed together. In contrast, conductivity through granulated filters may be strongly influenced by the interface between granules. From measurement to measurement these influences may change do to water flow, temperature, passing current, mechanical vibration, or pressure differences within the system.

As an example, an experiment was conducted to measure filter media resistance over time by direct electrical contact. In the experiment, a 4-point measurement probe was configured to measure electrical resistivity of a Frigidaire PureSource Ultra II filter manufactured by 3M Company of Saint Paul, Minn. Digital multimeters were set to 4-wire measurement mode. Prior to assembly, four co-linear 0.078" thru holes were drilled in the plastic housing with a spacing of 0.156". For two filters, the set of four co-linear holes were drilled near the center of the filter's length. For a third filter, 3 sets of four co-linear holes drilled near the top, middle, and bottom along the filter's length. To allow direct electrical contact with the carbon filter, the standard paper filter wrap was not included in the assembly. Gold coated spring-loaded contact pins were inserted through the holes in the filter housing to create electrical contact with the filter. 3M DP 100 clear epoxy was used to secure and seal around the contact pins. A polycarbonate support block was epoxied to the housing to provide additional support to the setup. The experimental parameters were:

Filter: Frigidaire "Pixie" PureSource Ultra II
Flow Rate: Continuous 0.65 gallons per minute
Chlorine Conc.: Average of 2 ppm (1.5-2.5 ppm)
Water Temp.: Not measured
Duration: 470 minutes
Total Volume: 305 gallons
Measurement: Manual (see graphs below)

Figure 17:
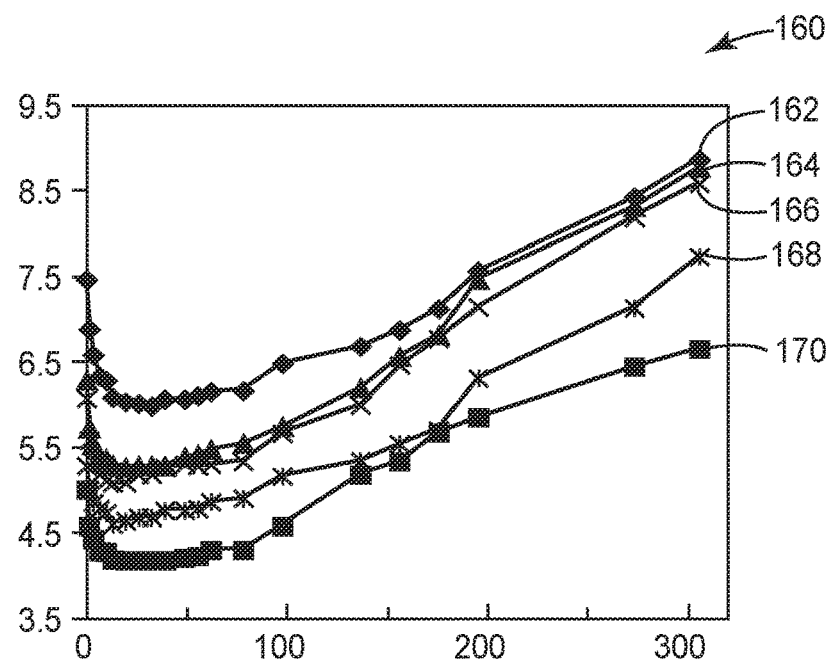
FIG. 17 is a graph illustrating experimental results for a filter media resistance measured by direct electrical contact versus total fluid throughput during an operation of a filter.
Figure 18:
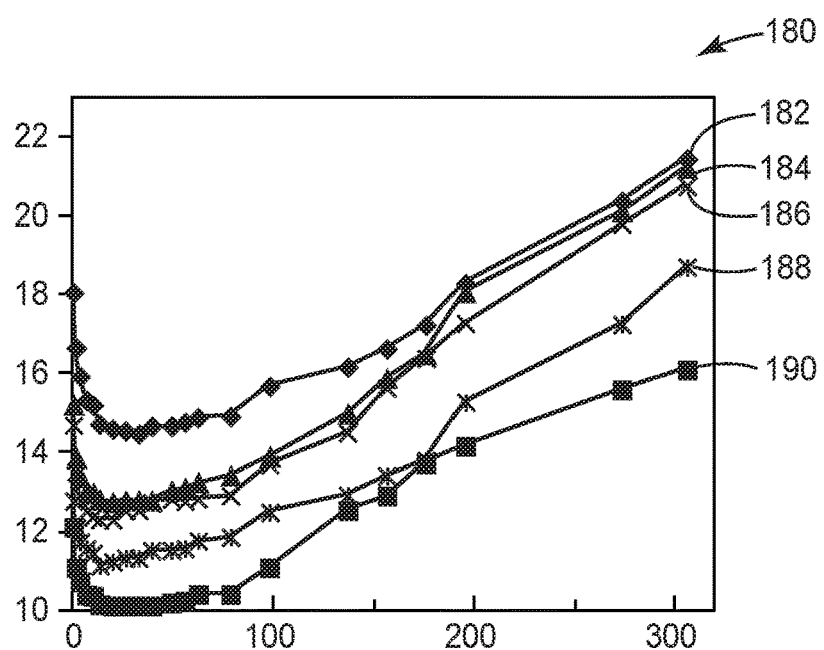
FIG. 18 is a graph illustrating experimental results for a filter media resistance measured by direct electrical contact versus total fluid throughput during an operation of a filter.

FIGS. 17 and 18 are graphs of experimental results showing the measured in-situ resistance ($\Omega$) and calculated resistivity ($\Omega \cdot cm$). For all the filters measured, two trends were observed in the experimental results. The first was a decrease in resistance during the initial 20-40 filtered gallons of the experiment. The second observed trend was a significant and steady increase in resistance from 40-305 gallons. The increase in measure resistance was likely caused by an increase is surface oxidation of the carbon filter over time caused by the reduction of chlorine. These experimental results illustrate that the amount of filtered water containing chlorine can be monitored through measuring the change in electrical resistance of an activated carbon filter.

FIG. 17 is a graph illustrating experimental results of filter media resistance measured by direct electrical contact versus total fluid throughput during an operation of a filter. As illustrated in FIG. 17, plot 160 includes a horizontal axis representing gallons filtered during operation of a filter and a vertical axis representing measured filter media resistance in ohms. In the example of FIG. 17, approximately 305 gallons of water containing approximately two parts per million of chlorine was filtered by three activated carbon filters of a substantially similar construction. In FIG. 17, curves 162 and 170 correspond to two separate experimental filters, each including one sensor with a set of four metal probes positioned in the center of the longitudinal axis of the filter media. Also, in the example of FIG. 17, curves 164, 166, and 168 correspond to a single experimental filter, having three separate sensors, each sensor including a set of four metal probes: Curve 164 corresponds to the sensor positioned near a top of the single experimental filter; Curve 166 corresponds to the sensor positioned near a center of the longitudinal axis of the single experimental filter; and Curve 168 corresponds to the sensor positioned near a bottom of the single experimental filter. As discussed above, for example, an increase in the number of available activated carbon oxidation sites relates to a reduction in the filter media conductivity, as measured by the electromagnetic properties of the filter media. As indicated by the experimental results of FIG. 17, filter lifetime or capacity may be determined by filter media resistance measured during operation of a filter.

The following table presents the experimental results illustrated in FIG. 17:

| | Filter | | | | |
|---|---|---|---|---|---|
| Gallons Filtered | 162 ($\Omega$) | 170 ($\Omega$) | 164 ($\Omega$) | 166 ($\Omega$) | 168 ($\Omega$) |
| 0.0 | 7.48 | 5.02 | 6.30 | 6.09 | 5.30 |
| 1.3 | 6.90 | 4.60 | 5.74 | 5.60 | 5.02 |
| 3.3 | 6.60 | 4.45 | 5.55 | 5.36 | 4.87 |
| 6.5 | 6.35 | 4.31 | 5.40 | 5.20 | 4.80 |
| 9.8 | 6.30 | 4.30 | 5.38 | 5.13 | 4.75 |
| 13.0 | 6.10 | 4.21 | 5.31 | 5.10 | 4.62 |
| 19.5 | 6.05 | 4.20 | 5.28 | 5.10 | 4.66 |
| 26.0 | 6.03 | 4.20 | 5.30 | 5.20 | 4.70 |
| 32.5 | 6.00 | 4.20 | 5.30 | 5.20 | 4.70 |
| 39.0 | 6.08 | 4.20 | 5.30 | 5.28 | 4.78 |
| 48.8 | 6.08 | 4.23 | 5.40 | 5.32 | 4.78 |
| 55.3 | 6.12 | 4.25 | 5.43 | 5.30 | 4.80 |
| 61.8 | 6.17 | 4.32 | 5.49 | 5.32 | 4.88 |
| 78.0 | 6.18 | 4.32 | 5.56 | 5.35 | 4.92 |
| 97.5 | 6.50 | 4.60 | 5.76 | 5.68 | 5.18 |
| 136.5 | 6.70 | 5.20 | 6.21 | 6.01 | 5.36 |
| 156.0 | 6.89 | 5.35 | 6.58 | 6.48 | 5.56 |
| 175.5 | 7.14 | 5.69 | 6.83 | 6.79 | 5.72 |
| 195.0 | 7.58 | 5.87 | 7.48 | 7.16 | 6.33 |
| 273.0 | 8.44 | 6.46 | 8.33 | 8.20 | 7.15 |
| 305.5 | 8.88 | 6.67 | 8.78 | 8.60 | 7.75 |

FIG. 18 is a graph illustrating an example of a filter media resistivity measured by direct electrical contact versus total fluid throughput during an operation of a filter. As illustrated in FIG. 18, plot 180 includes a horizontal axis representing gallons filtered during operation of a filter and a vertical axis representing measured filter media resistivity in ohms-centimeters. In the example of FIG. 18, approximately 305 gallons of water containing approximately two parts per million of chlorine was filtered in three activated carbon filters of a substantially similar construction. In FIG. 18, curves 182 and 190 correspond to two separate example filters, each including one sensor having a set of four metal probes positioned in the center of the longitudinal axis of the filter media. Also, in the example of FIG. 18, curves 184, 186, and 188 correspond to a single experimental filter, having three separate sensors, each sensor including a set of four metal probes: Curve 184 corresponds to the sensor positioned near a top of the single experimental filter; Curve 186 corresponds to the sensor positioned near a center of the longitudinal axis of the single experimental filter; and Curve 188 corresponds to the sensor positioned near a bottom of the single experimental filter.

The following table presents the experimental results illustrated in FIG. 18:

| | Filter | | | | |
|---|---|---|---|---|---|
| Gallons Filtered | 182 ($\Omega \cdot cm$) | 190 ($\Omega \cdot cm$) | 184 ($\Omega \cdot cm$) | 186 ($\Omega \cdot cm$) | 188 ($\Omega \cdot cm$) |
| 0.0 | 18.06 | 12.12 | 15.21 | 14.71 | 12.80 |
| 1.3 | 16.66 | 11.11 | 13.86 | 13.52 | 12.12 |
| 3.3 | 15.94 | 10.75 | 13.40 | 12.94 | 11.76 |
| 6.5 | 15.33 | 10.41 | 13.04 | 12.56 | 11.59 |
| 9.8 | 15.21 | 10.38 | 12.99 | 12.39 | 11.47 |
| 13.0 | 14.73 | 10.17 | 12.82 | 12.32 | 11.16 |
| 19.5 | 14.61 | 10.14 | 12.75 | 12.32 | 11.25 |
| 26.0 | 14.56 | 10.14 | 12.80 | 12.56 | 11.35 |
| 32.5 | 14.49 | 10.14 | 12.80 | 12.56 | 11.35 |
| 39.0 | 14.68 | 10.14 | 12.80 | 12.75 | 11.54 |
| 48.8 | 14.68 | 10.22 | 13.04 | 12.85 | 11.54 |
| 55.3 | 14.78 | 10.26 | 13.11 | 12.80 | 11.59 |
| 61.8 | 14.90 | 10.43 | 13.26 | 12.85 | 11.79 |
| 78.0 | 14.92 | 10.43 | 13.43 | 12.92 | 11.88 |
| 97.5 | 15.70 | 11.11 | 13.91 | 13.72 | 12.51 |
| 136.5 | 16.18 | 12.56 | 15.00 | 14.51 | 12.94 |
| 156.0 | 16.64 | 12.92 | 15.89 | 15.65 | 13.43 |
| 175.5 | 17.24 | 13.74 | 16.49 | 16.40 | 13.81 |
| 195.0 | 18.31 | 14.18 | 18.06 | 17.29 | 15.29 |
| 273.0 | 20.38 | 15.60 | 20.12 | 19.80 | 17.27 |
| 305.5 | 21.44 | 16.11 | 21.20 | 20.77 | 18.72 |

Figure 19:
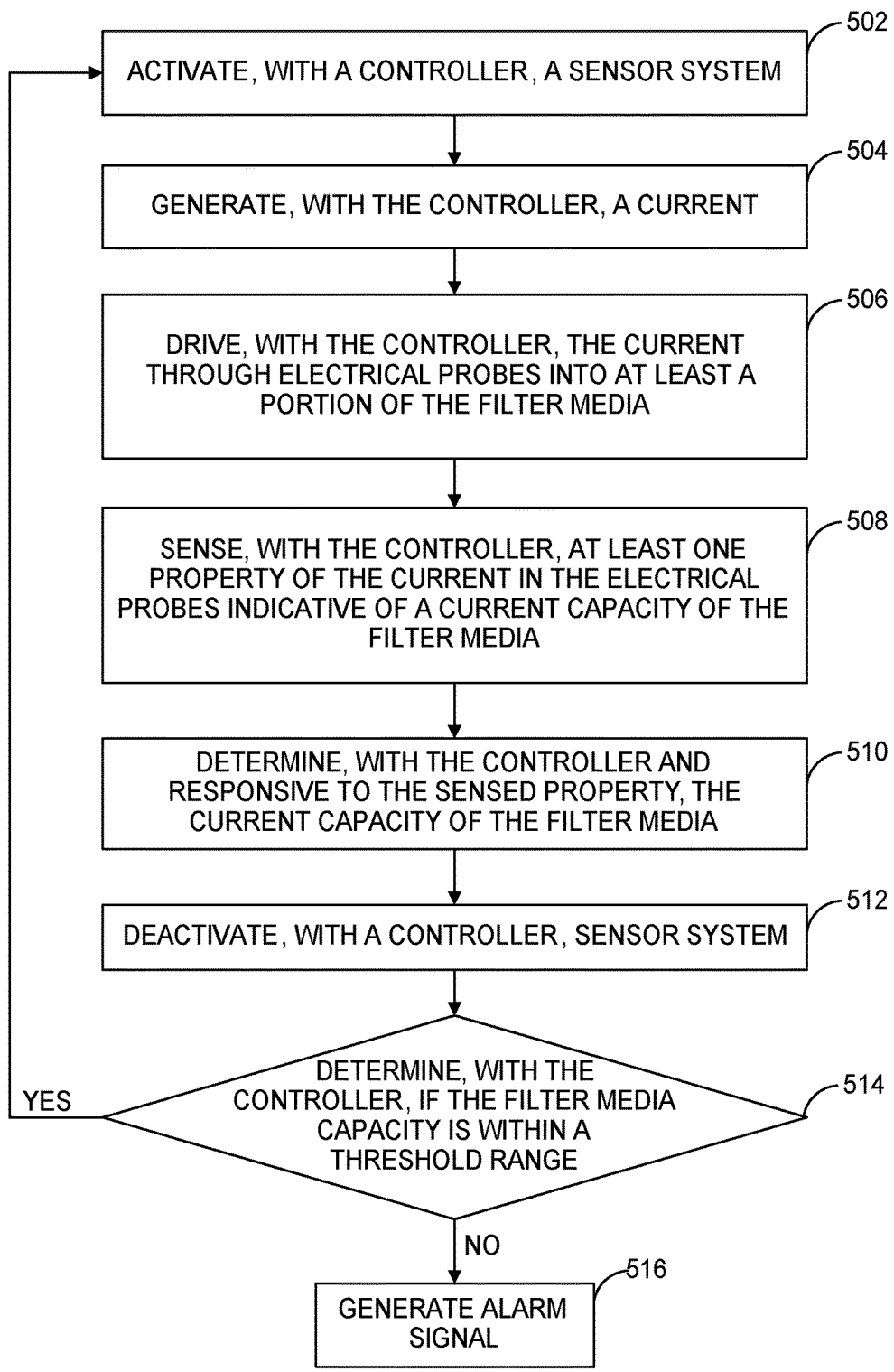
FIG. 19 is a flow diagram illustrating an example technique for monitoring a filter media using a direct contact sensor system.

FIG. 19 is a flow diagram illustrating an example operation of a sensor having direct electrical contact probes for monitoring a filter media. For purposes of example, FIG. 19 is described with respect to the components of sensor 50 shown in FIG. 4. Various filtration systems and filter configurations may be used with the techniques of FIG. 19, which are described, for purposes of illustration, with respect to sensor 158 of FIG. 16. However, it will be understood that the techniques of FIG. 19 may be performed for a different sensor system or filter and sensor configuration, and that utilizing a sensor system may include other techniques.

In the example of FIG. 19, controller 56 within sensor 158 initiates a sensing cycle (502). In some examples, controller may activate the sensor system at a predetermined time interval. In some examples, the controller may activate the sensor system by user input (e.g., pressing reset/test button 162), automated input from an external device (e.g., a signal from a separate controller, or the like).

In the example of FIG. 19, the controller generates an electrical current (504) and drives the current via the electrical probes into at least a portion of a filter media 156 (506). In some examples, the controller drives the current into probes external to an outer surface of filter housing 156 so as to induce a current in corresponding probed internal to an inner surface of filter housing 156.

Next, the controller senses at least one property of the current indicative of a capacity of the filter media 156 (508). For example, as described above, based on the applied voltages and resultant current through the set of electrical probes, controller 56 may measure a respective resistivity of one or more regions of the filter media. In addition, controller 56 may monitor other properties of the environment or water filtration system (e.g., temperature, fluid flow rate) and utilizes the measured properties to compensate or adjust the computed estimate for the remaining capacity of filter media 156. Based on the sensed properties of the media and any sensed properties for the environment of the water filtration system, controller 56 computes the current capacity of the filter media 156 and updates user interface 54 (510).

Based on the computed capacity of the filter media, controller 56 may in some examples determine whether the filter media 156 capacity is within a threshold range. If the estimated capacity of filter media 156 is determined to be within the threshold range, the controller 56 repeats the sensing cycle at a future time or asynchronously in response to input from a user or external monitoring component (YES branch of 514, go to 502). In the event the capacity of filter media 156 is determined to not be within the threshold range, such as below 10% capacity remaining, controller 56 generates an alarm signal or other output, e.g., electronic communication (NO branch of 514, go to 516). In some examples, the alarm signal may be presented by a user interface as, for example, a visual alarm, an audible alarm, or the like. In other examples, the alarm signal may be transmitted by a radio frequency transmitter.

Figure 20:
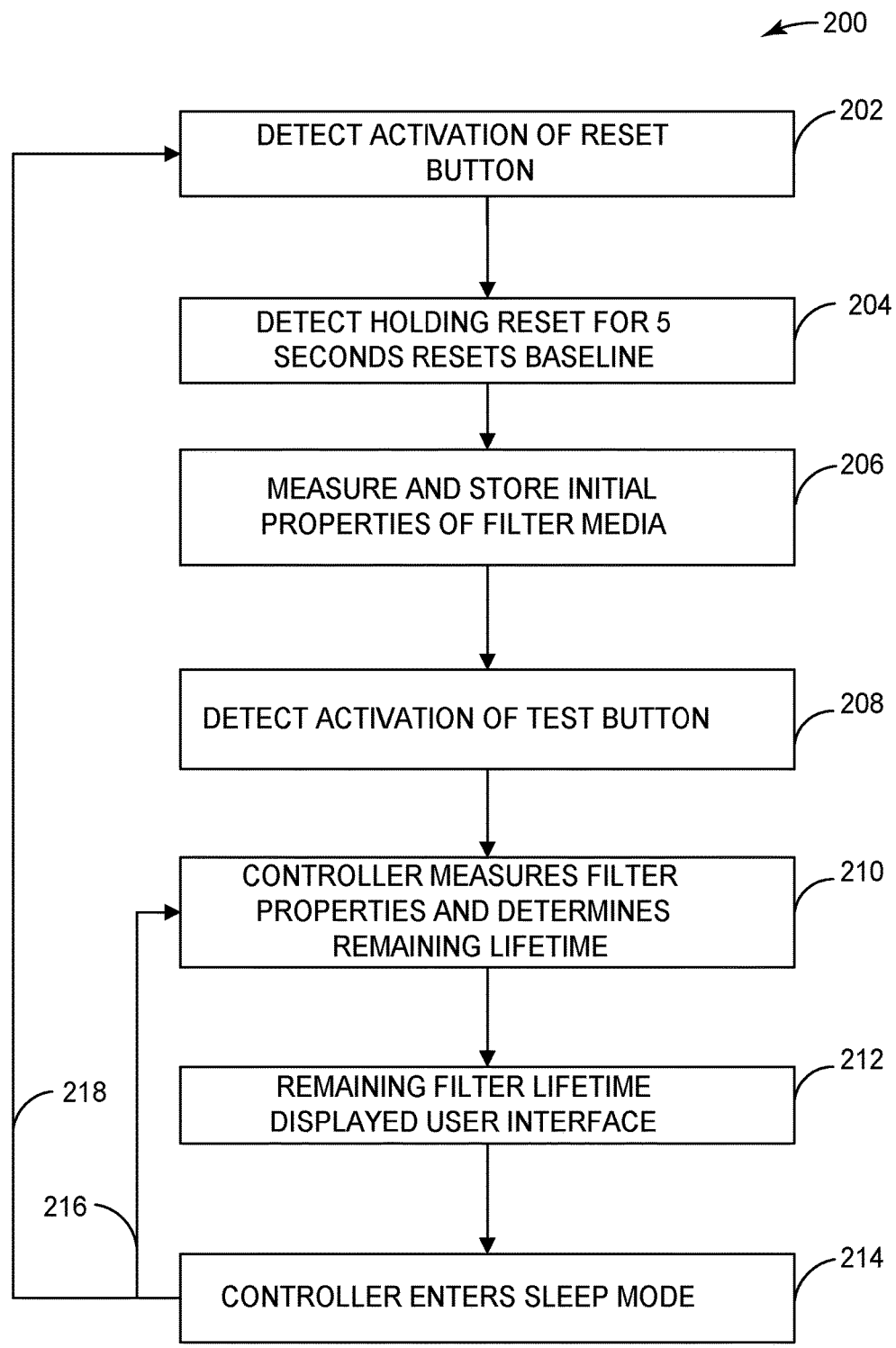
FIG. 20 is a flow diagram illustrating example operation of a sensor as described herein when a filter media is first installed within a filtration system.

FIG. 20 is a flow diagram illustrating example operation of a sensor as described herein when a filter media is first installed within a filtration system. Various filtration systems and filter configurations may be used with various techniques described in this disclosure. For purposes of example, the process of FIG. 20 will be described with respect to sensor 20 of FIG. 2, sensor 50 of FIG. 4, for purposes of illustration.

In general, the process of FIG. 20 may be initiated at various situations, such as upon installation of a new filter, upon inspecting the sensor and determining a reset is needed, up changing the position of an existing filter or changing a position of an existing sensor within a filtration system, or the like. In a situation such as these, controller 56 senses activation of reset/test button 22 (202) and, in particular, determines that the input is indicative of a user holding the reset/test button 55 for a threshold period (e.g., five seconds), thereby requesting reset of baseline readings of the sensor 20 (204).

At this time, controller 56 performs an initial measurement cycle, using the various techniques described herein, to measure and store one or more initial properties of the filter media and/or any antennae or resonant cavity utilized in the sensing system, thereby performing a baseline reading (206). For example, controller 56 may measure and initially store parameters related to resistivity, inductance, capacitance, resonant frequency, quality factor, or equivalent series resistance, equivalent parallel resistance of the sensing system.

Thereafter, activation of the reset/test button 22 powers-on the controller 56 (208) and causes controller 56 to initiate a sensing cycle using any of the various techniques described herein (210). As described, controller computes the remaining lifetime or the remaining capacity of the filter media and updates user interface 24 or otherwise communicates the results to a user of external system (212). Controller 56 may then enter a sleep mode and after lapse of a predetermined time interval, wake and automatically repeat the process of measuring the filter media (216). Moreover, responsive to activation of the reset/test button 22, controller 56 wakes from sleep mode and repeats the reset process of in the event the reset button 22 is depressed for the threshold period of time (218).

Figure 21:
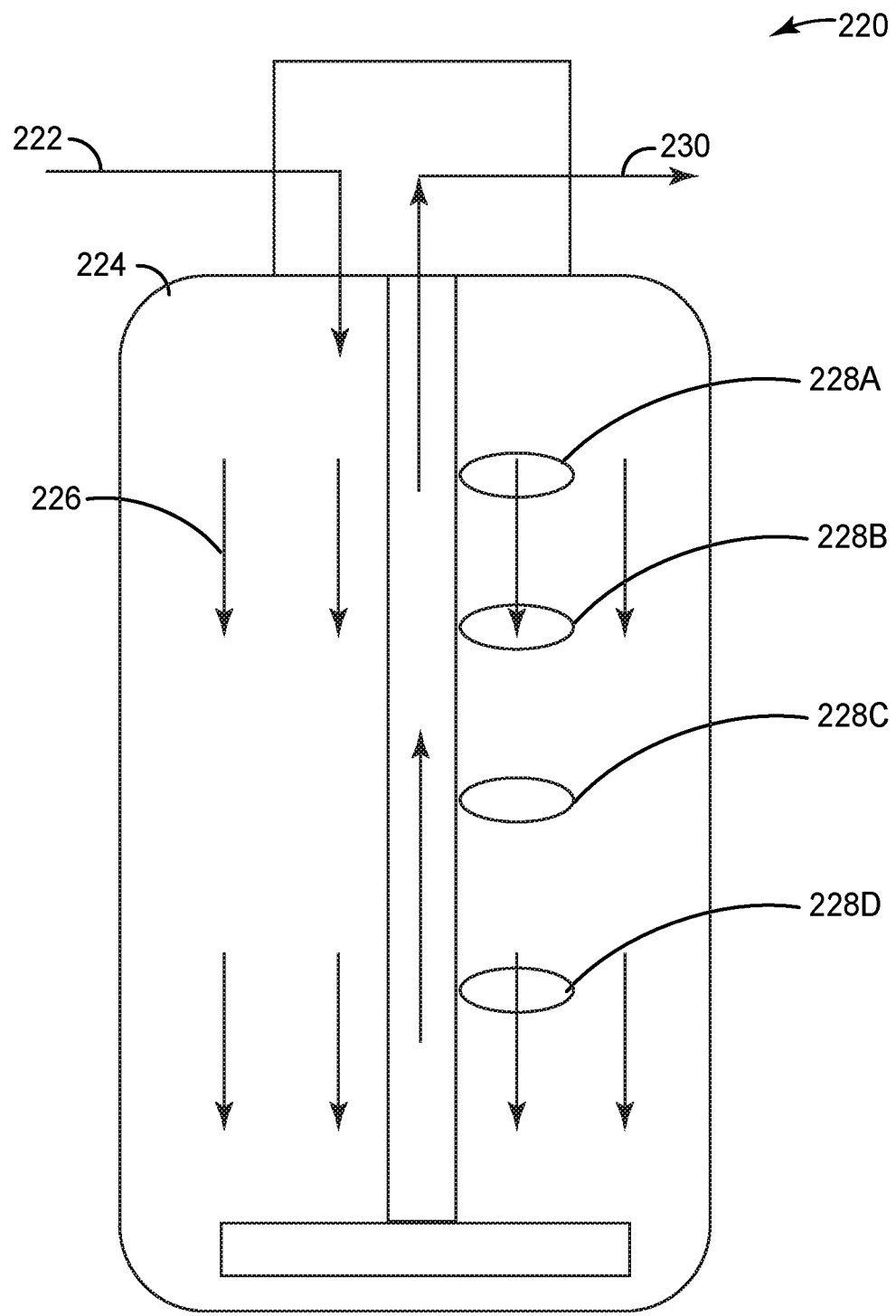
FIG. 21 is a schematic diagram illustrating an example filter housing and sensor system comprising a plurality of filter media sensors positioned in series with respect to the flow direction within the filter media.

FIG. 21 is a schematic diagram illustrating an example filter housing and sensor system comprising a plurality of sensors positioned in series with respect to the flow direction within a filter media. In the example of FIG. 21, sensor system 220 includes fluid inlet 222, filter housing 224, a plurality of sensors 228A, 228B, 228C, 228D (collectively, "sensors 228"), and fluid outlet 230. In the example of FIG. 21, the flow direction 226 indicates the path of fluid travel. In some examples, sensors 228 may be positioned in series with respect flow direction 226 throughout a filter media. In some examples, the sensors 228 may be in magnetic communication with the filter media so as to determine the filter media lifetime or capacity, using the techniques as discussed above. In other examples, the sensors 228 may be in direct electronic communication with the filter media so as to determine the filter media lifetime or capacity, using the techniques as discussed above. In some examples, sensor system 220 may include fewer (e.g., one, two, three) or more (e.g., ten, one hundred, one thousand) sensors.

As described herein, the arrangement of sensors 228 allows differential sensor measurements to be utilized to eliminate or minimize environmental effects that could otherwise be a source of error in single sensor measurements, such as sensor dependency on temperature, humidity, flow rate, pressure drop, drift in electronic components, baseline instability, sensor drift, secondary effects on filtration media. The plurality of sensors 228 can be connected to filtration media with a parallel, series, or combination fluid flow patterns. Moreover, the entire set of sensors 228 for which measurement information is exchanged and utilized in determining filter capacity need not be affixed to the same filter media. For example, multiple filtration elements may be connected in a series flow pattern spanning multiple, discrete filter media and the measurements from at least some of those sensors may be utilized by other sensors when computing filter capacity.

In this way, a plurality of sensors 228 can be used to monitor spatiotemporal efficacy of filtration media, enabling monitoring of the breakthrough front through the filtration media. In one example, a plurality of sensors located along the fluid flow direction of a pack-bed filtration system can be used to monitor the filter efficacy along the flow direction. In a second application, a plurality of sensors designed to interact with the filtration media a various depths into the filter block can be used to determine filter efficacy along the flow direction. In a third example, two sensor can be located on the outer and inner surfaces of a carbon block filter, and through monitoring both sensors the relative efficacy of the filtration media along the flow direction can be determine. The ability to monitor the spatiotemporal efficacy of the filtration media can be used to improve a replacement algorithm for the filtration media, enabling the filtration media to be used to its entire capacity. This may, in turn, reduce cost associated with filtration, reduce the cost associated with servicing, and reduce waste associated with the filtration system.

In some examples, a plurality of sensors can be used to monitor filters having multiple layers of filtration media. For example, a filter may contain two concentric filtration media layers with an outer pleated layer and an inner carbon layer. One sensor can be positioned and configured to measure a dielectric change in the pleated layer and a second sensor can be positioned and configured to measure the conductivity change in the carbon filter.

Sensors 228 may be positioned and configured to utilize any of the sensing techniques described herein and may measure filter media conductivity, dielectric strength, magnetic permeability, and the like. In some examples, a breakthrough of an impurity, chemical compound, or the like, can be determined by a differential measurement of two or more of sensors 228. In some examples, the differential of two or more sensors 228 may negate potential variability between individual sensors by, for example, temperature variation, drifts in conductivity, variation in filter media composition, or the like.

In some examples, sensors 228 may communicate with a common external monitor (not shown) that communicates with, for example, an operator, service provider, or the like. For instance, in the example of FIG. 21, as the breakthrough front is detected in sensor 228C, the system can predict when the breakthrough front will reach 228D. In such an example, the monitor may communicate directly with service provider to schedule filter media change out, notify an operator of the expected filter change time, order replacement filter media, or the like.

In some examples, sensors 228 may be identified as individual and distinct sensors. In some examples, individual sensors 228A, 228B, 228C, 228D may generate distinct radio frequencies to identify each sensor individually based on a respective spectral signature. In other examples, multiple antennas (not shown) may be positioned relative to a respective sensor whereby the positioning may allow the antenna to interface with a specific sensor. In yet other examples, individual sensors 228A, 228B, 228C, 228D may operate near a frequency (e.g., 13.56 MHz) that enables a radio frequency identification device integrated circuit (RFID IC), whereby the RFID IC on the individual sensor enables individual sensor read outs. In some examples, an authentication chip, code, magnetic signature, or the like, provided with the replacement filter may automatically reset the monitor to record a baseline (e.g., baseline filter media conductivity, dialectic strength, or magnetic permeability) and confirm installation of the proper filter. For example, if the new filter was not validated, the sensor will not reset.

Figure 22:
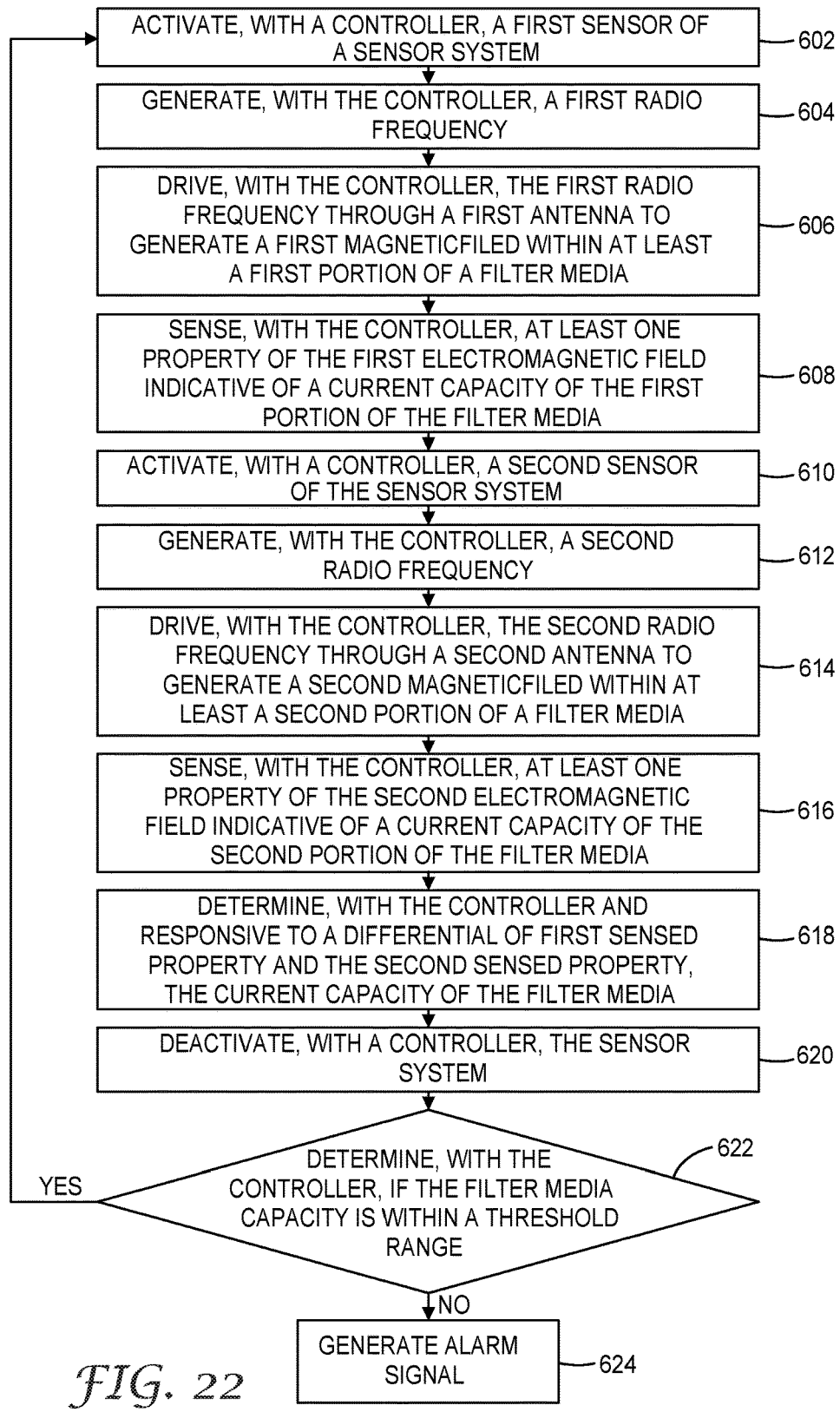
FIG. 22 is a flow diagram illustrating an example operation of a sensing system in which a plurality of sensors exchange information and operate to monitor a filtration system having one or more filter media.

FIG. 22 is a flow diagram illustrating example operation of a sensing system in which a plurality of sensors exchange information and operate to monitor a filtration system having one or more filter media.

In the example of FIG. 22, a first sensor 228A of sensor system 220 is activated by a controller to initiate a sensing cycle (602). In some examples, the controller may activate the sensor system at a predetermined time interval. In some examples, the controller may activate the sensor system by user input (e.g., pressing a reset/test button), automated input from an external device (e.g., a signal from a separate controller), or the like. In the example of FIG. 22, the controller generates a first radio frequency ("RF") signal (604). In some examples, the RF signal may be a resonant frequency of a first antenna associated with sensor 228A. In other examples, the RF signal may be the resonant frequency of the first antenna when located proximate to a particular portion of a filter media of sensor system 220. In the example of FIG. 22, the controller drives the first RF signal through the first antenna to generate a first electromagnetic field within at least a first portion of the filter media (606). In the example of FIG. 22, the controller senses at least one first property of the first electromagnetic field indicative of a current capacity of the first portion of the filter media such as, for example, inductance, capacitance, resonant frequency, quality factor, equivalent series resistance, equivalent parallel resistance, or the like (608). The controller communicates the measured property to one or more other sensors (e.g., sensor 228B) or to a centralized monitor coupled to the sensors.

In the example of FIG. 22, second sensor 228B of sensor system 220 is activated by a controller associated with that sensor or by the external monitor (610). In the example of FIG. 22, the controller performs the second sensing cycle by generating a second radio frequency ("RF") signal (612) and driving the second RF signal through the second antenna to generate a second electromagnetic field within at least a second portion of the filter media (614), where the second portion may separate from, overlap with or encompass the first portion of the filter media. In the example of FIG. 22, the controller senses at least one second property of the second electromagnetic field indicative of a current capacity of the second portion of the filter media such as, for example, inductance, capacitance, resonant frequency, quality factor, equivalent series resistance, equivalent parallel resistance, or the like (616). The controller of the second sensor may communicate the measurements to a centralized monitor.

Next, the controller of the second sensor (or the centralized monitor) determines the current capacity of the filter media (618). In some examples the controller of the second sensor determines the current capacity of at least the second portion of the filter media based on a differential between the first sensed property and the second sensed property (618). Alternatively, or in addition, the controller of the second sensor (or the centralized monitor) may adjust or otherwise bias the second sensed property based on the first sensed property to determine the current capacity of the second portion of the filter media. In the example of FIG. 22, the controllers deactivates sensors 228A and 228B by powering down one or more components of sensors 228A and 228B (620).

As described herein, the controllers associated with the sensors, or the external monitor, determines if the filter media capacities with the first portion and the second portion are within a threshold range (622). If the filter media capacities are within the threshold range, then the controllers (or central monitor) activate sensors 228A and 228B at some future time (YES branch of 622, 602) to repeat the process. If either or both of the filter media capacity is not within the threshold range, then the controllers and/or central monitor generates an alarm signal (NO branch of 622, 624). In some examples, the alarm signal may be presented by user interface 54 as, for example, a visual alarm, an audible alarm, or the like. In other examples, the alarm signal may be transmitted by radio frequency transmitter 70. In example implementations, sensing systems are described that provide automated identification for the filter media currently deployed within a filtration system. For example, in some implementations, non-contact identification bands may be incorporated within or otherwise affixed proximate the housings containing the filter media. As described herein, the identification bands may be constructed so as to influence the magnetic sensing of the filter media by a sensor mounted on the housing. For example, the identification bands may be electrically conductive and/or magnetic so as to be sensed by the sensor. Moreover, the bands may be geometrically or spatially arranged so as to provide a unique identification of the filter media, such as when the filter media in inserted into the filtration system and passed through a sensing field of the sensor. In this way, the identification bands may be utilized to provide an affirmative identification of the filter media.

Figure 23:
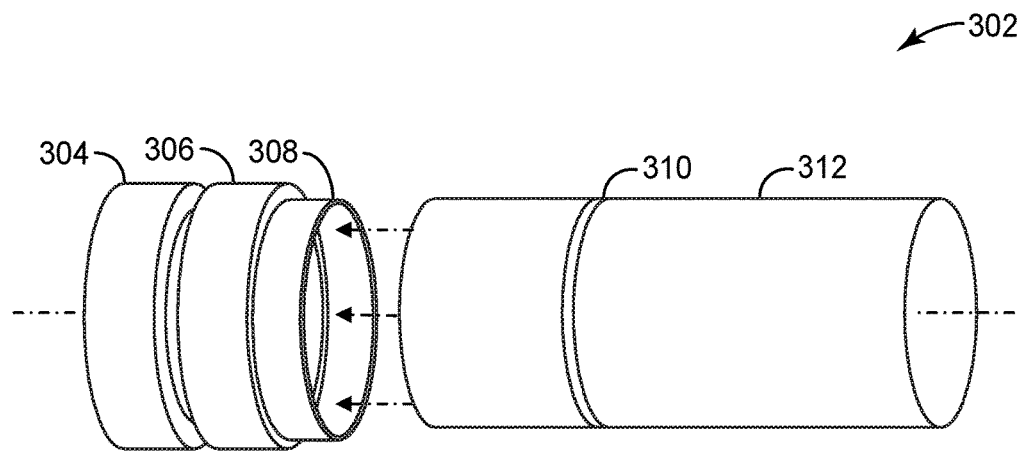
FIG. 23 is a schematic diagram illustrating an example filter housing identification system.

FIG. 23 is a schematic diagram illustrating an example filter housing identification system. In the example of FIG.

23, filter identification system 302 includes filter manifold 304, filter manifold coupling member 306, sensor 308, identification strip 310, and filter housing 312. In some examples, identification strips are conductive, dielectric, or magnetic regions disposed on, disposed within, or contained within the filter housing. In some examples, an identification strip may include a single or any combination of conductive, dielectric, or magnetic regions that modify the antenna properties and may be sensed by the filter identification system.

In general, filter manifold 304 represents a portion of a filter system, where filter manifold coupling member 306 connects the filter manifold to filter housing 312 being inserted into the filtration system. In some examples, filter manifold 304 and filter manifold coupling member 306 may be a nonconductive material such as, for example, plastic, glass, porcelain, rubber, and the like. In other examples, filter manifold 304 may be a conductive material such as, for example, metals, conductive polymers, and the like. In some examples, filter manifold 304 may be formed so as to encompass a sensor (not shown) and/or the sensor 308.

In the example of FIG. 23, sensor 308 is affixed to the filter manifold coupling member 306 that receives filter housing 312. Sensor 308 may take the form of any of the sensors described herein. In example implementations, sensor 308 includes an antenna having a wound conductive wire that encompasses filter housing 312 when the filter housing 312 is inserted. In the example of FIG. 23, sensor 308 drives its internal antenna to create an electromagnetic field in electromagnetic communication with identification strip 310 as the filter housing is inserted into the filter manifold coupling member 306 (e.g., as indicated by the arrows in FIG. 23). In some examples, the antenna of sensor 308 may be in electromagnetic communication with identification strip 310 and at least a portion of a filter media and optionally other non-filtering media designed to influence the magnetic field.

In various implementations, identification strip 310 conforms to a specific physical shape or dimension so as to shape the magnetic field produced by the antenna of the sensor system. For example, identification band may be constructed such that, in the presence of the magnetic field, the identification band varies the spatial sensitivity of the sensor system, directs the magnetic field toward or away from a region of the filter housing, filter manifold, or other sensor system elements, enhances the magnetic field propagation through the filtration media contained within the filter housing or causes similar effects detectable by the sensor.

In some examples, identification strip 310 may be a conductive material such as, for example, metals, conductive polymers, and the like. In other examples, identification strip 310 may be a magnetic material such as, for example, iron, nickel, ferrite, and the like. In other examples, identification strip 310 may include both a conductive material and a magnetic material, as described above. In some examples, identification strip 310 may include geometric patterns to visually and/or electronically indicate authenticity or origin. In some examples, one or more identification strips 310 may be spatially located on the filter housing and configured to modify (i.e., influence) one or more properties of the electromagnetic field generated by the antenna of the sensor. As described herein, responsive to detecting the modification to the electromagnetic field, the controller within the sensor affixed to the housing is able to determine a spatial proximity of identification strip 310 relative to the antenna of the sensor. As such, the controller may determine and provide output indicative of whether, based on the precise spatial proximity, the filter housing is correctly inserted into the filter manifold, thereby aiding the operator to ensure correct flow rates and minimize the potential for fluid leaks or enable and disenable a flow valve.

In some examples, based on the detected effects of the one or more identification strips 310, the controller within the sensor may electronically classify the filter when inserted into the filter manifold to, for example, ensure the inserted filter is designed to for the correct fluid type, ensure contamination removal, verify treatment volume rating, verify contamination removal efficacy rating, verify rated flow rate, verify rated operational pressure, or verify compatibility of anti-leak design. In other examples, identification strip sensing may enable a correct lifetime algorithm and notify the user when the filtration media should be changed.

In some examples, identification strip 310 may include a plurality of strips (e.g., two strips, 10 strips, 20 strips), and the strips may be uniformly spaced or spaced in a unique geometric pattern to aid identification of the particular type of filter media housing 312 and the filter media contained therein. In some examples, identification strip 310 may be positioned on an exterior of filter housing 312. In other examples, identification strip 310 may be positioned within a material defining filter housing 312. In other examples, identification strip 310 may be positioned on an interior of filter housing 312. In some examples, identification strip 310 may have one or more geometries (e.g., each strip of identification strip 310 may have a unique geometry).

In the example of FIG. 23, identification strip 310 extends around an entire circumference of filter housing 312. In some examples identification strip 310 may extend around less than an entire perimeter of filter housing 312. For example, as demonstrated by experimental results of Table 2, a resonant frequency, parallel resistance, and q-factor of an antenna and a conductive identification strip may vary depending on identification strip length around a circumference of a cylindrical filter housing. Table 2 illustrates the cases where a conductive identification band is not present, is a segment length of approximately one quarter of a filter housing circumference, is a segment length of approximately one half of a filter housing circumference, is a segment length of approximately three-fourths of a filter housing circumference, and is a segment length of approximately a filter housing circumference. As demonstrated by the example in Table 2, the presence of a conductive identification band on a filter housing may be detected by sensing resonant frequency shifts and an identification band length may be configured so as to cause a specific magnitude of the frequency shift. These examples illustrate that a conductive identification band positioned on a filter housing can be utilized to identify a filter housing, such as when the filter housing is inserted into the filtration system.

TABLE 2

| Identification Band Length | Resonant Frequency [MHz] | Resistance [Ω] | Q-Factor |
|---|---|---|---|
| No Band | 9.2725 | 282.2 | 64.4 |
| ¼ Filter Housing Circumference | 9.3000 | 278.0 | 63.6 |
| ½ Filter Housing Circumference | 9.3280 | 271.2 | 62.2 |
| ¾ Filter Housing Circumference | 9.3440 | 267.8 | 61.4 |
| Full Filter Housing Circumference | 9.3880 | 257.0 | 60.0 |

In some examples, a configuration of identification strip 310 material, position, geometry, number of strips, or the like, may uniquely identify a filter family, a filter family subcategory, a specific filter type, or the like. In some examples, the sensor may store in a memory a record of identification strips of installed filter housing so as to, for example, prevent a used filter from being reinstalled, to mandate a standard operating procedure for changing filters, or the like.

FIG. 30A, 30B, 30C, 30D are schematic diagrams illustrating a series of positions of a filter housing over time as the filter housing is inserted into a filter manifold. FIG. 31 is a graph illustrating example sensed antenna resonant frequency over time for the filter housing insertion process depicted in FIGS. 30A-30D. In FIG. 31, plot 750 includes a horizontal axis representing time and a vertical axis representing resonant frequency of the antenna of sensor 708 of a sensor system. Curve 760 represents the change or shift in resonant frequency of the antenna of sensor 708 as a filter housing having a conductive identification strip 710 and a magnetic identification strip 714 is installed in a filter manifold 704.

As shown in FIG. 30A-D and FIG. 31, conductive identification strip 710 and magnetic identification strip 714 cause a time dependent change in properties of the magnetic field created by the antenna of sensor 708 when filter housing 712 is inserted into filter manifold 704 so as to pass identification strips 710, 714 proximate to the antenna of sensor 708. By detecting and correlating the specific effects on the electromagnetic field to data describing know, pre-configured arrangements and constructions of identification strips, a controller within sensor 708 is able to affirmatively uniquely identify the type of filter being inserted. For example, as separation between identification strips 710, 714 and the antenna of sensor 708 decrease or increase during filter housing 712 insertion, a change in antenna properties of sensor 308 can be real-time monitored by a sensor system such that a shape and a scale of a time-dependent antenna property identifies a specific filter housing 712. In some examples, the shape and the scale of the time-dependent antenna property may be pre-configured to identify a family of filters (i.e., a type of filter) or a sub-family of filters. The controller of sensor 708 detects and compares the sensed change in a resonant frequency of the antenna (e.g., a profile of discrete data representative of the graph illustrated in FIG. 31) to stored data sets describing profiles for of antenna resonant frequency shifts due to different, identification strips associated with different types of filters. In the example of FIG. 30, an identification process is depicted over four sequential time periods corresponding to FIG. 30A, FIG. 30B, FIG. 30C, FIG. 30D.

Figure 30A:
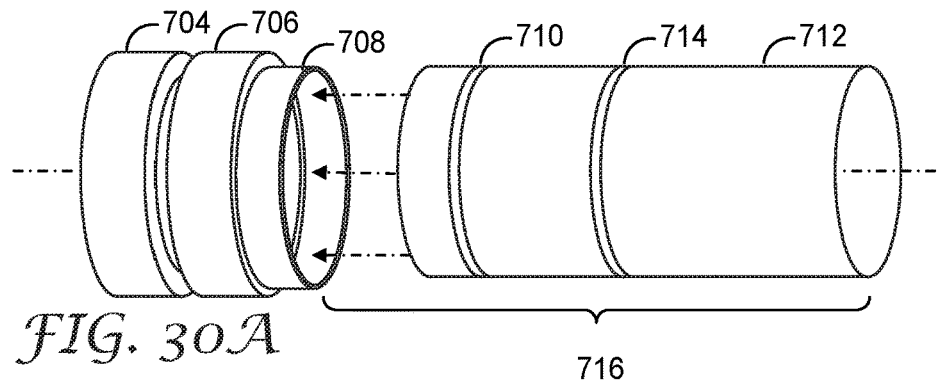
FIGS. 30A, 30B, 30C, 30D are schematic diagrams illustrating a series of positions as a filter housing over time when inserted into a filter manifold.
Figure 31:
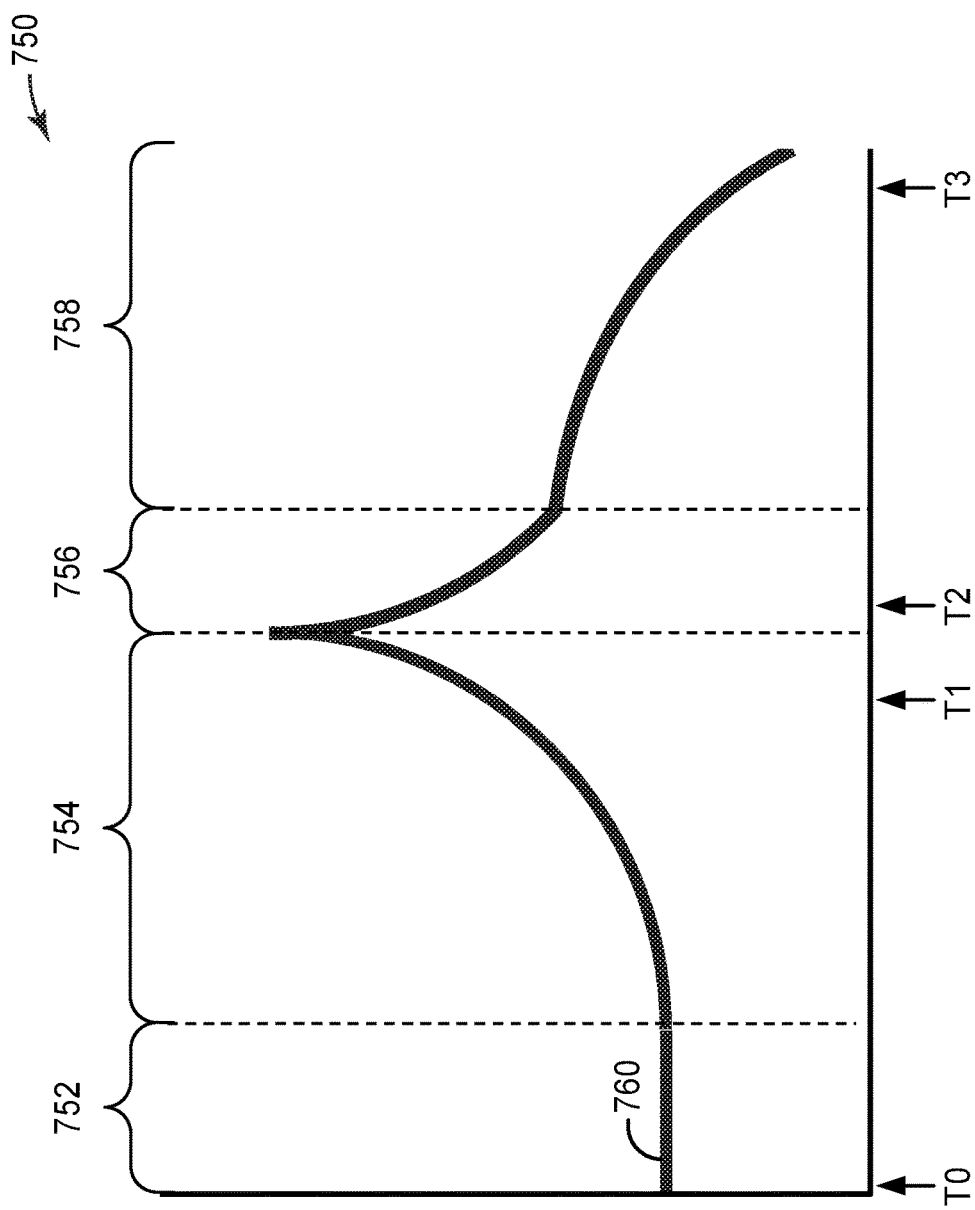
FIG. 31 is a graph illustrating an example of a sensed change in an antenna resonant frequency for the filter housing insertion process of FIGS. 30A-30D.

In FIG. 30A, at time T0 and distance 716 between the antenna of sensor 708 and the end of filter housing 712, the separation between the antenna of sensor 708 and identification strips 710, 714 is large enough such that there is a negligible change in resonant frequency of the antenna of sensor 708. In some examples, a large separation between identification strips 710, 714 and the antenna of sensor 708 results in no near-field interaction.

Figure 30B:
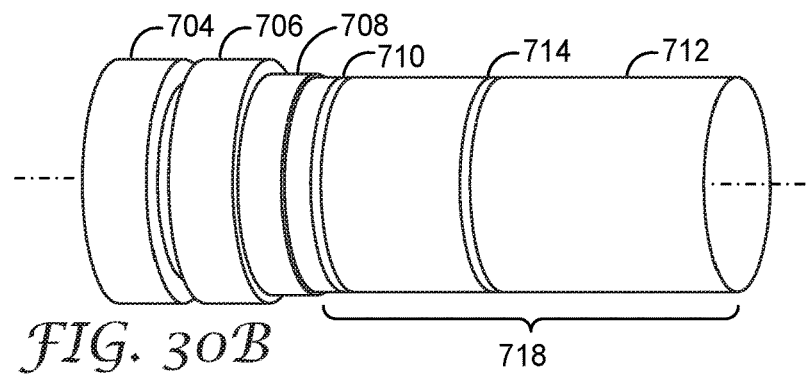

In FIG. 30B, at time T1 and distance 718 between the antenna of sensor 708 and the end of filter housing 712, the separation between the antenna of sensor 708 and conductive strip 710 is decreasing as the filter housing is inserted and has become sufficiently small such that near-field coupling occurs between the identification strips 710 and the antenna, thus leading to an increase in resonant frequency of the antenna of sensor 708 due to the conductive strip 710.

Figure 30C:
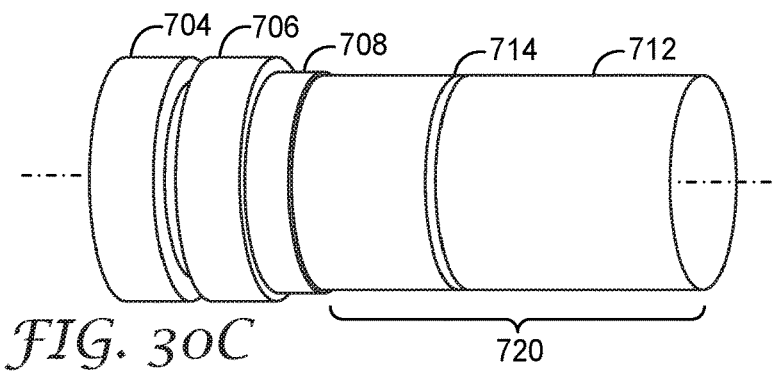

In FIG. 30C, at time equal to T2 and distance 720 between the antenna of sensor 708 and the end of filter housing 712, the separation between the antenna of sensor 708 and conductive strip 710 is now decreasing as the conductive strip has passed by the antenna of sensor 708, resulting in a peak in resonant frequency followed by a decrease in resonant frequency of the antenna of sensor 708. In some examples, conductive band 710 moves away from the antenna of sensor 708 resulting in a change in one or more properties of the antenna of sensor 708. In the example of FIG. 30C, the separation between the antenna of sensor 708 and magnetic strip 714 is still large enough to result in a negligible change in resonant frequency of the antenna of sensor 708 due to the magnetic strip 714.

Figure 30D:
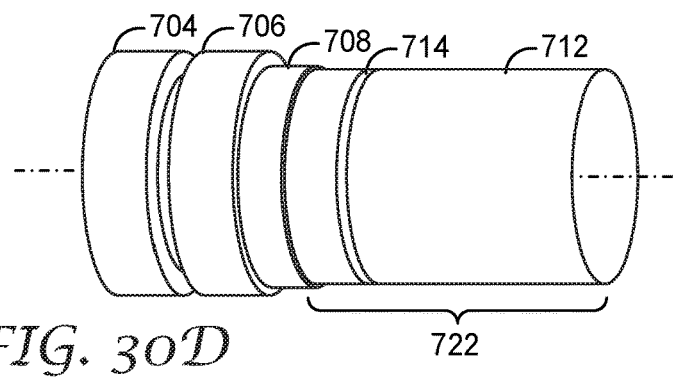

In FIG. 30D, at time T3 filter housing 712 has been fully inserted. In this position, the separation between the antenna of sensor 708 and conductive strip 710 is large enough such that negligible near-field coupling occurs, causing negligible change in resonant frequency of the antenna of sensor 708. Also in this position, the separation between the antenna of sensor 708 and magnetic strip 714 is near-field coupling to the antenna of sensor 708, causing a decrease in resonant frequency of the antenna of sensor 708.

In this way, FIGS. 30A-30D and FIG. 31 illustrates that changes to sensing antenna resonant frequency over time during insertion of a filter housing with a conductive and/or magnetic identification strips may be used to sense a time-dependent modification of the properties of the electromagnetic field in a way that is unique to a particular configuration of the conductive and/or magnetic identification strips. A controller of sensor 708 (or an external monitor) validates an identification strip by comparing the sensed shifts in one or more antenna properties with a stored data set of shifts (e.g. a predetermined identification strip resonant frequency shift pattern). In other words, FIGS. 30A-30D, 31 demonstrate that a sensed change or shift in an antenna resonant frequency of a sensor system may be utilized to determine a pattern indicative of a filter family, a filter family subcategory, a specific filter type, or the like. In some examples, a controller of the sensor system may authenticate the identity of the filter family, the filter family subcategory, the specific individual filter, or the like. In some examples, a sensor system may, after authentication, sense an initial position of a filter housing in a filter manifold so at to ensure the filter housing is seated properly.

Figure 32A:
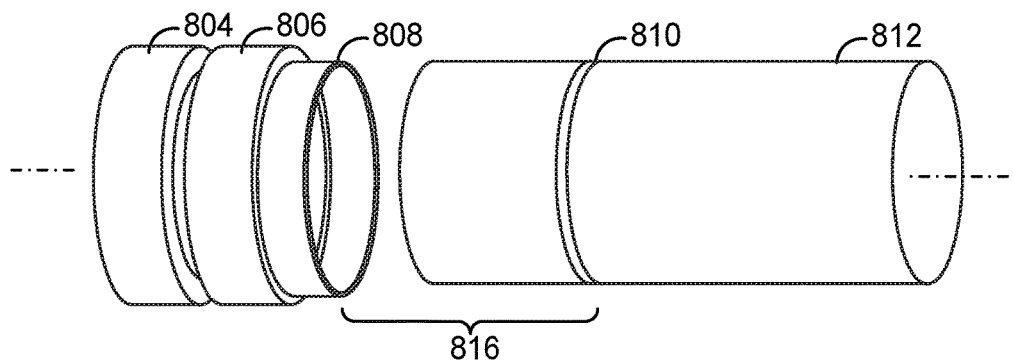
FIGS. 32A, 32B, 32C are schematic diagrams illustrating a series of positions as a filter housing is inserted and seated into a filter manifold.
Figure 32B:
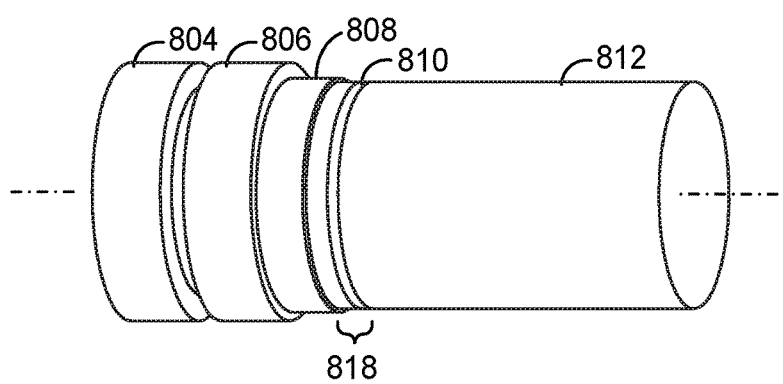
Figure 32C:
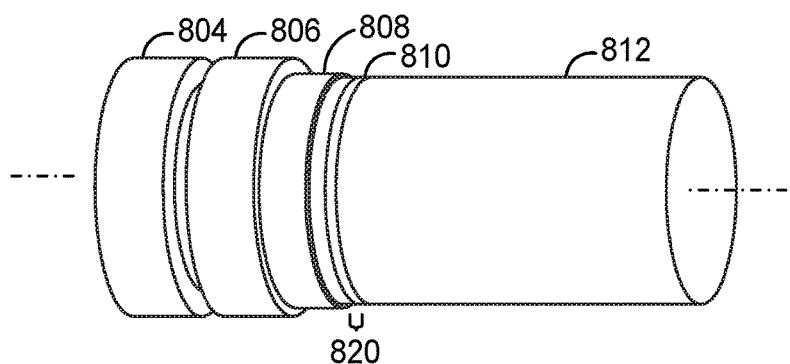

FIGS. 32A, 32B, 32C are schematic diagrams illustrating another example series of positions as a filter housing is inserted and seated into a filter manifold. In the example of FIG. 32, a conductive identification strip 810 cause a time dependent change in properties of the antenna of sensor 808 when filter housing 812 is inserted into filter manifold 804. In some examples, the conductive strip 810 may be a magnetic strip. In other examples, the conductive strip 810 may be a plurality of conductive and/or magnetic strips. In some examples, the time dependent change may be indicative of the filter housing 812 being fully seated into filter manifold 804. In other examples, the time dependent change may be indicative of the filter housing 812 not being fully seated into filter manifold 804.

In the example of FIG. 32A, the distance 816 between the antenna of sensor 808 and the conductive strip 810 is large enough such that there is a negligible change in resonant frequency of the antenna of sensor 808. In the example of FIG. 32B, the distance 818 between the antenna of sensor 808 and the conductive strip 810 is small enough such that there is an increase in resonant frequency of the antenna of sensor 808 due to conductive strip 810, which does not indicate the filter housing 812 is fully seated in filter manifold 804. In the example of FIG. 32C, the distance 820 between the antenna of sensor 808 and the conductive strip 810 is smaller such that there is a further increase in resonant frequency of the antenna of sensor 808 due to conductive strip 810 so as to indicate the filter housing 812 fully seated into filter manifold 804.

Figure 33:
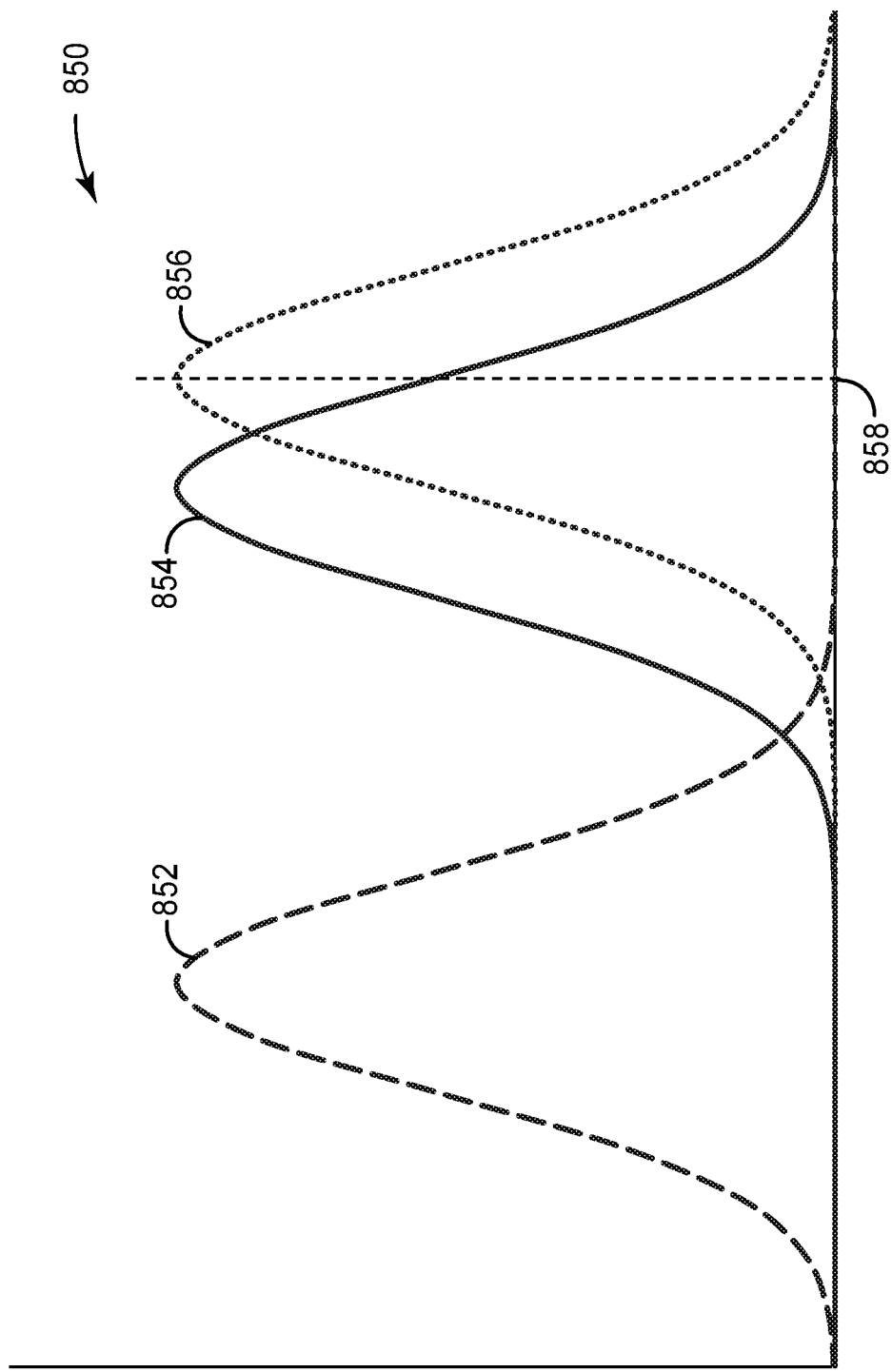
FIG. 33 is a graph illustrating an example of a sensed change in antenna resonant frequency for the filter housing insertion process of FIGS. 32A-32C.

FIG. 33 is a graph illustrating an example of a sensed change in antenna resonant frequency during the filter housing insertion process described above with respect to FIGS. 32A-32C. Various sensor systems and filter configurations may produce various antenna property changes. The graph of FIG. 33 will be described with respect to FIG. 32, for purposes of illustration. However, it will be understood that the graph of FIG. 33 may be represented for a different sensor system or identification strip configuration, and that utilizing a sensor system may include other techniques.

As illustrated in FIG. 33, plot 850 includes a horizontal axis representing resonant frequency of the antenna of sensor 808 and a vertical axis representing signal strength. In the example of FIG. 33, the curve 852 represents a signal strength versus resonant frequency when the distance 816 between the antenna of sensor 808 and the conductive strip 810 is large enough such that there is a negligible change in resonant frequency of the antenna of sensor 808. In the example of FIG. 33, curve 854 represents a signal strength versus resonant frequency when the distance 818 between the antenna of sensor 808 and the conductive strip 810 is small enough such that there is an increase in resonant frequency of the antenna of sensor 808 due to conductive strip 810, which does not indicate the filter housing 812 is fully seated in filter manifold 804. In the example of FIG. 33, curve 856 represents a signal strength versus resonant frequency when the distance 820 between the antenna of sensor 808 and the conductive strip 810 is smaller yet such that there is a further increase in resonant frequency of the antenna of sensor 808 due to conductive strip 810 so as to indicate the filter housing 812 fully seated into filter manifold 804, as indicated by resonant frequency 858.

Figure 24:
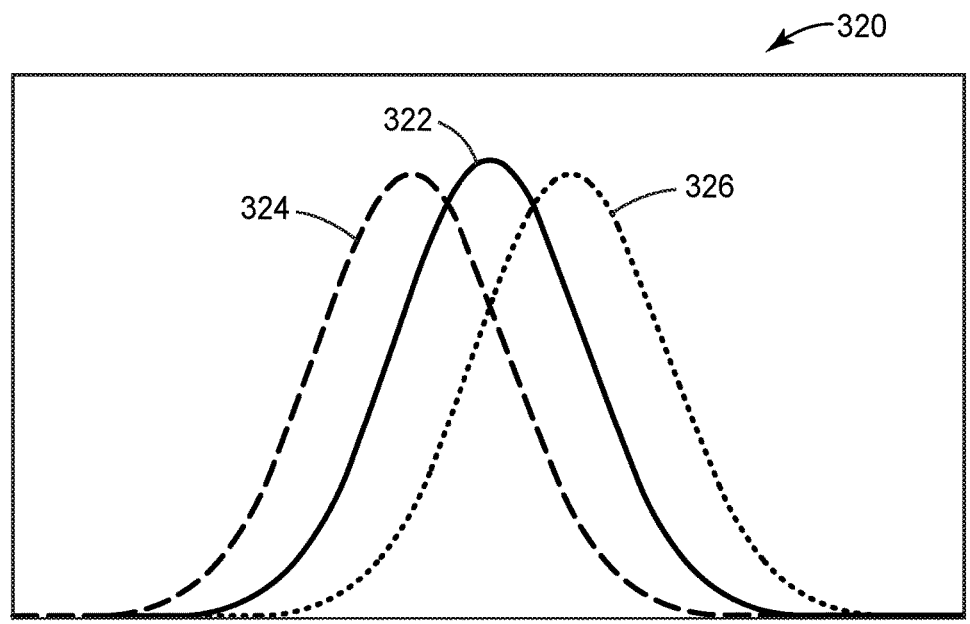
FIG. 24 is a graph illustrating another example of a resonant frequency shift sensed by a sensor described herein to identify a particular type of filter housing.

FIG. 24 is a graph illustrating another example of a resonant frequency shift sensed by a sensor to identify a filter housing. As illustrated in FIG. 24, plot 320 includes a horizontal axis representing frequency in Hertz and a vertical axis representing resistance in ohms. In the example of FIG. 24, curve 322 represents a measured frequency of an antenna without an identification strip present. In the example of FIG. 24, curve 324 represents a lower measured resonant frequency with a magnetic identification strip in communication with the antenna, as compared to the measured frequency of an antenna without an identification strip present. In the example of FIG. 24, curve 326 represents a higher measured resonant frequency with a conductive identification strip in communication with the antenna, as compared to the measured frequency of an antenna without an identification strip present. In other words, curve 326 may represent a resonant frequency property of the antenna, as measured by the controller, after a filter has been inserted. The magnitude and direction of the resonant frequency shift may be correlated, by the controller, to preconfigured data associating expected resonant frequency ranges to different types of filters, thereby allowing the controller to determine whether an expected type of filter was indeed installed.

Figure 25:
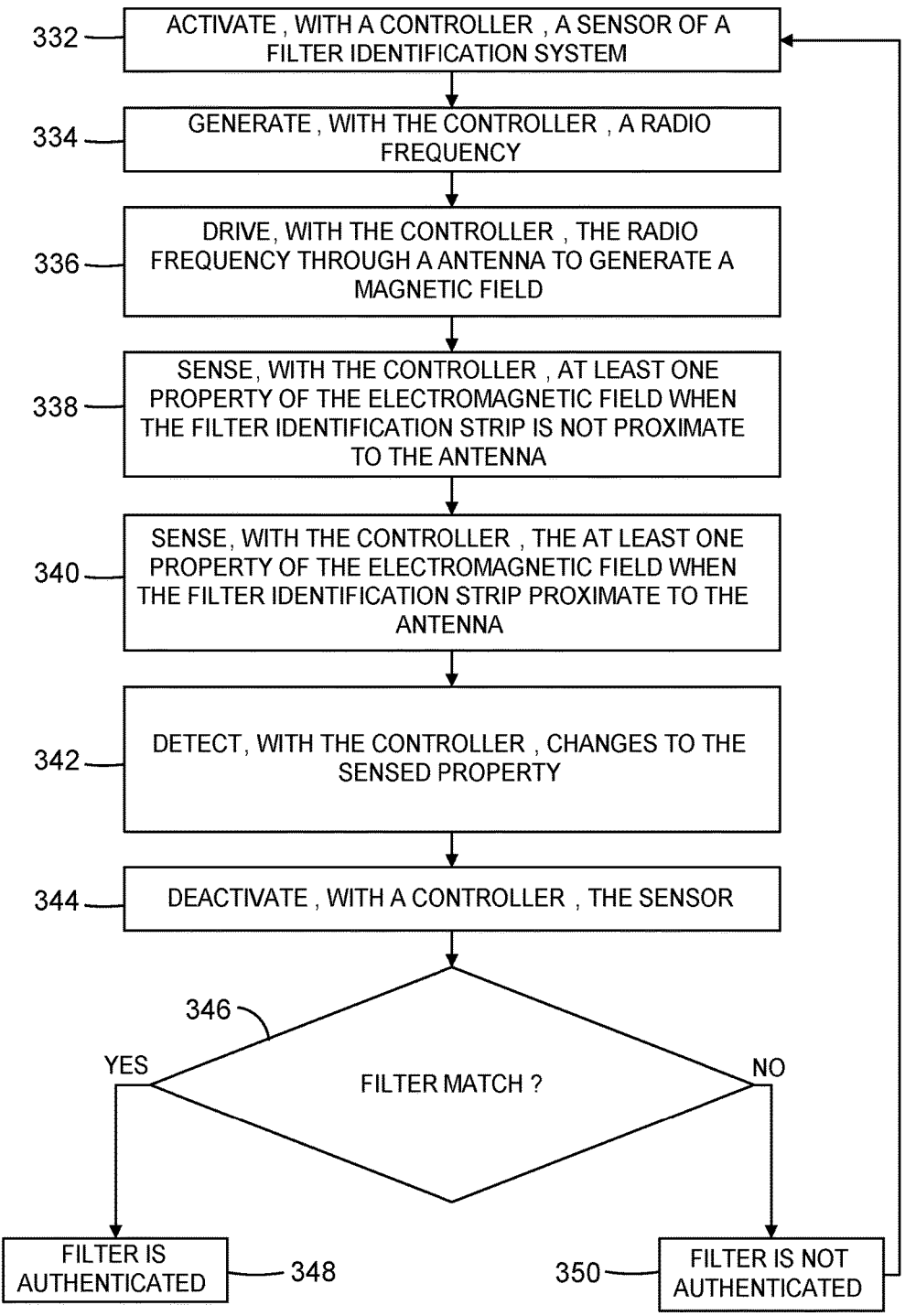
FIG. 25 is a flow diagram illustrating an example process performed by any of the sensors described herein to automatically identify a type of filter by detecting shifts in resonant frequency in an antenna induced by one or more identification strips (conductive and/or magnetic) of a filter housing.

FIG. 25 is a flow diagram illustrating an example process performed by any of the sensors described herein to automatically identify a type of filter by detecting shifts in resonant frequency in an antenna induced by one or more identification strips (conductive and/or magnetic) of a filter housing. Various filtration systems and filter configurations may be used with various techniques described in this disclosure. The technique of FIG. 25 will be described with respect to filter identification system 302 of FIG. 23 for purposes of illustration. However, it will be understood that the technique of FIG. 25 may be performed for a different filter identification system configuration, and that utilizing a filter identification system may include other techniques not explicitly described in FIG. 25. For instance, in some examples, the filter media may be a non-filtering media that provides a response during operation so as to indicate a capacity of the filter media.

In the example of FIG. 25, a sensor of filter identification system 302 is activated by a controller (332). In some examples, the controller may activate the sensor at a predetermined time interval. In some examples, the controller may activate the sensor by user input (e.g., pressing a reset/test button), automated input from an external device (e.g., a signal from a separate controller, or the like). In the example of FIG. 25, the controller generates a radio frequency ("RF") signal (334). In some examples, the RF signal may be a resonant frequency of sensor 308. In the example of FIG. 25, the controller drives the RF signal through sensor 308 to generate an electromagnetic field (336).

In the example of FIG. 25, the controller senses at least one first property of the electromagnetic field when a filter identification strip is not proximate (e.g., not near-field coupled) to the antenna, where the property may be inductance, capacitance, resonant frequency, quality factor, equivalent series resistance, equivalent parallel resistance, or the like (338). Subsequently, the controller again senses the at least one property of the electromagnetic field when the filter identification strip is proximate to the antenna (340). In the example of FIG. 25, responsive to changes in the sensed property or properties, the controller determines a difference between the first measurement and the second measurement (342). In the example of FIG. 25, the controller deactivates the sensor (344). In the example of FIG. 25, the controller determines if the difference is within a predetermined range (346) or otherwise matches a range (e.g., a range of resonant frequencies) matching an expected filter type. As another example, the controller may determine that a profile of the sense property over time matches an expected profile for insertion of the expected filter type. In comparison the controller indicates the expected filter type has been inserted ("YES" branch), filter identification system 302 outputs an indicator or message that the filter housing 312 has been authenticated (348). In some examples, authorization may enable manual reset of a filter lifetime indicator. In the example of FIG. 25, if a match is not detected ("NO" branch), filter identification system 302 does not authenticate filter housing 312 (350), resulting in an alarm or other indicator/message. In some examples, failed authentication may not enable manual reset of a filter lifetime indicator.

Figure 26:
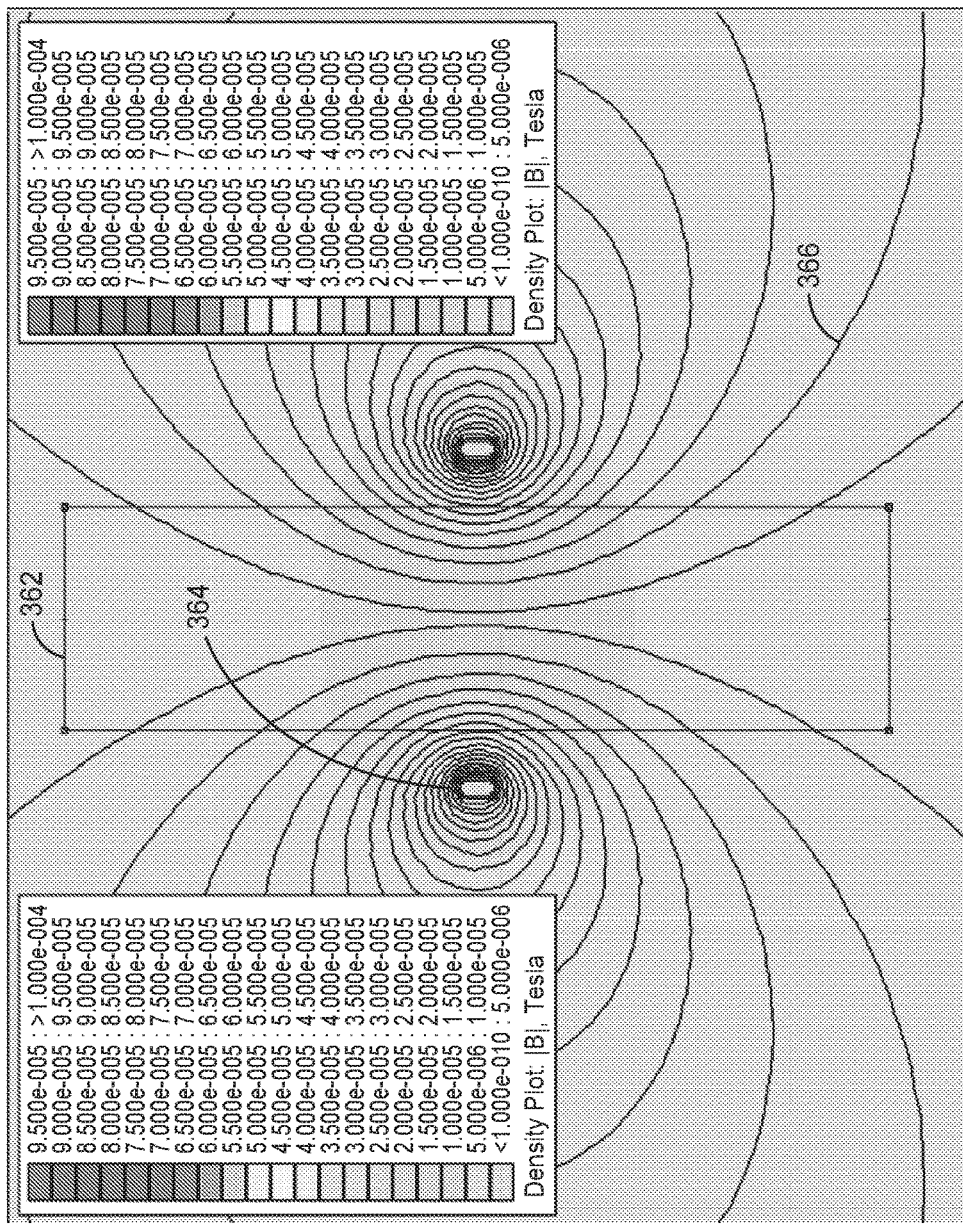
FIG. 26 is a cross-sectional diagram illustrating an example simulated magnetic field of an antenna of a sensor system and a filter housing without a conductive or magnetic identification strip.

FIG. 26 is a cross-sectional diagram along a longitudinal axis of a filter housing 362 to illustrate an example simulated magnetic field produced by antenna 364 (in a plane perpendicular to the longitudinal axis) of sensor system affixed to the filter housing. In the simulated schematic of FIG. 26, cylindrical filter housing 362 is encircled by antenna 364 that generates electromagnetic field 366. In the example of FIG. 26, electromagnetic field 366 propagates unimpeded through the filter housing 362 and filter media (not shown). Moreover, FIG. 26 illustrates example strength of the magnetic field created for sensing a variety of filter media. In some examples, the electromagnetic field 366 may be altered by the conductivity of the filter media during an operation of the filter media.

Figure 27:
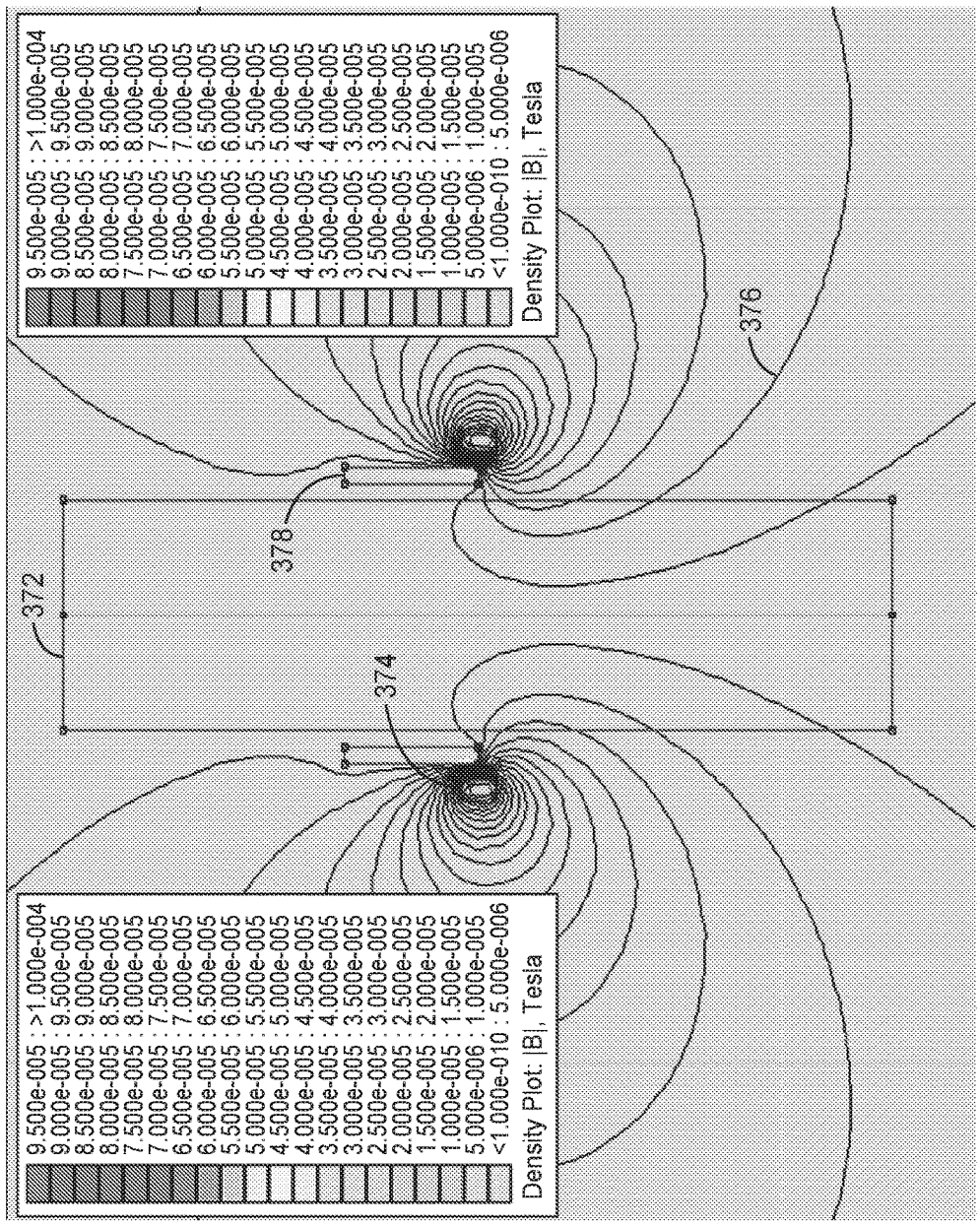
FIG. 27 is a cross-sectional diagram illustrating an example simulated electromagnetic field of an antenna of a sensor system and a conductive identification strip positioned on an exterior of a filter housing.

FIG. 27 is a schematic diagram illustrating an example simulated electromagnetic field of an antenna of a sensor system and a conductive identification strip positioned on an exterior of a filter housing. In the simulated schematic of FIG. 27, cylindrical filter housing 372 is encircled by antenna 374 that generates electromagnetic field 376. In the example of FIG. 27, electromagnetic field 376 propagates through a portion of the filter housing 372 and filter media (not shown). In some examples, the electromagnetic field 376 may be altered by the conductivity of the filter media during an operation of the filter media. In the example of FIG. 27, electromagnetic field 376 does not propagate through conductive ring 378 that encircles filter housing 372. In this way, the simulation of FIG. 27 illustrates that the shape of an electromagnetic field proximate to a filter housing can be modified by a conductive identification strip.

Figure 28:
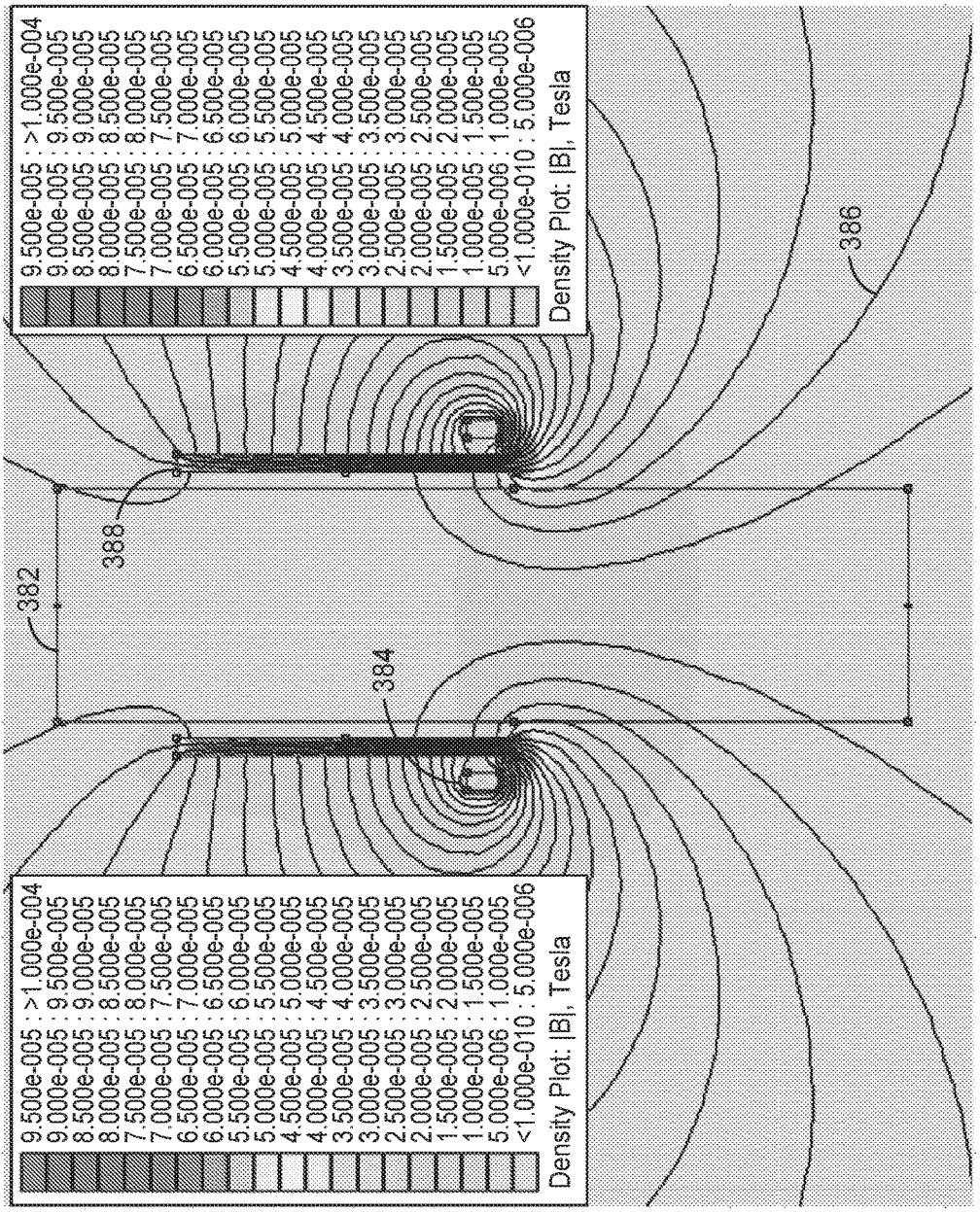
FIG. 28 is a cross-sectional diagram illustrating an example simulated electromagnetic field of an antenna of a sensor system and a magnetic identification strip positioned on an exterior of a filter housing.

FIG. 28 is a schematic diagram illustrating an example simulated electromagnetic field of an antenna of a sensor system and a magnetic identification strip positioned on an exterior of a filter housing. In the simulated schematic of FIG. 28, cylindrical filter housing 382 is encircled by antenna 384 that generates electromagnetic field 386. In the example of FIG. 28, electromagnetic field 386 propagates through a portion of the filter housing 382 and filter media (not shown). In some examples, the electromagnetic field 386 may be altered by the conductivity of the filter media during an operation of the filter media. In the example of FIG. 28, electromagnetic field 386 altered by ferrite ring 388 that encircles filter housing 382. In this way, the simulation shows that the shape of a magnetic field within a filter block can be modified by a magnetic identification strip.

Figure 29:
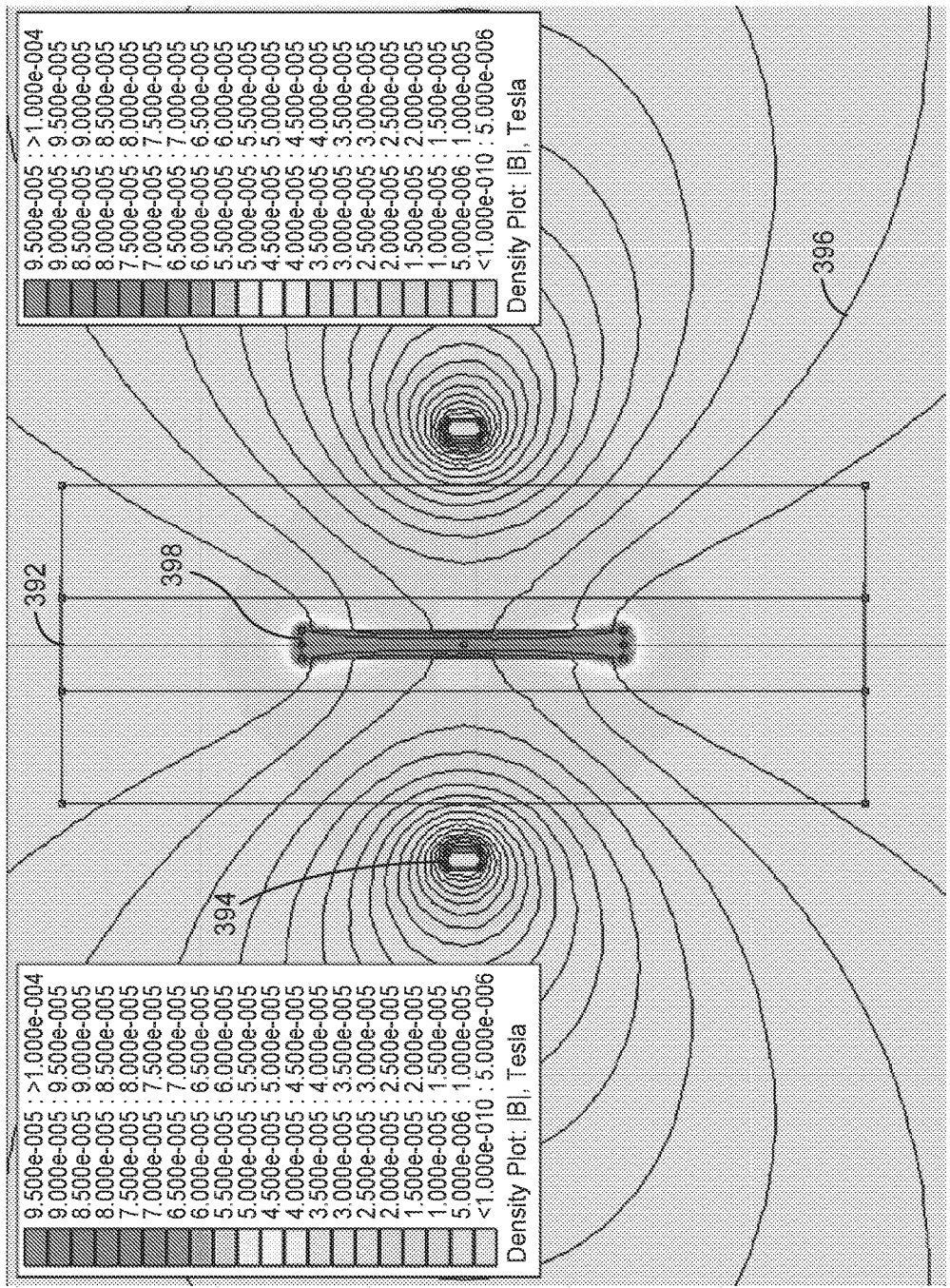
FIG. 29 is a cross-sectional diagram illustrating an example simulated magnetic field of an antenna of a sensor system and a magnetic identification strip positioned on an interior of a filter housing.

FIG. 29 is a schematic diagram illustrating an example simulated magnetic field of an antenna of a sensor system and a magnetic identification strip positioned on an interior of a filter housing. In the simulated schematic of FIG. 29, cylindrical filter housing 392 is encircled by antenna 394 that generates electromagnetic field 396. In the example of FIG. 29, electromagnetic field 396 propagates through a portion of the filter housing 392 and filter media (not shown). In some examples, the electromagnetic field 396 may be altered by the conductivity of the filter media during an operation of the filter media. In the example of FIG. 29, electromagnetic field 396 is altered by ferrite cylinder 398 positioned at an interior of filter housing 392. In this way, simulation shows that the shape of a magnetic field within a filter block can be modified by a magnetic identification strip.

Figure 34A:
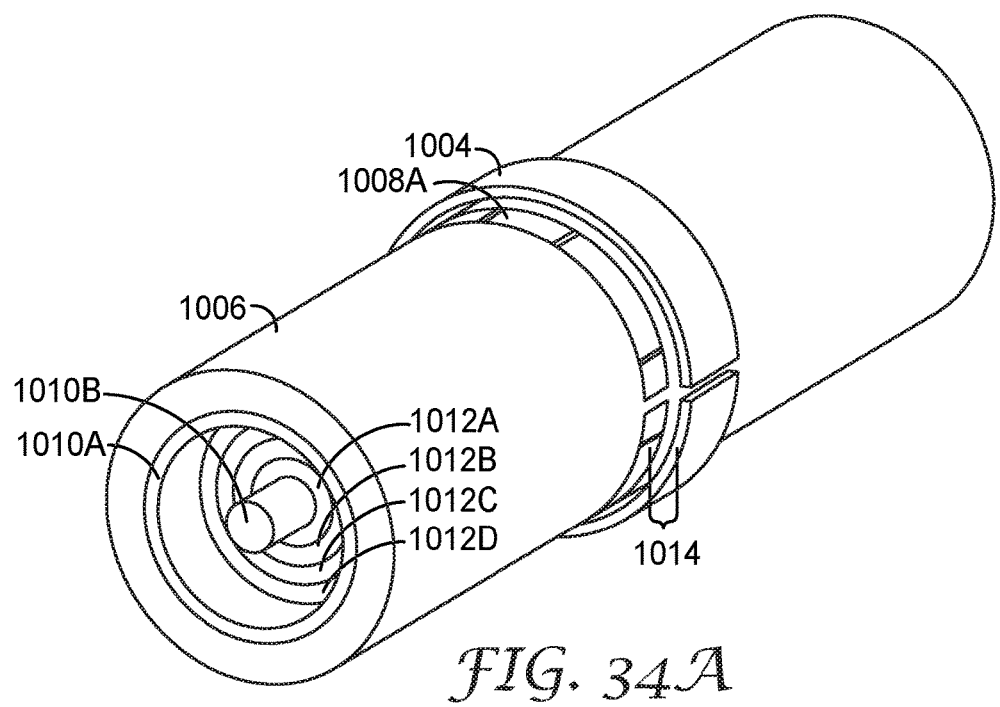
FIGS. 34A and 34B are schematic diagrams illustrating an example filter housing having an identification strip and an antenna of a filter housing identification system.
Figure 34B:
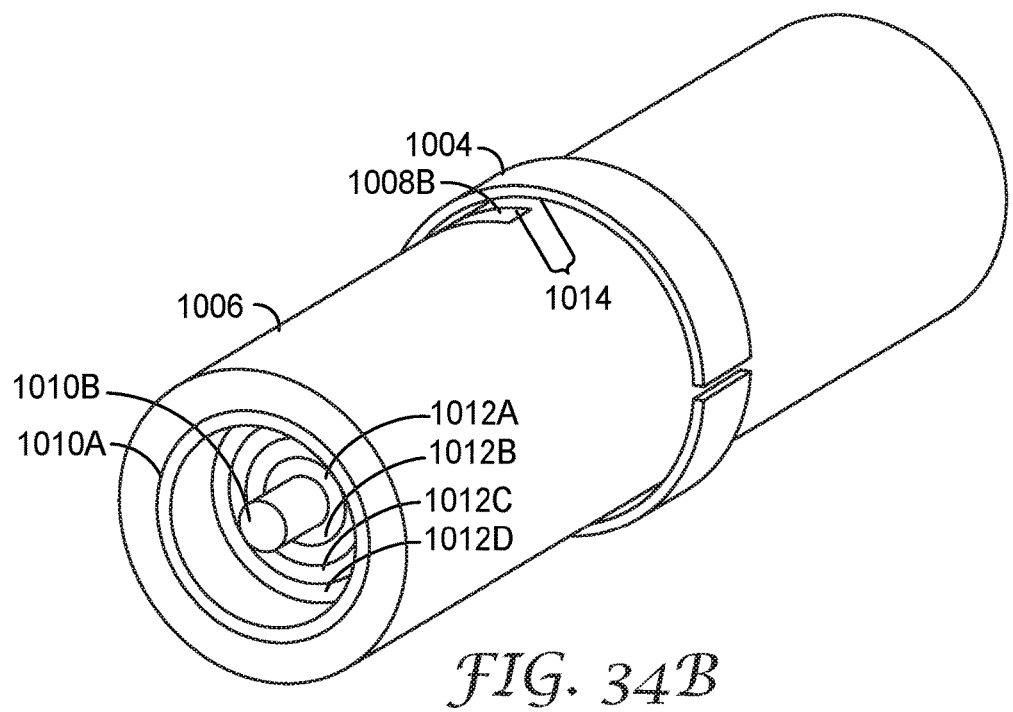

FIGS. 34A and 34B are schematic diagrams illustrating an example filter housing having an identification strip and an antenna of a filter housing identification system. In the examples of FIGS. 34A and 34B, identification strip 1008A, 1008B (generally, "identification strip 1008") is positioned around a circumference of a nonconductive filter housing 1006 containing a fluid inlet 1010A, fluid outlet 1010B, and four filter media layers 1012A, 1012B, 1012C, 1012D (collectively "filter media 1012"). In the example of FIG. 34A, identification strip 1008A encompasses substantially the entire circumference of filter housing 1006, and is located a distance 1014, as measured along the longitudinal axis of the filter housing, from antenna 1004. In the example of FIG. 34B, identification strip 1008B encompasses approximately one half of the circumference of filter housing 1006, and is located a distance 1014, as measured along the longitudinal axis of the filter housing, from antenna 1004. In some examples, identification strip 1008A, 1008B may include one or more conductive strips or magnetic strips. In some examples, one or more identification strips may be positioned around at least a portion of the perimeter of a filter housing 1006. In some examples, the identification strip 1008A, 1008B changes one or more properties of an electromagnetic field generated by antenna 1004 such that the change is dependent on distance 1014. For example, one or more properties of an electromagnetic field generated by antenna 1004 may change as identification strips 1008A, 1008B are positioned closer to or further from antenna 1004.

Figure 35:
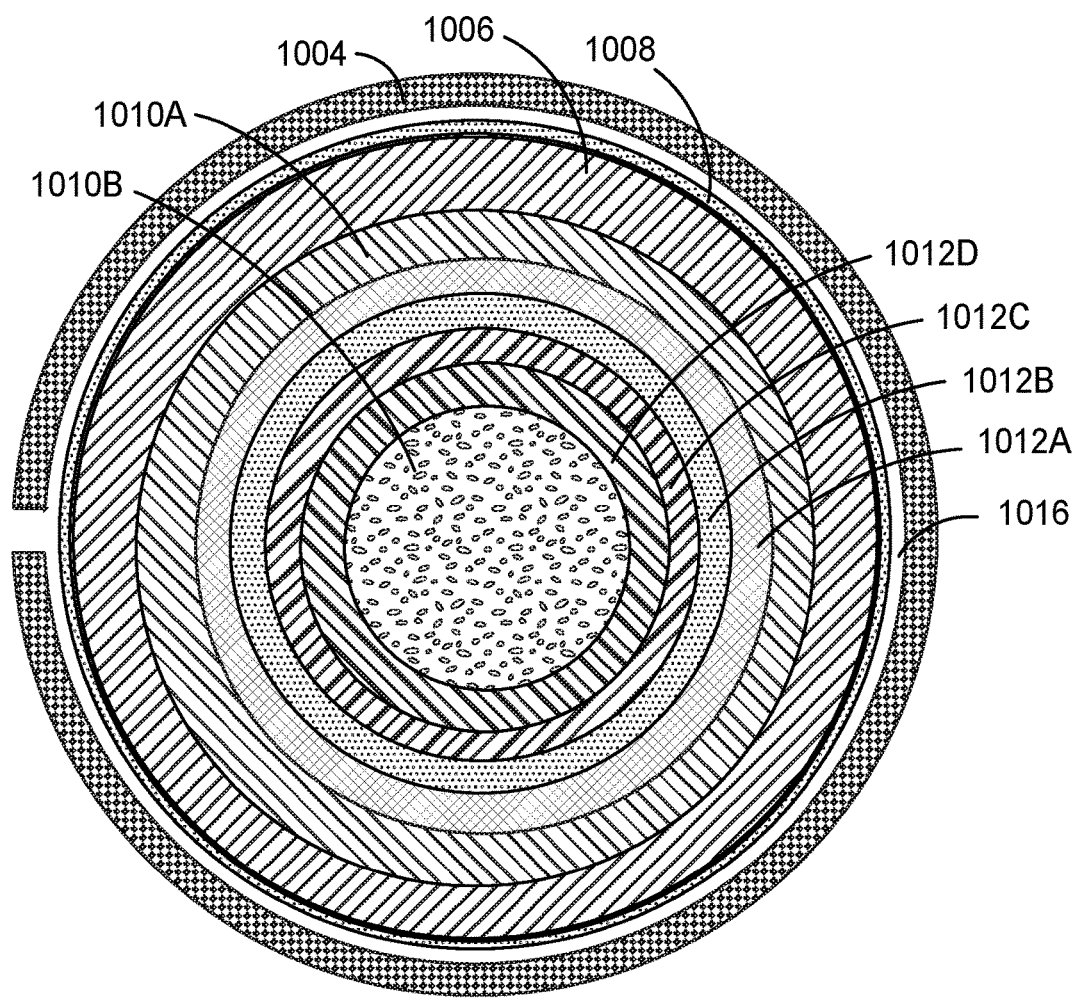
FIG. 35 is a schematic diagram illustrating a cross sectional view of the filter identification system of FIG. 34A.

FIG. 35 is a schematic diagram illustrating a cross sectional view of an example filter housing 1006 having identification strip 1008A and antenna 1004 of FIG. 34A. In the example of FIG. 35, antenna 1004 of a filter identification system encompasses identification strip 1008 and nonconductive filter housing 1006 that contains a fluid inlet 1010A, fluid outlet 1010A, four filter media layers 1012A, 1012B, 1012C, 1012D (collectively "filter media 1012"), and air gap 1016 between antenna 1004 and identification strip 1008 or filter housing 1006.

Simulations were performed using the filter housing identification system of FIGS. 34A, 34B and 35. In the simulations, the antenna consisted of a single-turn copper ($\sigma$=5.8× $10^7$ S/m) inductive loop. The dimensions of the loop were 0.2 cm thick, 1.3 cm wide, and a 2.4 cm inner diameter. A small air gap existed between the antenna and housing. The antenna was modeled as a resonant circuit by electrically connecting at 590 pF capacitance element. The housing consisted of a non-conductive plastic material ($\varepsilon_r$=3, tan $\delta$=0.002). The housing is located between the antenna and the filter. The outer and inner diameter of the housing was 46 mm and 34 mm respectively. The filter was modeled as four concentric layers to allow a simple method the investigate effect of electrical conductivity gradients within the filter. In all cases, the relative dielectric of the filter was 2.5. To represent a new filter, all four layers of were selected to have a conductivity of be 23 S/m. To represent a partially used filter, the outer two layers (layers 3 & 4) and the inner layers (layers 1 & 2) were selected to have conductivities of 6.47 S/m and 23 S/m respectively. Two water layers 1010A, 1010B ($\varepsilon_r$=81, $\sigma$=0.01 S/m) were simulated as located between 1006 housing and filter layer 1012A and a region within the inner radius of filter layer 1012D.

In the simulation the four filter media layers 1012 had the following dimensions:

| | | |
|---|---|---|
| Layer 1012D (Inner Layer): | Inner Diameter: 8 mm | Outer Diameter: 13.5 mm |
| Layer 1012C: | Inner Diameter: 13.5 mm | Outer Diameter: 19.5 mm |
| Layer 1012B: | Inner Diameter: 19.5 mm | Outer Diameter: 24.5 mm |
| Layer 1012A (Outer Layer): | Inner Diameter: 24.5 mm | Outer Diameter: 30 mm |

Figure 36:
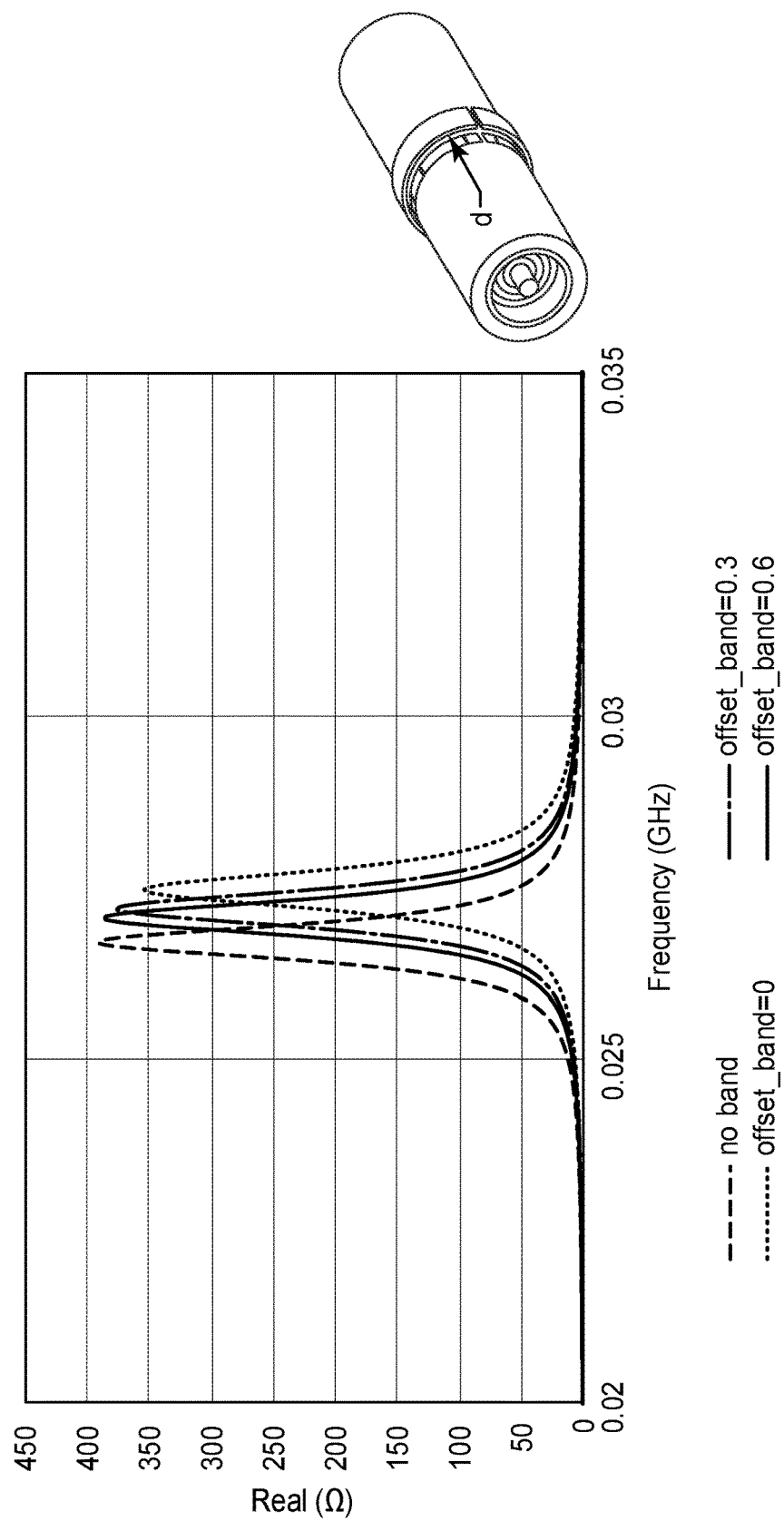
FIGS. 36, 37, 38A, 38B are graphs illustrating example simulated results for computer models of the example filter housing identification system of FIG. 34A.

FIG. 36 is a graph illustrating example simulated results for real impedance of a resonant antenna versus frequency (GHz) of the example filter housing identification system described with respect to FIG. 35. In particular, FIG. 36 shows the real part of the resonant antenna's impedance for a copper band located on the outer surface of the filter housing for three different antenna-band separations of 0.0, 0.3, and 0.6 cm. In the simulation, the dimension of the copper band is ¼" wide, 1.4 mil thick, and nearly fully wraps the filter housing with a 0.2 mm air gap. As the antenna-band separation (d) decreases, the shift in resonant frequency increases. In the application of filter characterization, the antenna-band separation at full insertion can be used to determine the filter type and filtration parameters based on a frequency or amplitude shift. In the application of proximity sensing, the antenna-band separation during insertion can be used to determine proper filter insertion (minimized potential for leak formation), i.e. leak detection.

Figure 37:
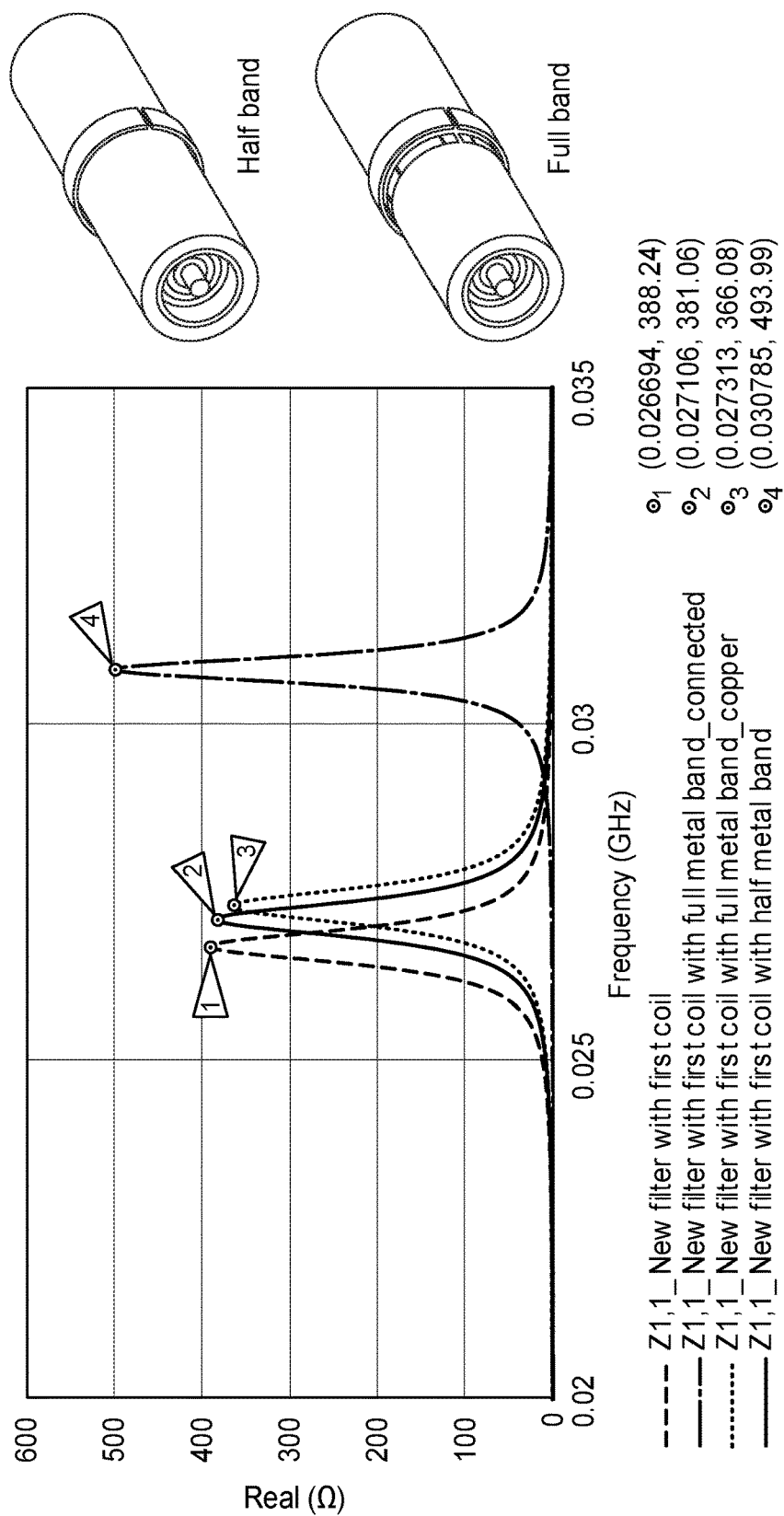

FIG. 37 is another graph illustrating example simulated results showing the real part of the resonant antenna's impedance for a copper band located on the outer surface of the filter housing for three different band lengths: a band that wraps half-way around the housing, a band that nearly fully-wraps the housing with an 0.2 mm air gap, and a band the fully-wraps the housing with ends electrically connected. As the conductive band wraps a larger section of the filter housing, the shift in resonant frequency increases. Electrically connecting the ends of the band results in an increase in resonant frequency shift. The resistance of the connection affects the magnitude in shift. In the application of filter characterization, the length of the band can be used to determine the filter type and filtration parameters. In the application of leak detection, a section of the band comprising a moisture dependent resistor can be used to detect leaks.

In this way, FIG. 37 illustrates a change in the resonant frequency and impedance of the antenna as the circumferential length of the identification band is changed. In some examples, a change is resonant frequency and/or impedance of the antenna based on the identification band length may characterize the filter housing position to determine whether the filter housing is properly seated in a filtration system, which may be used to warn of potential fluid leaks. In other examples, a change is resonant frequency or an impedance of antenna based on the identification band length may characterize other parameters of filter housing.

Figure 38A:
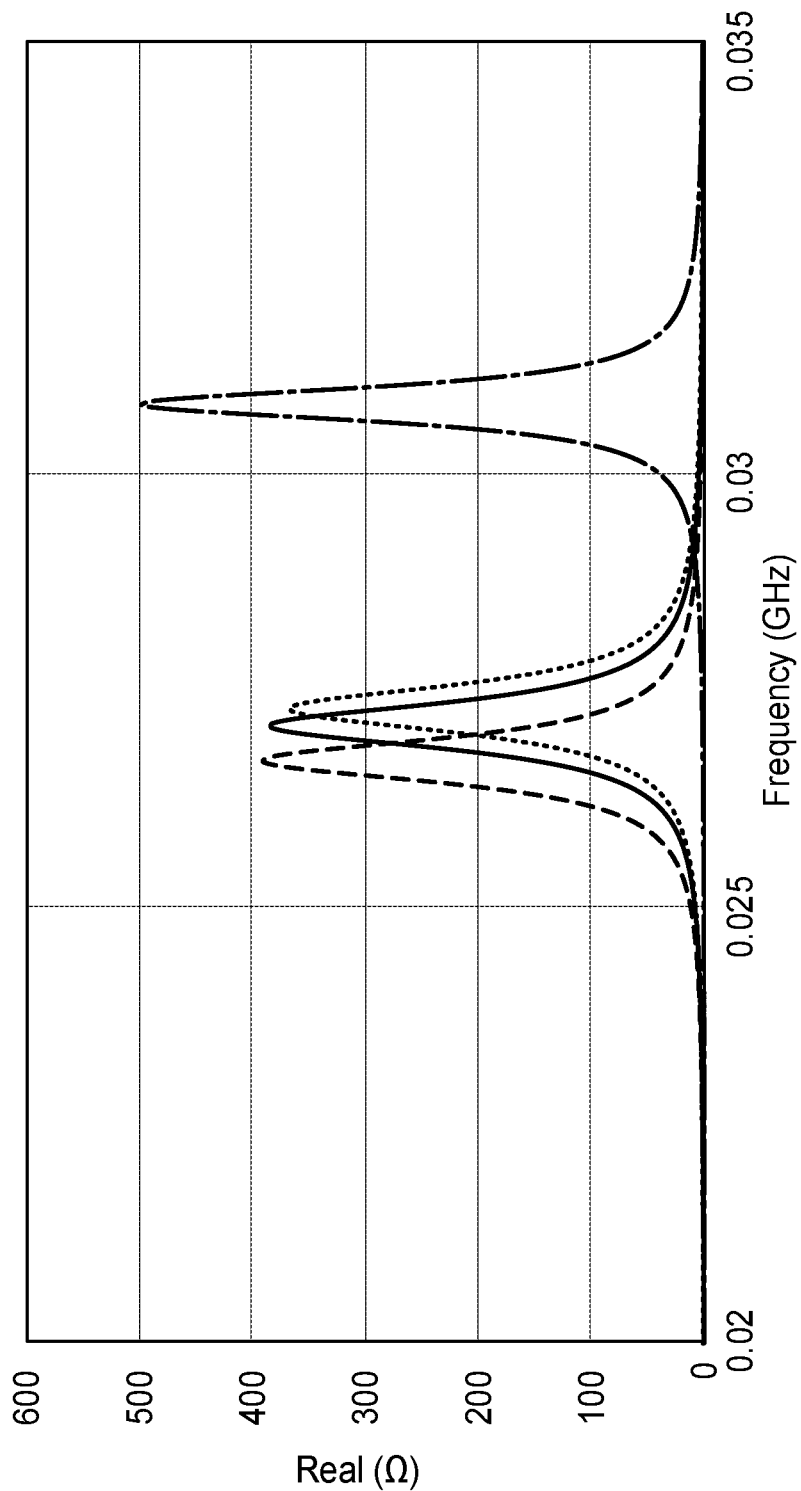
Figure 38B:
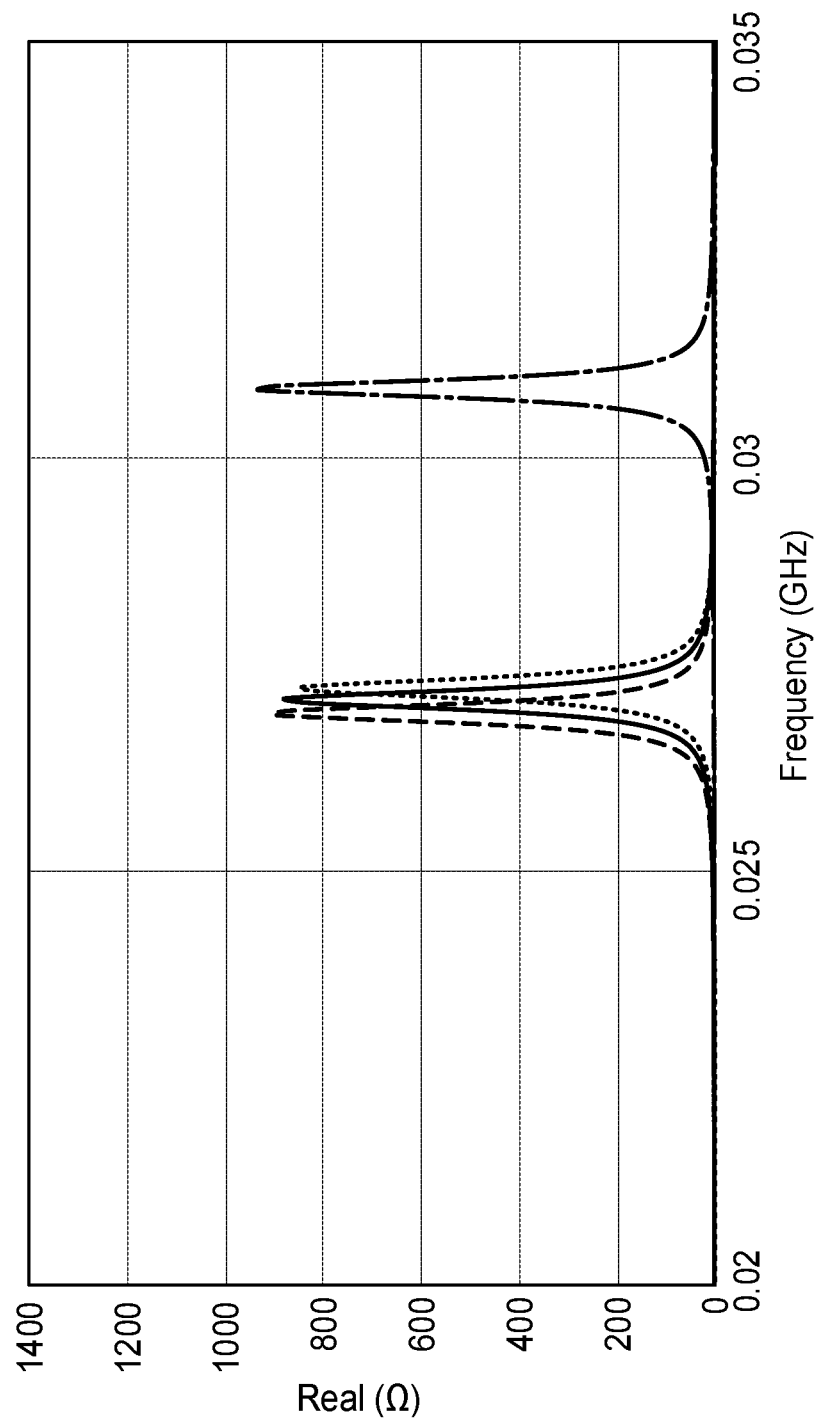

FIGS. 38A and 38B are graphs illustrating example simulated results for resonant frequency shift when using conductive identification bands. In particular, the graphs show the real part of the resonant antenna's impedance for filters with a copper band attached to outer surface of the filter housing with three different lengths: a band that wraps half-way around the housing, a band the nearly fully-wraps the housing with an 0.5 mm air gap, and a band the fully-wraps the housing with ends electrically connected. The figures show the real part of the impedance for two filter conductivities: new filter with a conductivity of 23 S/m for all 4 layers and the partially used filter with a conductivity of 23 S/m for the inner two layers and 6.47 S/m for the outer two layers.

Table 3 shows the experimental results of real impedance in ohms for a new and partially used filter at the respective resonant frequency of four different identification bands.

TABLE 3

| Copper Band Type | Real (Ω) New Filter | Real (Ω) Partially Used Filter | Used/New Ratio |
|---|---|---|---|
| No Band | 389.86 | 902.07 | 2.31 |
| ½ | 381.17 | 875.99 | 2.30 |
| Full - air gap | 365.43 | 843.20 | 2.31 |
| Full - connect ends | 494.75 | 925.93 | 1.87 |

In this way, FIGS. 38A, 38B illustrates that a sensitivity to conductivity changes of the filter media 1012 are similar with and without identification bands 1008 and that changes in resonant frequency and impedance can be used to determine both filter type based on an identification band and filter capacity based on conductivity of a filter media.

FIG. 39 shows four contour plots of a magnetic field of the simulated filter sensing system. In particular, the contour plots show the magnetic field for a resonant antenna without a band, with a ¼ inch wide, 1.4 mil thick copper band, with a 1 inch wide, 1.4 mil thick copper band, and a 1 inch wide, 200 um thick soft magnetic band ($\mu_r'$=100, $\mu_r''$=10).

Figure 40:
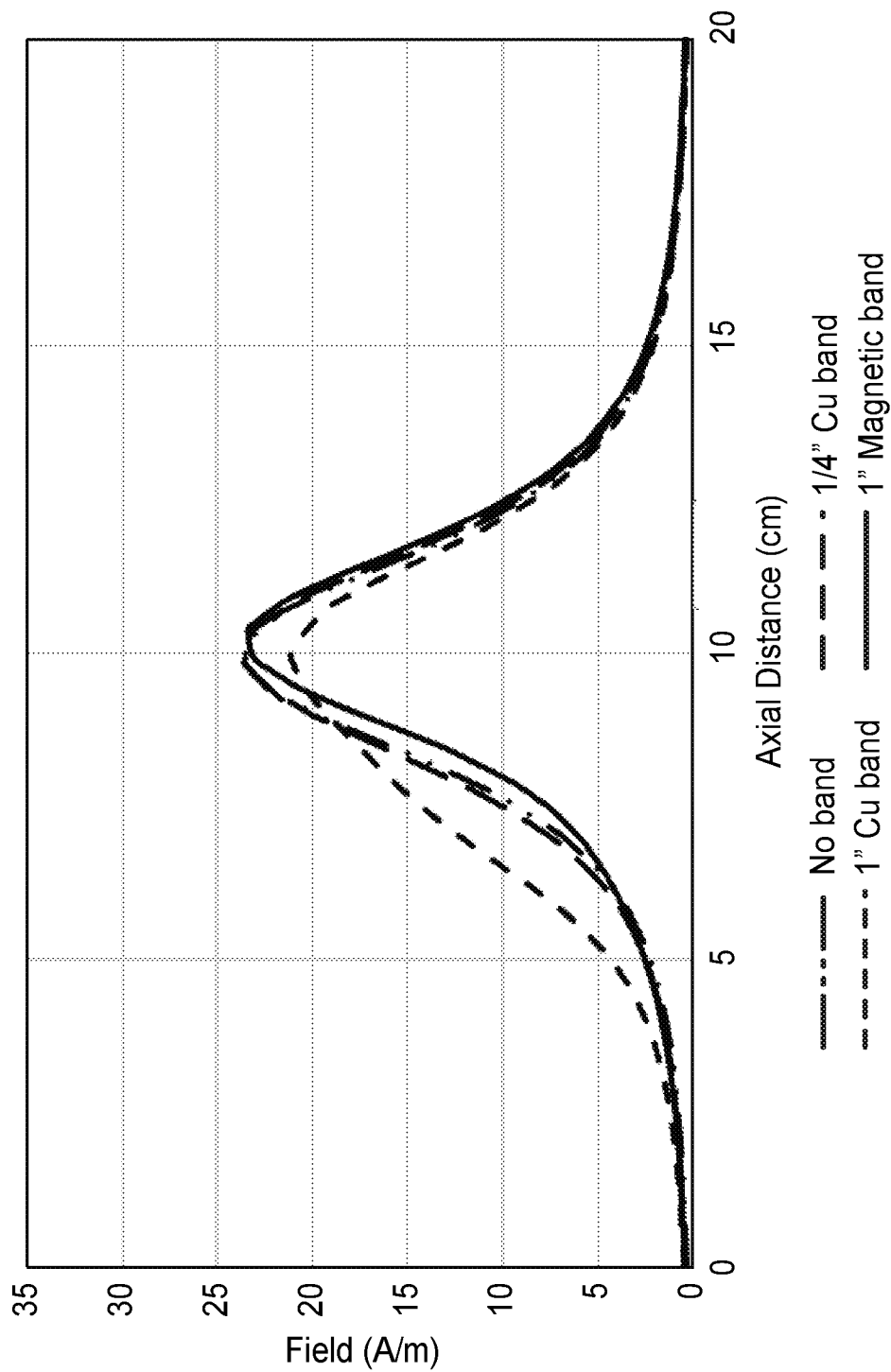
FIG. 40 is a graph showing the magnetic field of FIG. 39 as a function of axial distance along the long axis of the filter.

FIG. 40 is a graph showing the magnetic field of FIG. 39 as a function of axial distance along the long axis of the filter. The axial location is indicated by the dashed line in FIG. 39. The presence of the conductive and magnetic band located on the exterior surface of the filter housing modifies the distribution of the magnetic field from the resonant antenna. As can be seen by these simulations, the presence of a copper band results in the magnetic field to be broadened along the axis of the filter relative to field in the absence of the bands. Redistribution of the magnetic field can be used to probe the filter material in different regions, locations, and volumes.

Figure 41:
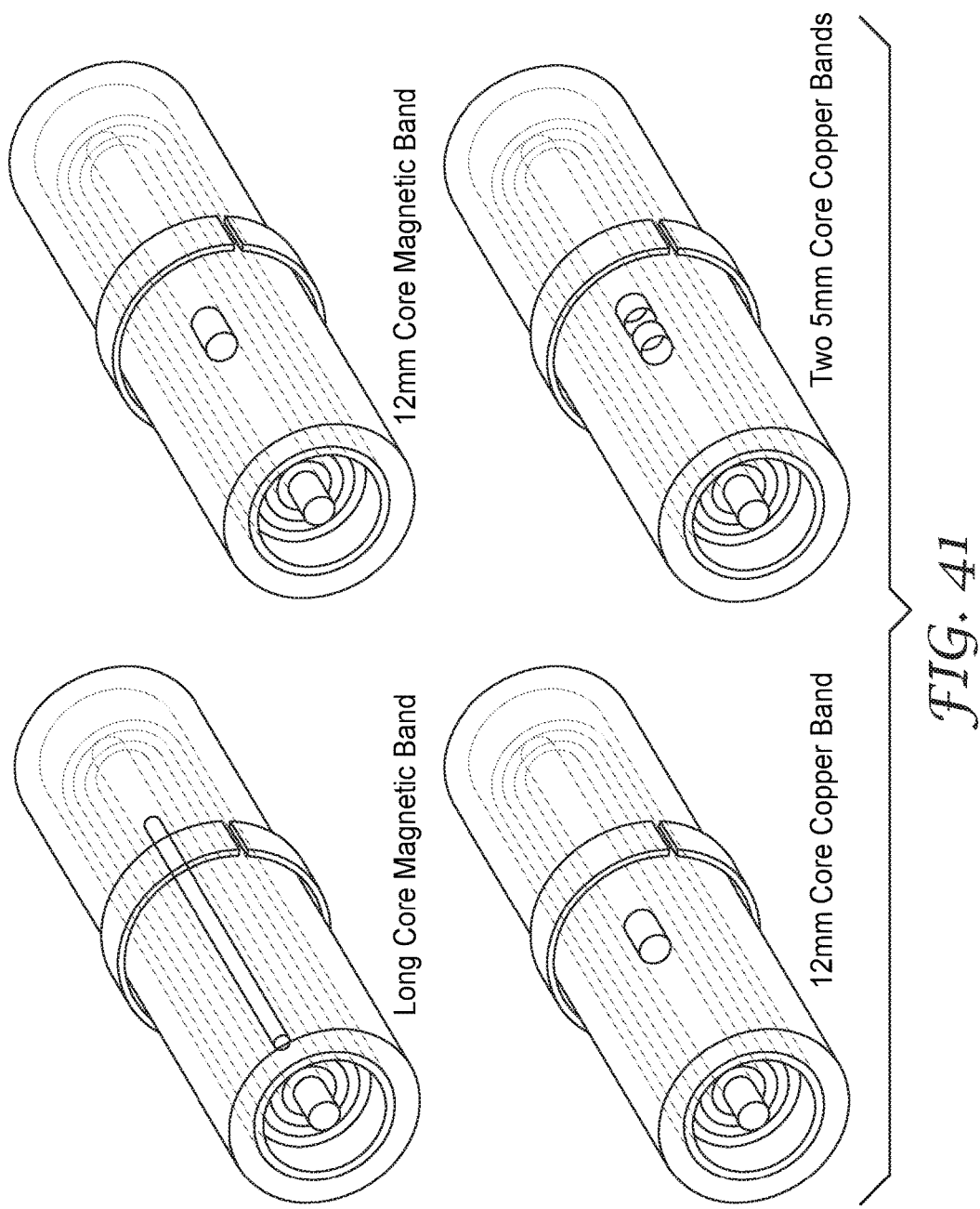
FIG. 41 shows schematic diagrams of filter arrangements and geometries used to model the effect of conductive or magnetic bands located on the inner surface of the filter on the magnetic field distribution and sensor sensitivity.

FIG. 41 shows schematic diagrams of filter arrangements and geometries used to model the effect of conductive or magnetic bands located on the inner surface of the filter on the magnetic field distribution and sensor sensitivity.

Figure 43:
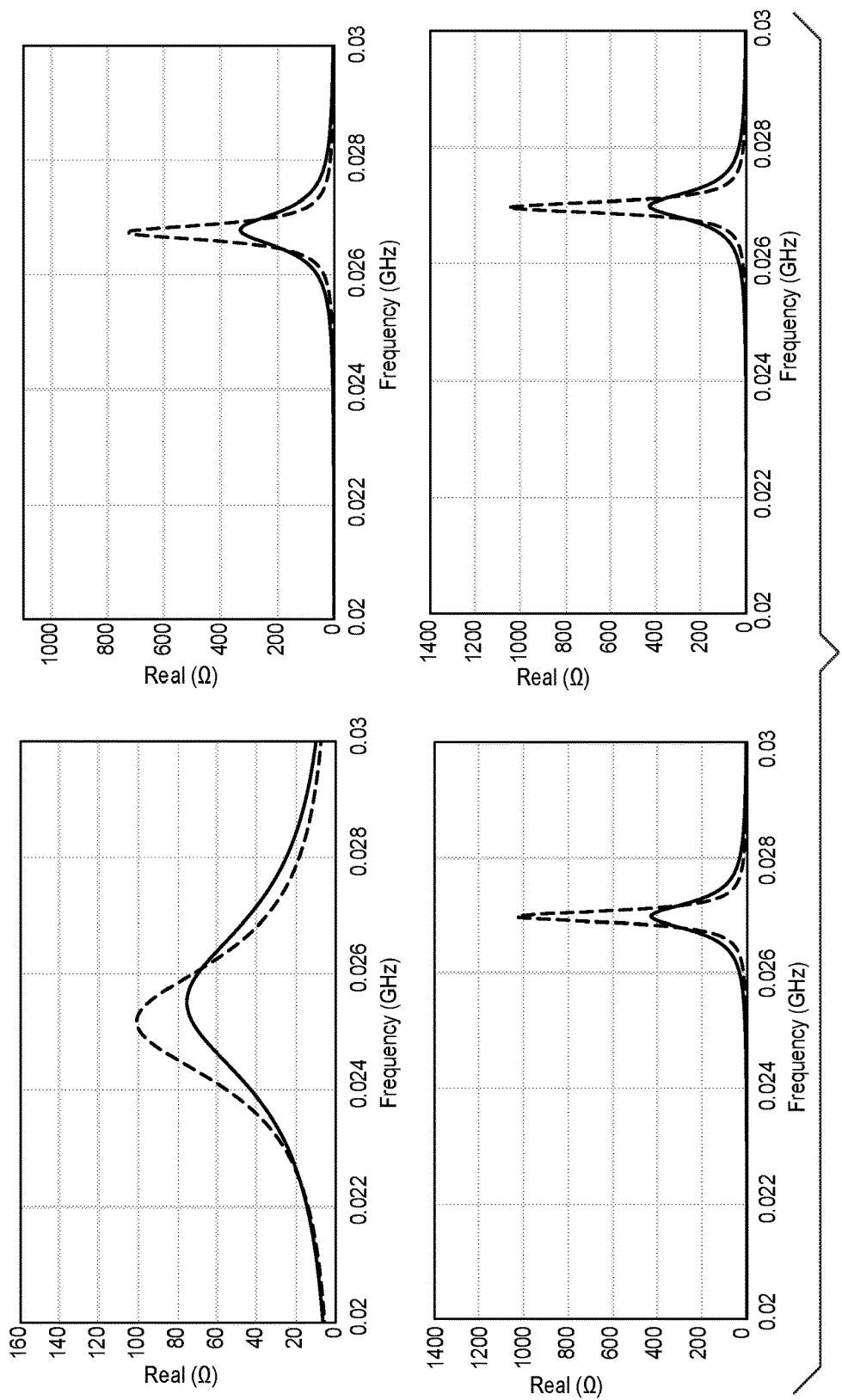
FIG. 43 shows four graphs that depict the effect of modelled conductive and magnetic bands located on the inner surface of the filter on the real impedance and resonant frequency of the resonant antenna.

FIG. 42 shows contour plots of the simulated magnetic fields generated by the filter arrangements of FIG. 41 in which a resonant antenna is used with conductive or magnetic bands located on the inner surface of the filter. In all cases, the presence of the conductive or magnetic material results in a modified distribution of the magnetic field generated from the resonant antenna FIG. 43 shows four graphs that depict the effect of modelled conductive and magnetic bands located on the inner surface of the filter on the real impedance and resonant frequency of the resonant antenna. In all cases, the simulations indicated that as the conductivity of the outer two layers of the filter decreases, the amplitude of the real impedance at resonance increases. Conductive bands located on the inner surface of the filter resulted in a higher used/new ratio relative to without a band. A long core magnetic band increase the change in frequency associated with a change in filter conductivity Table 4 below shows the effect of conductive and magnetic bands located on the inner surface of the filter on the real impedance at resonance ($R_{AF}$). In all cases, as the conductivity of the outer two layers of the filter decreases, the amplitude of the real impedance at resonance increases. The two 5 mm core Cu bands were observed to have the largest change in real impedance caused by a conductivity decrease of the outer two layers of the filter.

TABLE 4

| Copper Band Type | Real (Ω) New Filter | Real (Ω) Partially Used Filter | Used/New Ratio |
|---|---|---|---|
| Long Core Magnetic Band | 75.32 | 100.60 | 1.34 |
| 10 mm Core Magnetic Band | 332.01 | 720.38 | 2.17 |
| 12 mm Core Cu Band | 425.48 | 1027.90 | 2.42 |
| Two 5 mm Core Cu Bands | 417.77 | 1046.30 | 2.50 |

Table 5 below shows the effect of conductive and magnetic bands located on the inner surface of the filter on the resonant frequency of the resonant antenna. In all cases, as the conductivity of the outer two layers of the filter decreases, the resonant frequency decreases. The long core magnetic band was observed to have the largest change in frequency caused by a conductivity decrease of the outer two layers of the filter.

TABLE 5

| Copper Band Type | $f_0$ (MHz) New Filter | $f_0$ (MHz) Partially Used Filter | Used/New Ratio |
|---|---|---|---|
| Long Core Magnetic Band | 25.636 | 25.198 | 0.983 |
| 10 mm Core Magnetic Band | 26.781 | 26.724 | 0.998 |
| 12 mm Core Cu Band | 26.997 | 26.970 | 0.999 |
| Two 5 mm Core Cu Bands | 27.040 | 26.972 | 0.997 |

Figure 44:
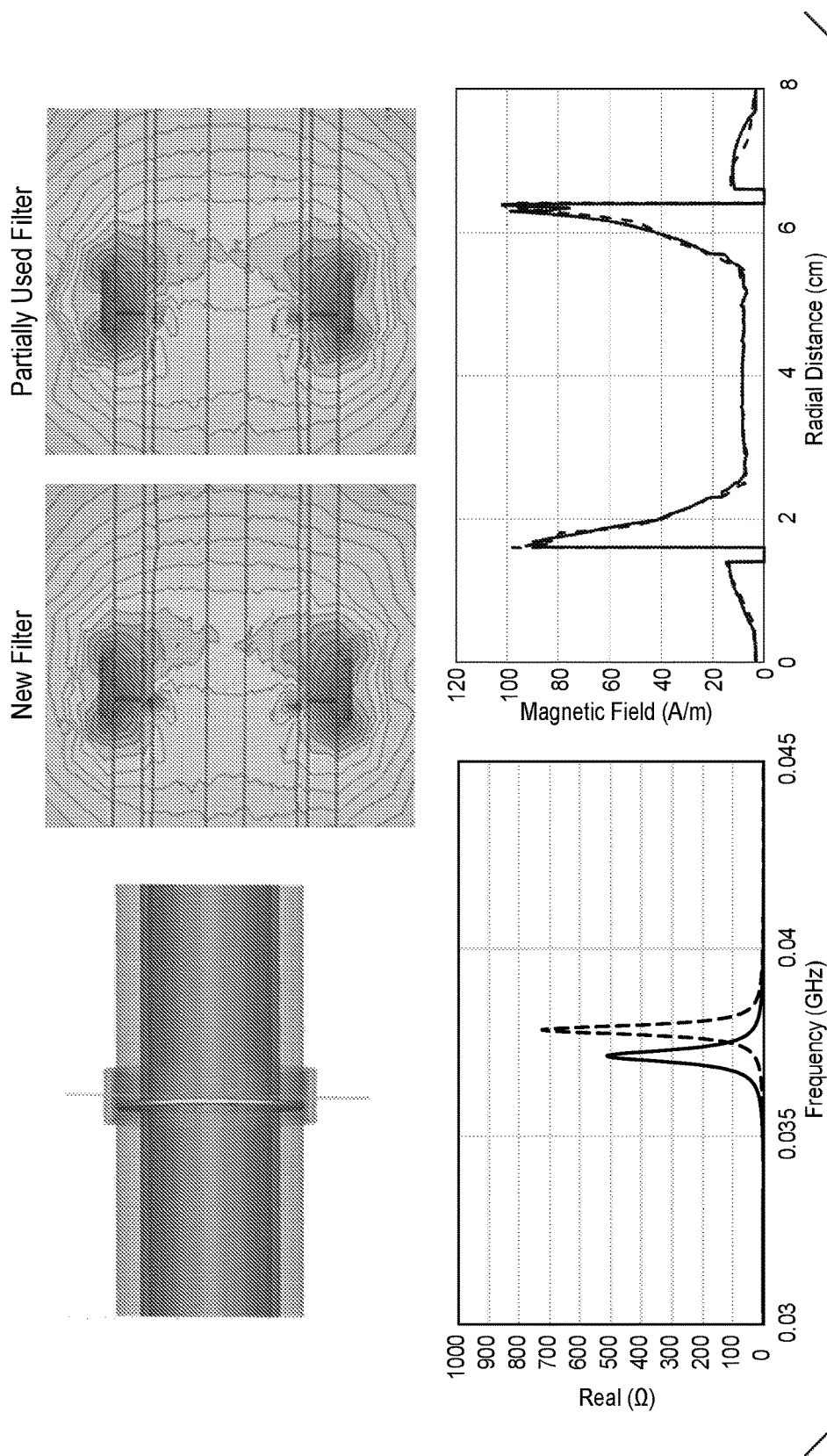
FIG. 44 shows modeling geometry, magnetic field contour plots, modeling geometry, real impedance, and magnetic field for simulations performed for a resonant antenna with a conductive ring embedded into (i.e., integrated within) a plastic filter housing.

FIG. 44 shows modeling geometry, magnetic field contour plots, modeling geometry, real impedance, and magnetic field for simulations performed for a resonant antenna with a conductive ring embedded into (i.e., integrated within) a plastic filter housing. A real impedance and resonant frequency increase occurs when the conductivity of the outer two layers of the filter decreases. In the simulations, a conductive ring embedded into the plastic housing resulted in a large 2-3% shift in resonant frequency caused by a change in filter conductivity.

Although described as identification bands in the previous sections, it is envisioned that in some examples the identification bands may have a different shape or profile that is not a traditional elongated "band" shape. For example, the identification band may have a rectangular, circular, trapezoidal, or triangular shape. In other examples, the band may consist of a flexible, pliable, rigid, bendable, or formable material. In still other examples, the bands may have a primarily 1D, 2D, or 3D profile and be disposed of or within the filter housing.

EXEMPLARY EMBODIMENTS

Embodiment 1. A filter sensor comprising:
an antenna;
a controller electrically coupled to the antenna and configured to drive an electric signal through the antenna to generate an electromagnetic signal,
wherein the antenna is electromagnetically coupled to a filter media via near-field coupling,
wherein the controller is configured to detect a characteristic of the antenna, wherein the characteristic of the antenna varies in response to a change of the filter media, and wherein the controller is further configured to determine an indicator indicative of a remaining filter capacity of the filter media based on the characteristic of the antenna.

Embodiment 2. The filter sensor of Embodiment 1, wherein the characteristic of the antenna comprises at least one of an inductance, capacitance, reactance, impedance, equivalent series resistance, equivalent parallel resistance, quality factor and resonant frequency.

Embodiment 3. The filter sensor of Embodiment 1 or 2, wherein the characteristic of the antenna varies in response to a change of a material property of the filter media that changes over time during filtration, and wherein the material property comprises at least one of an electrical conductivity, magnetic permeability, magnetic loss tangent, magnetic coercively, magnetic saturation, dielectric constant, dielectric loss tangent or dielectric strength of the filter media.

Embodiment 4. The filter sensor of any one of Embodiments 1-3, further comprising: a sensor housing containing the antenna and the controller, wherein the sensor housing is annular shaped having an inner diameter sized to encompass a diameter of a filter housing containing the filter media, and wherein the antenna comprises one or more loops arranged to wind around the sensor housing to encircle the filter housing.

Embodiment 5. The filter sensor of any one of Embodiments 1-4, wherein the sensor is configured to be used with at least one of a filter system, an appliance, a personal respirator device, an HVAC system or a natural gas distribution system.

Embodiment 6. The filter sensor of any one of Embodiments 1-5, wherein the controller is further configured to compare the remaining filter capacity to a threshold.

Embodiment 7. The filter sensor of Embodiment 6, wherein the controller is further configured to output an alert when the remaining filter capacity falls below the threshold.

Embodiment 8. The filter sensor of any one of Embodiments 1-7, wherein the sensor comprises a low electromagnetic loss material.

Embodiment 9. The filter sensor of any one of Embodiments 1-8, wherein the antenna is an inductive element.

Embodiment 10. The filter sensor of any one of Embodiments 1-9, wherein the antenna is a capacitive element.

Embodiment 11. The filter sensor of any one of Embodiments 1-10, wherein the antenna is a loop antenna.

Embodiment 12. The filter sensor of any one of Embodiments 1-11, wherein the antenna is a single turn antenna.

Embodiment 13. The filter sensor of any one of Embodiments 1-12, wherein the antenna is a multiple-turn antenna.

Embodiment 14. The filter sensor of any one of Embodiments 1-13, wherein the controller is configured to drive an electric signal through the antenna at a frequency at which the antenna is non-resonant.

Embodiment 15. The filter sensor of any one of Embodiments 1-14, wherein the controller is configured to drive an electric signal through the antenna at a frequency at which the antenna is resonant.

Embodiment 16. The filter sensor of any one of Embodiments 1-15, wherein the antenna is resonant at a frequency higher than 50 kHz.

Embodiment 17. The filter sensor of any one of Embodiments 1-16, wherein the antenna is resonant at a frequency higher than 100 kHz.

Embodiment 18. The filter sensor of any one of Embodiments 1-17, wherein the antenna is resonant at a frequency lower than 5.8 GHz.

Embodiment 19. The filter sensor of any one of Embodiments 1-18, further comprising: a second antenna operating at a second frequency different from the frequency of the antenna.

Embodiment 20. The filter sensor of any one of Embodiments 1-19, wherein an equivalent parallel resistance of the antenna is greater than 0.001 times a coupled resistance of the filter media.

Embodiment 21. The filter sensor of any one of Embodiments 1-20, wherein an equivalent parallel resistance of the antenna is greater than 0.01 times a coupled resistance of the filter media.

Embodiment 22. The filter sensor of any one of Embodiments 1-21, wherein an equivalent parallel resistance of the antenna is greater than 0.1 times a coupled resistance of the filter media.

Embodiment 23. The filter sensor of any one of Embodiments 1-22, wherein an equivalent parallel resistance of the antenna is greater than a coupled resistance of the filter media.

Embodiment 24. The filter sensor of any one of Embodiments 1-23, wherein the antenna has a q-factor less than 10,000.

Embodiment 25. The filter sensor of any one of Embodiments 1-24, wherein the antenna has a q-factor less than 1,000.

Embodiment 26. The filter sensor of any one of Embodiments 1-25, wherein the antenna has a q-factor less than 500.

Embodiment 27. The filter sensor of any one of Embodiments 1-26, wherein the antenna has a q-factor greater than 1.

Embodiment 28. The filter sensor of any one of Embodiments 1-27, wherein the antenna has a q-factor greater than 10.

Embodiment 29. The filter sensor of any one of Embodiments 1-28, wherein the antenna is inductively coupled to the filter media.

Embodiment 30. The filter sensor of any one of Embodiments 1-29, wherein the antenna is capacitively coupled to the filter media.

Embodiment 31. The filter sensor of any one of Embodiments 1-30, wherein the antenna is configured to encompass the filter media.

Embodiment 32. The filter sensor of any one of Embodiments 1-31, wherein the antenna is configured to be contained within the filter media.

Embodiment 33. The filter sensor of any one of Embodiments 1-32, wherein the antenna is configured to be disposed proximal to the filter housing.

Embodiment 34. The filter sensor of any one of Embodiments 1-33, wherein the antenna is configured to be contained within to the filter housing.

Embodiment 35. The filter sensor of any one of Embodiments 1-34, wherein the antenna is configured to be contained within a recess of the filter housing.

Embodiment 36. The filter sensor of any one of Embodiments 1-35, wherein the antenna is configured to be the filter housing.

Embodiment 38. A filter sensor comprising:
a sensor housing having an annular shape to encircle a filter housing containing a filter media;
an antenna within the sensor housing to encircle the filter housing; and
a controller to drive an electronic signal through the antenna to generate an electromagnetic field within at least a portion of the filter media,
wherein the controller is configured to detect a property of the electromagnetic field indicative of a remaining filter capacity of the filter media.

Embodiment 39. A filtration system comprising:
a filter housing positioned along a flow path conveying a fluid, the filter housing containing a filter media to filter the fluid;
a filter sensor comprising an antenna and a controller,
wherein the controller is configured to drive an electrical signal through the antenna to generate an electromagnetic signal configured to form an electromagnetic field through at least a portion of the filter media and near-field couple the antenna to at least a portion of the filter media, and
wherein the controller is configured detect a characteristic of the antenna influenced by the near-field coupling with the filter media contained within the filter housing and, responsive to the detected characteristic, determine a remaining filter capacity of the filter media.

Embodiment 40. The filtration system of Embodiment 39, wherein the characteristic of the antenna comprises one of an inductance, capacitance, reactance, impedance, equivalent series resistance, equivalent parallel resistance, quality factor and resonant frequency.

Embodiment 41. The filtration system of Embodiment 39 or 40, wherein the characteristic of the antenna changes over time responsive to changes in a material property of the filter media, and wherein the material property is one of an electrical conductivity, magnetic permeability, magnetic loss tangent, magnetic coercivity, magnetic saturation, dielectric constant, dielectric loss tangent or dielectric strength of the filter media.

Embodiment 42. The filtration system of any one of Embodiments 39-41, wherein the sensor further comprises a housing containing the antenna and the controller, wherein the housing is annular shaped having an inner diameter sized to encompass a diameter of a filter housing, and wherein the antenna comprises one or more loops arranged to wind around the housing to encircle the filter housing.

Embodiment 43. The filtration system of any one of Embodiments 39-42, wherein the sensor is configured to connect to one or more of a filter system, an appliance, a personal respirator device, an HVAC system or a natural gas distribution system.

Embodiment 44. The filtration system of any one of Embodiments 39-43, wherein the filter media is configured for water filtration or air filtration.

Embodiment 45. The filtration system of any one of Embodiments 39-44, wherein the filter media is a block media or granular.

Embodiment 46. The filtration system of any one of Embodiments 39-45, wherein the filter media is one of electret, non-woven or an ion-exchange media.

Embodiment 47. The filtration system of any one of Embodiments 39-46, wherein the filter media contains carbonaceous materials, and wherein the controller is configured to determine the remaining filter capacity of the filter media by monitoring, over time, changes to the characteristic of the antenna.

Embodiment 48. The filtration system of any one of Embodiments 39-47, wherein the sensor comprises the sensor of any of Embodiments 1-38.

Embodiment 49. A method comprising:
generating, with an antenna of a sensor, an electromagnetic signal that near-field couples to at least a portion of a filter media contained within a filter housing connected within a filtration system;
detecting a change in at least one characteristics of the antenna influenced by the filter media contained within the filter housing; and
responsive to the detected characteristic, determining a remaining filter capacity of the filter media.

Embodiment 50. The method of Embodiment 49, wherein detecting a change in at least one characteristic of the antenna comprises detecting a change in at least one of an inductance, capacitance, reactance, impedance, equivalent parallel resistance, quality factor and resonant frequency.

Embodiment 51. The method of Embodiment 49 or 50, wherein detecting a change in at least one characteristic of the antenna comprises detecting a change that is responsive to a change in an a material property of the filter media over time during filtration of a fluid by the filter media, and wherein the material property is one of an electrical conductivity, magnetic permeability, magnetic loss tangent, magnetic coercivity, magnetic saturation, dielectric constant, dielectric loss tangent or dielectric strength of the filter media.

Embodiment 52. The method of any one of Embodiments 49-51, further comprising determining whether the remaining filter capacity of the filter media is within a threshold range.

Embodiment 53. The method of Embodiment 52, further comprising generating, with the controller, an alarm signal in response to determining that the current capacity is below the threshold range.

Embodiment 54. The method of any one of Embodiments 49-53, further comprising communicated the detected change in the characteristic to a remote monitor.

Embodiment 55. A water filtration system comprising:

a filter housing comprising an inlet through which untreated water enters and an outlet from which treated water exits;

a filter media contained within the filter housing configured to filter the water passing through the filter housing; and a filter sensor comprising a controller configured to generate a radio frequency signal at a frequency selected to resonate within the filter housing as a resonant cavity to form a standing wave within the filter housing that propagates through at least a portion of the filter media, wherein the controller is configured to detect a property of the resonant cavity due to a conductivity of the water filtration media and, based on the detected property, determine a remaining filter capacity of the water filtration media.

Embodiment 56. The water filtration system of Embodiment 55, wherein the at least one characteristic detected by the controller comprises one of an inductance, capacitance, reactance, impedance, equivalent series resistance, equivalent parallel resistance, quality factor and resonant frequency.

Embodiment 57. The water filtration system of Embodiment 55 or 56, wherein the filter housing comprises one or more of a waveguide, a port or a window and configured to direct the radio frequency signal into the filter housing.

Embodiment 58. The water filtration system of any one of Embodiments 55-57, wherein the controller is further configured to detect a change of the property of the resonant cavity due to a conductivity of the water filtration media and, based on the detected change, determine the remaining filter capacity of the water filtration media.

Embodiment 59. A sensor comprising:

a controller configured to generate a radio frequency signal at a selected frequency to resonate within a filter housing containing a water filtration media to form a standing wave within the filter housing that propagates through at least a portion of the filter media, wherein the controller is configured to detect a change to a property of the standing wave due to a conductivity of the water filtration media and, based on the detected change to the property, determine a remaining filter capacity of the water filtration media.

Embodiment 60. The sensor of Embodiment 59, wherein the at least one characteristic detected by the controller comprises one of a frequency, magnitude, phase, and polarization.

Embodiment 61. A method comprising:

generating, with a sensor proximate a filter housing containing a water filtration media, a radio frequency (RF) signal at a frequency selected to resonate within the filter housing as a resonant cavity to form a standing wave within the filter housing that propagates through at least a portion of the filter media;

detecting a change to a property of the resonant cavity due to a conductivity of the water filtration media and, based on the detected property, by a controller, determining a remaining filter capacity of the water filtration media.

Embodiment 62. The method of Embodiment 61, wherein the detected property comprises one of an inductance, capacitance, reactance, impedance, equivalent series resistance, equivalent parallel resistance, quality factor and resonant frequency.

Embodiment 63. The method of Embodiment 61 or 62, further comprising: comparing, with the controller, the remaining filter capacity of the filter media based on a comparison of a property of the standing wave with a threshold.

Embodiment 64. The method of any one of Embodiments 61-63, further comprising: generating, with the controller, an alarm signal.

Embodiment 65. The method of any one of Embodiments 61-64, further comprising: communicating the detected property to a remote monitor.

Embodiment 66. A filtration system comprising:

a first filter housing positioned along a first flow path conveying a first fluid, the filter housing containing a first filter media to filter the first fluid;

a first filter sensor comprising a first antenna and a first controller, wherein the first controller is configured to drive a first signal through the first antenna to generate a first electromagnetic signal, through the first antenna to generate an electromagnetic signal, wherein the first antenna is electromagnetically coupled to the first filter media via near-field coupling, and wherein the first controller is configured detect a characteristic of the first antenna influenced by the near-field coupling with the first filter media;

a second filter housing positioned along a second flow path conveying a second fluid, the second filter housing containing a second filter media to filter the second fluid;

a second filter sensor comprising a second antenna and a second controller, wherein the second controller is configured to drive a second signal through the second antenna to generate a second electromagnetic signal, wherein the second antenna is electromagnetically coupled to the second filter media via near-field coupling, wherein the second controller is configured detect a characteristic of the second antenna influenced by the near-field coupling with the second filter media; and a monitor configured to determine, responsive to the detected characteristic of the first antenna and the detected characteristic of the second antenna, a remaining filter capacity of the second filter media of the second filter housing.

Embodiment 67. The filtration system of Embodiment 66, wherein the monitor is configured to compensate the remaining filter capacity of the second filter media in response to the detected characteristics of the first antenna.

Embodiment 68. The filtration system of Embodiment 66 or 67, wherein the monitor is configured to determine the remaining filter capacity of the second filter media based on a differential between the detected characteristic of the first antenna and the detected characteristic of the second antenna.

Embodiment 69. The filtration system of any one of Embodiments 66-68, wherein the characteristic of the first antenna and the characteristic of the second antenna comprises one or more of an inductance, capacitance, reactance, impedance, equivalent series resistance, equivalent parallel resistance, quality factor and resonant frequency.

Embodiment 70. The filtration system of any one of Embodiments 66-69, wherein the first filter housing and the second filter housing are a same filter housing, and wherein the first filter media and the second filter media are different portions of a same filter media.

Embodiment 71. The filtration system of any one of Embodiments 66-70, wherein the monitor is positioned remotely from the first sensor and the second sensor.

Embodiment 72. The filtration system of any one of Embodiments 66-71, wherein the monitor is controlled by the second controller of the second sensor.

Embodiment 73. The filtration system of any one of Embodiments 66-72, wherein the sensor comprises any of the sensors of Embodiments 1-38 or 59-60.

Embodiment 74. A method comprising:

generating, with an antenna of a first sensor, an electromagnetic signal that near-field couples to at least a portion of a first filter media contained within a first filter housing connected within a filtration system;

detecting a characteristic of the antenna influenced by the first filter media;

generating, with an antenna of a second sensor, an electromagnetic signal that near-field couples to a second filter media contained within a second filter housing connected within the filtration system;

detecting a characteristic of the antenna of the second sensor influenced by the second filter media contained within the second filter housing; and responsive to the detected characteristic of the antenna of the first sensor and the detected characteristic of the antenna of the second sensor, determining a remaining filter capacity of the second filter media.

Embodiment 75. The method of Embodiment 74, further comprising:

adjusting the determined remaining filter capacity of the second filter media in response to the detected characteristics of the antenna of the first sensor.

Embodiment 76. The method of Embodiment 74 or 75, wherein the first filter housing and the second filter housing are a same filter housing, and wherein the first filter media and the second filter media are different portions of a same filter media.

Embodiment 77. The method of any one of Embodiments 74-76, wherein the characteristic of the antenna comprises at least one of an inductance, capacitance, reactance, impedance, equivalent parallel resistance, quality factor and resonant frequency.

Embodiment 78. The method of any one of Embodiments 74-77, further comprising:

detecting a change in the characteristic of the antenna of the second sensor, wherein the change is responsive to a change in an a material property of the second filter media over time during filtration of a fluid, and wherein the material property is one of an electrical conductivity, magnetic permeability, magnetic loss tangent, magnetic coercivity, magnetic saturation, dielectric constant, dielectric loss tangent or dielectric strength of the filter media Embodiment 79. The method of any one of Embodiments 74-78, further comprising: determining whether the remaining filter capacity of the second filter media is within a range.

Embodiment 80. The method of any one of Embodiments 74-79, further comprising: generating, by a controller, an alarm signal in response to determining that the remaining filter capacity of the second filter media is below a threshold.

Embodiment 81. The method of any one of Embodiments 74-80, further comprising: communicating the determined remaining filter capacity of the second filter media to a remote monitor.

Various aspects of this disclosure have been described. These and other aspects are within the scope of the following claims.

What is claimed is:

1. A filter sensor to be used with a filter media contained in a filter housing, comprising:

an antenna;

a controller electrically coupled to the antenna and configured to drive an electric signal through the antenna to generate an electromagnetic signal, wherein the antenna is configured to electromagnetically couple to the filter media via near-field coupling and configured to encompass the filter media, wherein the controller is configured to detect a characteristic of the antenna, wherein the characteristic of the antenna varies in response to a change of the filter media, and wherein the controller is further configured to determine an indicator indicative of a remaining filter capacity of the filter media based on the characteristic of the antenna.

2. The filter sensor of claim 1, wherein the characteristic of the antenna comprises at least one of an inductance, capacitance, reactance, impedance, equivalent series resistance, equivalent parallel resistance, quality factor and resonant frequency.

3. The filter sensor of claim 1, wherein the characteristic of the antenna varies in response to a change of a material property of the filter media that changes over time during filtration, and wherein the material property comprises at least one of an electrical conductivity, magnetic permeability, magnetic loss tangent, magnetic coercivity, magnetic saturation, dielectric constant, dielectric loss tangent or dielectric strength of the filter media.

4. The filter sensor of claim 1, further comprising: a sensor housing containing the antenna and the controller, wherein the sensor housing is annular shaped having an inner diameter sized to encompass a diameter of the filter housing containing the filter media, and wherein the antenna comprises one or more loops arranged to wind around the sensor housing to encircle the filter housing.

5. The filter sensor of claim 1, wherein the controller is further configured to compare the remaining filter capacity to a threshold.

6. The filter sensor of claim 5, wherein the controller is further configured to output an alert when the remaining filter capacity falls below the threshold.

7. The filter sensor of claim 1, further comprising: a second antenna operating at a second frequency different from the frequency of the antenna.

8. A filtration system comprising:

a filter housing positioned along a flow path conveying a fluid, the filter housing containing a filter media to filter the fluid;

a filter sensor comprising an antenna and a controller, wherein the antenna is disposed exterior to the filter housing, wherein the controller is configured to drive an electrical signal through the antenna to generate an electromagnetic signal configured to form an electromagnetic field through at least a portion of the filter media, and wherein the controller is configured detect a characteristic of the antenna influenced by the near-field coupling with the filter media contained within the filter housing and, responsive to the detected characteristic, determine a remaining filter capacity of the filter media.

9. The filtration system of claim 8, wherein the characteristic of the antenna comprises one of an inductance, capacitance, reactance, impedance, equivalent series resistance, equivalent parallel resistance, quality factor and resonant frequency.

10. The filtration system of claim 8,
wherein the characteristic of the antenna changes over time responsive to changes in a material property of the filter media, and
wherein the material property is one of an electrical conductivity, magnetic permeability, magnetic loss tangent, magnetic coercivity, magnetic saturation, dielectric constant, dielectric loss tangent or dielectric strength of the filter media.

11. The filtration system of claim 8,
wherein the sensor further comprises a housing containing the antenna and the controller, wherein the housing is annular shaped having an inner diameter sized to encompass a diameter of a filter housing, and
wherein the antenna comprises one or more loops arranged to encircle the filter housing.

* * * * *